US008092670B2

(12) United States Patent
Bekki et al.

(10) Patent No.: US 8,092,670 B2
(45) Date of Patent: Jan. 10, 2012

(54) METHOD FOR SPECIFICALLY DETECTING ANALYTE USING PHOTOCURRENT, AND ELECTRODE, MEASURING CELL AND MEASURING DEVICE FOR USE THEREIN

(75) Inventors: Makoto Bekki, Kitakyushu (JP); Hitoshi Ohara, Kitakyushu (JP); Shuji Sonezaki, Kitakyushu (JP); Koki Kanehira, Kitakyushu (JP); Yumi Ogami, Yukuhashi (JP); Hiroshi Ishikawa, Kitakyushu (JP); Yumi Osaki, Suita (JP); Hiromasa Tokudome, Chigasaki (JP); Yoko Yamada, Chigasaki (JP); Masahiro Miyauchi, Fujisawa (JP)

(73) Assignee: Toto Ltd., Fukuoka-ken (JP)

( * ) Notice: Subject to any disclaimer, the term of this patent is extended or adjusted under 35 U.S.C. 154(b) by 957 days.

(21) Appl. No.: 11/992,858

(22) PCT Filed: Sep. 28, 2006

(86) PCT No.: PCT/JP2006/319356
§ 371 (c)(1),
(2), (4) Date: Mar. 28, 2008

(87) PCT Pub. No.: WO2007/037341
PCT Pub. Date: Apr. 5, 2007

(65) Prior Publication Data
US 2009/0294305 A1 Dec. 3, 2009

(30) Foreign Application Priority Data

Sep. 29, 2005 (JP) ................................. 2005-284817
Apr. 4, 2006 (JP) ................................. 2006-103531

(51) Int. Cl.
*G01N 27/26* (2006.01)
*G01N 33/48* (2006.01)
*G01N 33/487* (2006.01)
*G01N 33/49* (2006.01)
*G01N 33/493* (2006.01)
*G01N 33/50* (2006.01)
*G01N 33/53* (2006.01)
*G01N 33/533* (2006.01)

(52) U.S. Cl. ............. 205/792; 205/793.5; 435/4; 435/6; 435/7.1

(58) Field of Classification Search ................... 436/525, 436/2, 52; 435/4, 6, 7.1, 287.1, 287.2, 287.3, 435/292.1, 817; 204/403.1, 409; 205/792, 205/793.5
See application file for complete search history.

(56) References Cited

U.S. PATENT DOCUMENTS 6,653,701 B1 11/2003 Yamazaki et al.
7,183,050 B2 * 2/2007 Krull .................................. 435/6
7,892,816 B2 * 2/2011 Elliott et al. ................ 435/287.2
2003/0143581 A1 * 7/2003 Franzen et al. ..................... 435/6
2003/0186245 A1 10/2003 Roitman et al.
2006/0148102 A1 * 7/2006 Guo et al. ....................... 436/524
2007/0231796 A1 * 10/2007 Majda ................................ 435/6
2008/0081329 A1 * 4/2008 Elliott et al. ....................... 435/6
2009/0242430 A1 * 10/2009 O'Connor et al. .......... 205/793.5
2010/0108539 A1 * 5/2010 Iwanaga et al. ............... 205/687
2010/0133121 A1 * 6/2010 Arinaga et al. ............... 205/787

FOREIGN PATENT DOCUMENTS

| JP | S53-19527 A | 8/1976 |
|---|---|---|
| JP | 7-107999 A | 4/1995 |
| JP | 2000-323190 | 11/2000 |
| JP | 2001-156321 A | 6/2001 |
| JP | 2001-242081 A | 9/2001 |
| JP | 2002-181777 | 6/2002 |
| JP | 2003-109677 | 4/2003 |
| JP | 2003-249669 A | 9/2003 |

(Continued)

OTHER PUBLICATIONS

Dong et al., Quantitative Photoelectrochemical Detection of Biological Affinity Reaction: Biotin-Avidin Interaction, Anal. Chem. 2004, 76, 499-502, Beijing National Biochip Research and Engineering Center, 18 Life Science Park Road, Changping District, Beijing 102206, China, and Department Of Biological Sciences and Biotechnology, Tsinghua University, Beijing 100084, China, Jan. 15, 2004.

(Continued)

*Primary Examiner* — Bruce Bell
(74) *Attorney, Agent, or Firm* — Carrier Blackman & Associates, P.C.; Joseph P. Carrier; William D. Blackman

(57) ABSTRACT

A method, an electrode, a measuring cell, and a measuring device are disclosed which can detect and quantitatively determine an analyte having specific bonding properties, in a highly sensitive, simple and accurate manner using photocurrent. This method comprises contacting a working electrode and a counter electrode with an electrolyte medium, wherein the working electrode has an analyte immobilized thereon through a probe substance and wherein the analyte is bonded to a sensitizing dye; irradiating the working electrode with light to photoexcite the sensitizing dye; and detecting photocurrent flowing between the working electrode and the counter electrode, wherein the photocurrent is generated by transfer of electrons from the photoexcited sensitizing dye to the working electrode. The working electrode comprises an electron accepting layer comprising an electron accepting substance capable of accepting electrons released from the sensitizing dye in response to photoexcitation, wherein the probe substance is supported on a surface of the electron accepting layer. The electron accepting substance is an oxide semiconductor having an energy level lower than that of a lowest unoccupied molecular orbit (LUMO) of the sensitizing dye. The electrolyte medium comprises an electrolyte and at least one solvent selected from an aprotic solvent and a protic solvent, wherein the electrolyte comprises a salt capable of providing an oxidized sensitizing dye with electrons.

45 Claims, 30 Drawing Sheets

FOREIGN PATENT DOCUMENTS

| | | |
|---|---|---|
| JP | 2004-247105 A | 9/2004 |
| JP | 2005-011609 A | 1/2005 |
| JP | 2005-024286 A | 1/2005 |
| JP | 2005-201795 A | 7/2005 |
| WO | WO 2004/046369 A2 | 6/2004 |
| WO | WO 2004/046721 A1 | 6/2004 |

OTHER PUBLICATIONS

Gao et al., An ultrasensitive photoelectrochemical nucleic acid biosensor, Nucleic Acids Research, 2005, vol. 33, No. 13,, accepted Jul. 18, 2005, published online Aug. 1, 2005, Institute of Bioengineering and Nanotechnology, 31 Biopolis Way, Singapore 138669 and School of Materials, Science and Engineering, Nanyang Technological University, Singapore 639798, Aug. 1, 2005.

Suzuki et al., DNA detection by photoelectric spectral response at dye-sensitized mesoporous electrode, Toin University of Yokohama, Graduate School of Engineering, Yokohama, Kanagawa 225-8502, Jan. 1, 2004.

Tokudome et al., Photoelectrochemical deoxyribonucleic acid sensing on a nanostructured TiO electrode, Applied Physics Letters 87, 213901 (2005), 2005 American Institute of Physics, Research Institute, Toto Ltd, 2-8-1, Honson, Chigasaki-shi, Kanagawa 253-8577 Japan, Nov. 17, 2005.

* cited by examiner

METHOD FOR SPECIFICALLY DETECTING ANALYTE USING PHOTOCURRENT, AND ELECTRODE, MEASURING CELL AND MEASURING DEVICE FOR USE THEREIN

CROSS-REFERENCE TO RELATED APPLICATIONS

The present application is a U.S. National phase of, and claims priority based on PCT/JP2006/319356, filed 28 Sept. 2006, which, in turn, claims priority from Japanese patent application 2005-284817, filed 29 Sep. 2005, and Japanese patent application 2006-103531, filed 04 Apr. 2006. The entire disclosure of each of the referenced priority documents is incorporated herein by reference.

BACKGROUND OF THE INVENTION

1. Field of the Invention

This invention relates to a method for specifically detecting an analyte having specific bonding properties, such as a nucleic acid, an endocrine disruptor and an antigen, using photocurrent. This invention also relates to an electrode, a measuring cell and a measuring device which are used for this method.

2. Background Art

Genetic diagnoses for analyzing DNA in a biological sample are promising as new diagnoses and prevention techniques for various diseases. The following techniques are proposed for simply and accurately conducting such DNA analysis.

A method for analyzing DNA is known in which the analyte DNA is hybridized with a fluorescence-labeled DNA probe having a sequence complementary to that of the analyte DNA, and a fluorescent signal generated in the hybridization is detected (see Japanese Patent Laid-Open Publication No. H7-107999 and Japanese Patent Laid-Open Publication No. H11-315095, for example). The method uses dye fluorescence to detect the double-stranded DNA synthesized by hybridization.

Another method is also known in which, after a gene sample denatured to single-stranded DNA is hybridized with a single-stranded nucleic acid probe complementary to the gene sample, a double-stranded nucleic acid recognizing substance, such as an intercalator, is added thereto for electrochemical detection (see Japanese Patent Publication No. 2573443 and Surface Science Vol. 24, No. 11, pp. 671-676, 2003, for example).

On the other hand, damage to a genital system, a nervous system and the like due to an endocrine disruptor (environmental hormone), such as dioxin, has recently caused a social problem. At present, various methods are employed for detecting the toxicity of the endocrine disrupter, but such substance exhibits the toxicity at a significantly low level of concentration around 10 ppt. Accordingly, it is required to provide a method for detecting an endocrine disruptor within such a low concentration range.

In particular, the endocrine disruptor binds to the target DNA through a protein serving as a receptor or the like, thus affecting the expression of the DNA and the like to cause toxicity. Specifically, the endocrine disruptor does not bind directly to the DNA, but binds indirectly to the DNA through the protein serving as the receptor or the like. For this reason, in a conventional method, such as a prescreening technique using DNA bonding properties, it is not easy to assay the bond.

Incidentally, there is known a solar cell using a sensitizing dye for generating electric energy from light (see Japanese Patent Laid-Open Publication No. H1-220380, for example). The solar cell comprises a polycrystalline metal oxide semiconductor and a sensitizing dye layer deposited on a large area of the surface of the semiconductor.

As an approach to applying the characteristics of the solar cell to biochemical analysis, use of photocurrent generated by photoexciting the sensitizing dye for detecting an analyte (biomolecules such as DNA and protein) has been proposed (see Japanese Patent Laid-Open No. 2002-181777 and "New detection method of DNA double-stranded using photoelectric conversion" by Nakamura, et al. (prepared lecture texts of the Chemical Society of Japan, Vol. $81^{ST}$ No. 2 (2002), page 947), for example).

SUMMARY OF THE INVENTION

The inventors have now found that, in specific detection of an analyte by the use of photocurrent generated by photoexciting a sensitizing dye, it is possible to detect and quantitatively determine an analyte in a highly sensitive, simple and accurate manner by the use of an electrolyte medium which comprises an electrolyte and at least one solvent selected from an aprotic solvent and a protic solvent. The electrolyte comprises a salt capable of providing an oxidized sensitizing dye with electrons.

Accordingly, it is an object of the present invention to provide a method, an electrode, a measuring cell and a measuring device which can detect and quantitatively determine an analyte having specific bonding properties in a highly sensitive, simple and accurate manner by using photocurrent.

According to the present invention, there is provided a method for specifically detecting an analyte, comprising the steps of:

contacting a working electrode and a counter electrode with an electrolyte medium, the working electrode having an analyte immobilized thereon through a probe substance, the analyte being bonded to a sensitizing dye;

irradiating the working electrode with light to photoexcite the sensitizing dye; and detecting photocurrent flowing between the working electrode and the counter electrode, the photocurrent being generated by transfer of electrons from the photoexcited sensitizing dye to the working electrode;

wherein the working electrode comprises an electron accepting layer comprising an electron accepting substance capable of accepting electrons released from the sensitizing dye in response to photoexcitation, the probe substance being supported on a surface of the electron accepting layer;

wherein the electron accepting substance is an oxide semiconductor having an energy level lower than that of a lowest unoccupied molecular orbit (LUMO) of the sensitizing dye; and wherein the electrolyte medium comprises an electrolyte and at least one solvent selected from an aprotic solvent and a protic solvent, the electrolyte comprising a salt capable of providing an oxidized sensitizing dye with electrons.

According to the present invention, there is also provided an electrode for use as a working electrode in the above method, comprising:

a conductive substrate; and an electron accepting layer formed on the conductive substrate, the electron accepting layer comprising an electron accepting substance capable of accepting electrons released from the sensitizing dye in response to photoexcitation.

According to the present invention, there is further provided a measuring cell for use in the above method, comprising:

the above working electrode; and a counter electrode.

According to the present invention, there is furthermore provided a measuring device for use in the above method, comprising:

the above measuring cell;

a light source for irradiating a surface of the working electrode with light; and an ammeter for measuring electric current flowing between the working electrode and the counter electrode.

BRIEF DESCRIPTION OF THE DRAWINGS

FIG. 2A shows a case when the analyte is preliminarily labeled with a sensitizing dye. FIG. 2B shows a case of adding a sensitizing dye capable of intercalating into the double-stranded nucleic acid.

FIG. 10A is a plan view of the working electrode. FIG. 10B is a sectional view of the working electrode. FIG. 10C is a sectional view of another form of the working electrode. FIG. 10D is a sectional view of still another form of the working electrode.

FIG. 11A is a plan view of the working electrode. FIG. 11B is a sectional view of the working electrode. FIG. 11C is a sectional view of another form of the working electrode.

FIG. 14A is an overall perspective view. FIG. 14B is a top view thereof.

FIG. 15A is an overall perspective view. FIG. 15B is a top view thereof.

FIG. 18A is an example of the device with the movable-light-source-type mechanism shown in FIGS. 14A, 14B and 16. FIG. 18B is an example of the device with the movable-cell-function-type mechanism shown in FIGS. 15A, 15B and 17.

FIG. 22A shows a case of using a FTO electrode. FIG. 22B shows a case of using an ITO electrode.

FIG. 24A shows a case of using an electrolytic solution comprising iodine. FIG. 24B shows a case of using an electrolytic solution not comprising iodine.

DETAILED DESCRIPTION OF THE INVENTION

Specific Detection of Analyte Using Photocurrent

In a method according to the present invention, a working electrode and a counter electrode are contacted with an electrolyte medium. The working electrode has an analyte immobilized thereon through a probe substance, while the analyte is bonded to a sensitizing dye. In this state, the working electrode is irradiated with light to photoexcite the sensitizing dye, and photocurrent flowing between the working electrode and the counter electrode is detected. The photocurrent is generated by transfer of electrons from the photoexcited sensitizing dye to the working electrode. The working electrode comprises an electron accepting layer comprising an electron accepting substance capable of accepting electrons released from the sensitizing dye in response to photoexcitation. The probe substance is supported on a surface of the electron accepting layer. The electron accepting substance is an oxide semiconductor having an energy level lower than that of a lowest unoccupied molecular orbit (LUMO) of the sensitizing dye.

Figure 1:
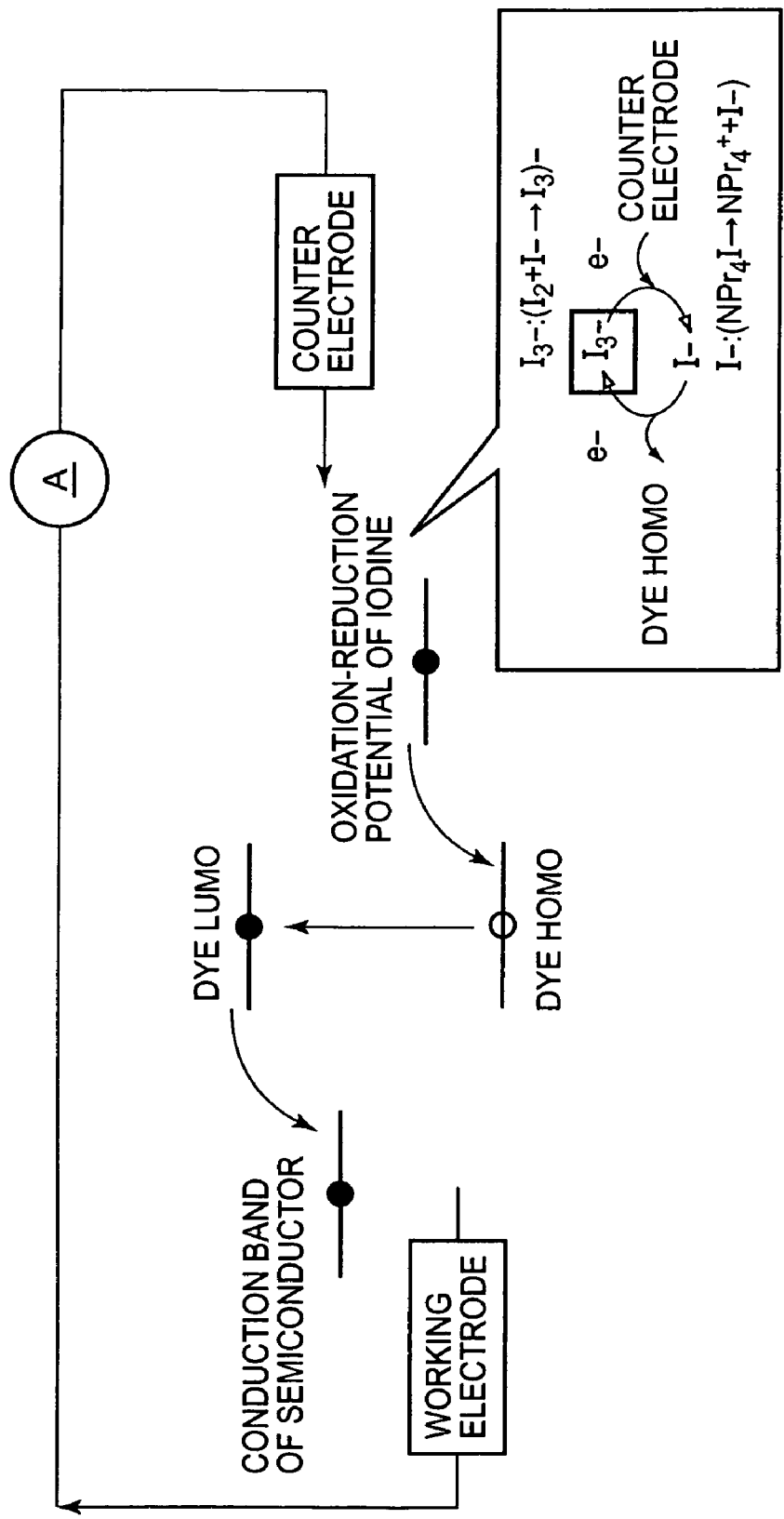
FIG. 1 is a diagram illustrating the principle of a dye sensitized solar cell.

The electrolyte medium comprises an electrolyte and at least one solvent selected from an aprotic solvent and a protic solvent. The electrolyte comprises a salt capable of providing an oxidized sensitizing dye with electrons. The use of such an electrolyte medium leads to a dramatic improvement in the sensitivity and the accuracy of detection of the analyte from the photocurrent as compared with the use of a conventional electrolyte including an electrolyte generally used in a solar cell. The reason is not known exactly, and may be assumed as described below. It should be noted that the following explanation is strictly an assumption and does not limit the present invention at all. FIG. 1 is a diagram for illustrating the principle of a dye sensitized solar cell. A typical composition of an electrolyte medium used in a solar cell is $12/N(C_3H_7)_4I/$ acetonitrile. As shown in FIG. 1, $N(C_3H_7)_4I$ is separated into $N(C_3H_7)_4^+$ and $I^-$ in acetonitrile ($CH_3CN$), and metal $I_2$ combines with the $I^-$ to form $I_3^-$ which then dissolves. The $I_3^-$ produced at this stage is a substance required for repeating an iodine redox cycle to continuously generate electric power in the solar cell. However, this mechanism is thought to reduce the accuracy in detection of the analyte in biochemical analysis. As a result, when an electrolyte, such as commonly used in a solar cell, is used, particularly, when the electrolyte is used to detect SNPs, this requires the detection of subtle difference of current values, which is thought to result in a significant reduction in accuracy. In contrast, the electrolyte medium used in the present invention does not comprise an oxidant for accepting electrons from the counter electrode, such as $I_2$, because of using the electrolyte comprising a salt capable of providing an oxidized sensitizing dye with electrons.

Accordingly, since a component causing a reduction in measurement accuracy, such as $I_3^-$, is not produced, it is thought that the sensitivity and accuracy of detection will be dramatically improved.

The electrolyte medium used in the present invention comprises a salt capable of providing an oxidized sensitizing dye with electrons, at least one solvent selected from an aprotic solvent and a protic solvent, and optionally an additive. That is, the electrolyte used in the present invention comprises a reducing agent for providing an oxidized sensitizing dye with electrons, and does not comprise an oxidant for accepting electrons from the counter electrode. Preferred examples of the electrolyte include iodide and/or bromide not comprising 12 and $Br_2$, specifically, a metal iodide such as LiI, NaI, KI, CsI and $CaI_2$; an iodine salt of a quaternary ammonium compound, such as tetra-alkyl ammonium iodide, pyridinium iodide and imidazolium iodide; metal bromide such as LiBr, NaBr, KBr, CsBr and $CaBr_2$; a bromine salt of a quaternary ammonium compound, such as tetra-alkyl ammonium bromide and pyridinium bromide; metallic complex such as ferrocyanate and ferricynium ions; a thiosulfate, such as sodium thiosulfate, ammonium thiosulfate, potassium thiosulfate and calcium thiosulfate; a sulfite, such as sodium sulfite, potassium sulfite, ammonium sulfite, iron sulfite, sodium hydrogen sulfite and calcium sulfite; and mixtures thereof. More preferred examples of the electrolyte includes LiI; an iodine salt of a quaternary ammonium compound, such as tetra-alkyl ammonium iodide, pyridinium iodide and imidazolium iodide; and mixtures thereof. In particular, LiI or tetra-alkyl ammonium iodide is preferable.

According to a preferred aspect of the present invention, an electrolyte concentration of the electrolyte medium ranges preferably from 0.001M to 15M, more preferably, from 0.01M to 10M.

The solvent used in the present invention is an aprotic solvent, a protic solvent or a mixture thereof. That is, a polar solvent system comprising a mixture of water as a main component and a buffer solution component, or an aprotic polar solvent may be used. Examples of the aprotic polar solvent include nitrites such as acetonitrile; carbonates such as propylene carbonate and ethylene carbonate; a heterocyclic compound such as 1,3-dimethylimidazolinone, 3-methyloxazoline and dialkylimidazolium salt; dimethylformamide; dimethyl sulphoxide; sulfolane; and the like. A plurality of these kinds of solvents may be mixed for use in the electrolyte medium. It is therefore possible to appropriately change the solvent composition in accordance with a target analyte in actual use. For example, in particular, the electrolyte comprises a salt capable of providing an oxidized sensitizing dye with electrons, more specifically, an $I_2$-free iodide compound, while the above aprotic polar solvent is used. This makes it possible to detect a subtle difference in current values with high accuracy and is effective for determining SNP. Also, for protein measurement, a buffer solution is used as the main component together with acetonitrile added thereto in order to retain protein-protein bond and suppress a reduction in the reducing ability of anions, resulting in accurate detection.

According to a preferred aspect of the present invention, the electrolyte medium may be gelatinized (solidified) for use. Examples of the gelatinizing method include techniques such as an addition of a polymer, an addition of an oil gelling agent, polymerization comprising polyfunctional monomers, cross-linking reaction in polymer or the like. Examples of polymers used for the matrix of the gel electrolyte include polyacrylonitrile, polyvinylidene fluoride, and the like.

In the method according to the present invention, first, a sample liquid comprising an analyte, a working electrode and a counter electrode are provided. The working electrode used in the present invention has a surface provided with a probe substance capable of specifically bonding directly or indirectly to an analyte. That is, the probe substance may be not only a substance specifically bonding directly to an analyte, but also a substance capable of specifically bonding to a conjugate resulting from the specific bond of an analyte to a mediator substance such as a receptor protein molecule. Then, the sample liquid is brought into contact with the working electrode under the presence of the sensitizing dye to specifically bond the analyte to the probe substance directly or indirectly. Through this bond, the sensitizing dye is immobilized on the working electrode. The sensitizing dye is a substance capable of releasing electrons toward the working electrode in response to photoexcitation. The analyte or the mediator substance is preliminarily labeled with the sensitizing dye or, in the alternative, the sensitizing dye is simply added to the sample liquid when the sensitizing dye is capable of intercalating into the conjugate of the analyte and the probe substance.

Then, after the working electrode and the counter electrode are brought into contact with the electrolyte medium, the working electrode is irradiated with light to photoexcite the sensitizing dye, thus causing electron transfer from the phothoexcited sensitizing dye to the electron accepting substance. Detecting the photocurrent flowing between the working electrode and the counter electrode resulting from the electron transfer enables the detection of the analyte with high accuracy. Also, the detection current has a strong correlation to the concentration of the test sample in the sample liquid. As a result, quantitative measurement can be made on the test sample on the basis of the measured amount of electric current or the measured electrical quantity.

Analyte and Probe Substance

The analyte used in the method of the present invention is, as long as it has specific bonding properties, not limited and may include one of various types of substances. If such an analyte is used, when a probe substance capable of specifically bonding directly or indirectly to the analyte is supported on the surface of the working electrode, it is possible to detect the analyte by causing it to specifically bind, directly or indirectly, to the probe substance.

In other words, the analyte and the probe substance in the method of the present invention can be selected from various substances which are able to specifically bind to each other. That is, according to a preferred aspect of the present invention, it is preferable to support on the working electrode the analyte which is a substance having specific bonding properties and the probe substance which is a substance specifically bonding to the analyte. This makes it possible to make the analyte specifically bonded to the working electrode, thus detecting the analyte directly. Preferred examples of the combination of the analyte and the probe substance in this aspect include a combination of a single-stranded nucleic acid and a single-stranded nucleic acid complementary to this nucleic acid, and a combination of an antigen and an antibody.

Figure 2A:
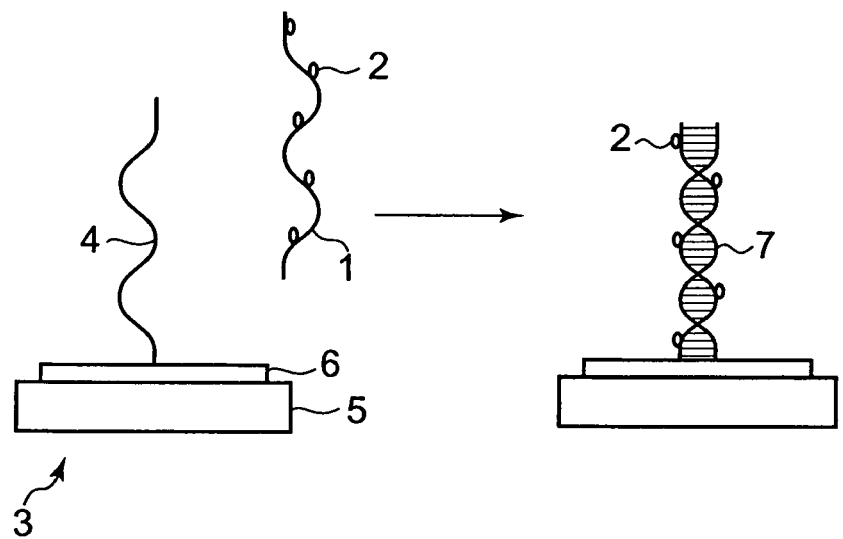
FIGS. 2A and 2B are diagrams illustrating the process of immobilizing an analyte on a probe substance in a case where the analyte is a single-stranded nucleic acid and the probe substance is a single-stranded nucleic acid having properties complementary to the nucleic acid of the analyte.
Figure 2B:
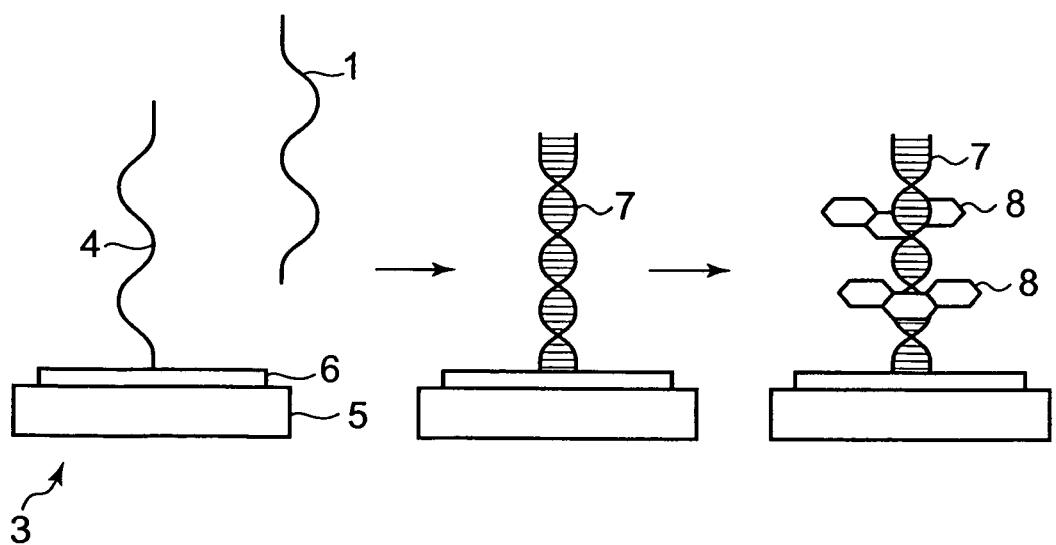

According to a more preferable aspect of the present invention, it is preferable that the analyte is a single-stranded nucleic acid and the probe substance is a single-stranded nucleic acid which is complementary to the nucleic acid of the analyte. FIGS. 2A and 2B illustrate the process of the specific bonding of the analyte to the working electrode in the aspect. As shown in FIGS. 2A and 2B, a single-stranded nucleic acid 1 of the analyte is hybridized with a complementary single-stranded nucleic acid 4 of the probe substance supported on the working electrode 3 to form a double-stranded nucleic acid 7.

In the use of a single-stranded nucleic acid as the analyte, what is required as the single-stranded nucleic acid is to have a portion complementary to the nucleic acid of the probe substance. The length of base pairs of the analyte is not limited, but the probe substance preferably has a complementary portion which is 15 bp or more in view of the nucleic acid. According to the method of the present invention, even when the nucleic acid has a relatively long strand, such as one having the length of base pairs: 200 bp 500 bp and 1000 bp, formation of the specific bond between the nucleic acids of the probe substance and the analyte can be detected with high sensitivity from the photocurrent.

A sample liquid comprising the single-stranded nucleic acid which is the analyte can be produced by using a known method to extract a nucleic acid from various types of analyte samples containing a nuclide acid, which includes blood such as peripheral venous blood, leukocyte, serum, urine, feces, semen, saliva, cultured cells, and tissue cells including various organ cells. In this process, the cells in the analyte sample may be destroyed by, for example, externally applying a physical action such as shaking or an ultrasonic wave to the carrier to produce a vibration thereof. Also, a nucleic-acid extraction solvent may be used to release the nucleic acid from the cell. Examples of the nucleic-acid eluting solution include a surface-active agent such as SDS, Triton-X and Tween-20; saponin; EDTA; protease; and the like. In the use of these solutions to elute the nucleic acid, the reaction can be promoted by incubating the solution at 37° C.

According to a preferred aspect of the present invention, if the content of the gene as the analyte is extremely low, the detection is preferably made after the gene has been amplified by a well-known method. A typical method for amplifying gene would be a method using enzymes such as a polymerase chain reaction (PCR). At this stage, examples of the enzyme used in the gene amplifying method include DNA-dependent DNA polymerase such as DNA polymerase and Taq polymerase; DNA-dependent RNA polymerase such as RNA polymerase I; and RNA-dependent RNA polymerase such as Qβ replicase. A preferable method is the PCR technique using Taq polymerase in view of a point that the amplification can be continuously repeated simply by adjusting the temperature.

According to a preferred aspect of the present invention, it is possible to specifically label the nucleic acid with the sensitizing dye during the above amplifying process. Typically, this is achieved by making DNA capture aminoallyl-modified dUTP. This molecule is captured at the same degree of efficiency as that of unmodified dUTP. In the subsequent coupling stage, the fluorescent dye is activated by N-hydroxysuccinimide, and then reacts specifically with the modified dUTP, resulting in an analyte uniformly labeled with the sensitizing dye.

According to a preferred aspect of the present invention, the preparation of a single-stranded nucleic acid is achieved by first thermally denaturing the crude extract of the nucleic acid obtained in this manner or a purified nucleic-acid solution at a temperature ranging from 90° C. to 98° C., preferably, of 95° C. or higher.

Figure 3:
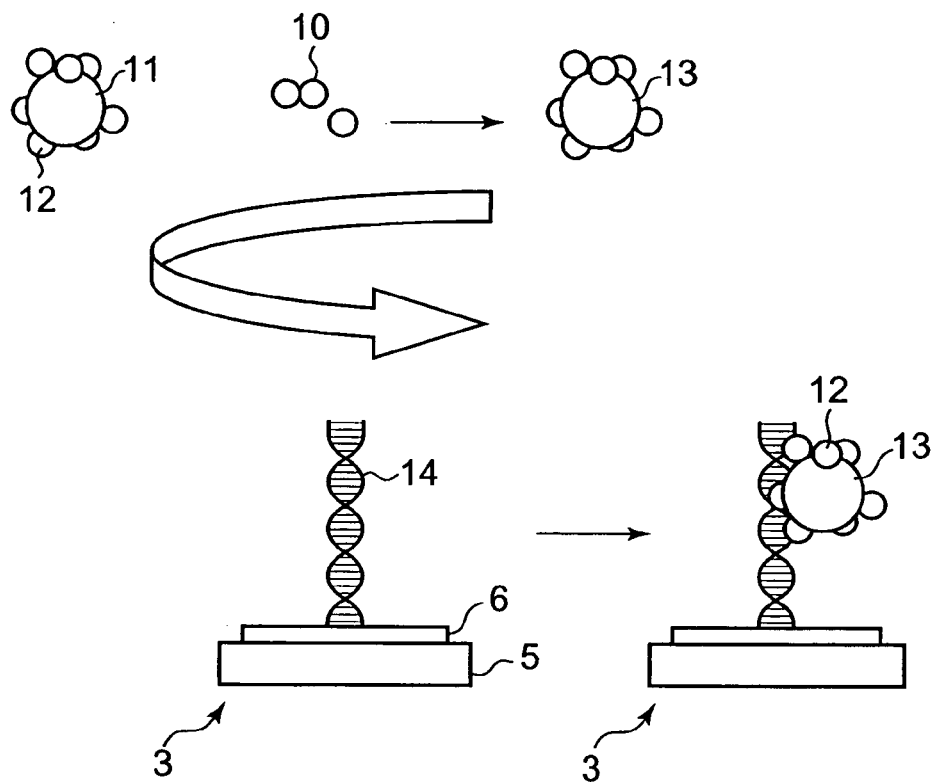
FIG. 3 is a diagram illustrating the process of immobilizing the analyte on the probe substance in a case where the analyte is a ligand, a mediator substance is a receptor protein molecule, and the probe substance is double-stranded nucleic acid.

In the method of the present invention, an analyte and a probe substance may be specifically bonded indirectly to each other. That is, according to a preferred aspect of the present invention, it is preferable that a substance having specific bonding properties is used as an analyte, that a substance specifically bonding to the analyte is coexisted as a mediator substance, and that a substance capable of specifically bonding to the mediator substance is supported as the probe substance on the working electrode. As a result, even if the analyte is a substance which is incapable of specifically bonding to the probe substance, the analyte can be detected by being specifically bonded indirectly via the mediator substance on the working electrode. Preferred examples of the combination of the analyte, the mediator substance and the probe substance in this aspect include a combination of a ligand, a receptor protein molecule capable of receiving the ligand, and a double-stranded nucleic acid capable of specifically bonding to the receptor protein molecule. Preferred examples of the ligand include an endocrine disruptor (environmental hormone). The endocrine disruptor is a substance bonding to DNA via a receptor protein molecule and affecting the gene expression to cause toxicity. However, according to the method of the present invention, it is possible to simply and easily monitor the bonding properties of the protein serving as a receptor or the like to the DNA, which is provided by the analyte. FIG. 3 illustrates the process of the specific bonding of the analyte to the working electrode in this aspect. As shown in FIG. 3, a ligand 10 serving as the analyte first specifically binds to a receptor protein molecule 11 serving as the mediator substance. Then, the receptor protein molecule 13 to which the ligand is bonded specifically binds to a double-stranded nucleic acid 14 serving as the probe substance.

In the method of the present invention, it is possible to make a plurality of identical analytes derived from different sample sources simultaneously react with a single probe substance and to determine the difference between the amounts of the analytes resulting from the derivations of the samples. This enables quantitative determination of the analyte derived from the target sample source. A specific example of application includes an expression profile analysis using competitive hybridization on a micro array. In this example, for the analysis of a difference in an expression pattern of a particular gene between cells, analytes individually labeled with different fluorescent dyes are competitively hybridized with the same probe substance. The present invention, by using such a technique, can provide an advantage of electrochemically analyzing an expression difference between cells, which cannot be achieved by the conventional technique.

Sensitizing Dye

According to the method of the present invention, for the detection of the presence of an analyte by using photocurrent, an analyte is specifically bonded directly or indirectly to a probe substance under the coexistence of a sensitizing dye. By this bond, the sensitizing dye is immobilized onto the working electrode. For this purpose, in the method of the present invention, the analyte 1 or the mediator substance 11 can be preliminarily labeled with sensitizing dyes 2, 12 as shown in FIG. 2A and FIG. 3. Also, in a case of using a sensitizing dye 8 which is capable of intercalating into the combined element 7 of the analyte and the probe substance as shown in FIG. 2B (e.g., a double-stranded nucleic acid after the hybridization), the sensitizing dye can be immobilized onto the probe substance by adding the sensitizing dye to the sample liquid.

According to a preferred aspect of the present invention, when the analyte is a single-stranded nucleic acid, one sensitizing-dye label is preferably attached to each molecule of the analyte. From the viewpoint of facilitating the specific bonding between the analyte and the probe substance, the labeled position in the single-stranded nucleic acid is preferably either the 5"-end or the 3'-end of the single-stranded nucleic acid, and more preferably the 5'-end of the analyte from the viewpoint of greater simplification of the labeling process.

According to another preferred aspect of the present invention, for increasing the amount of sensitizing dye carried per molecule of the analyte, two or more sensitizing-dye labels are preferably attached to each molecule of the analyte. As a result, it is possible to further increase the amount of dye carried per unit surface area in the working electrode on which the electron accepting substance is provided, enabling observation of a photocurrent response with higher sensitivity.

The sensitizing dye employed in the present invention is required to be a substance capable of releasing electrons toward the working electrode in response to photoexcitation, of inducing a transition to the photoexcited state by the light irradiation from the light source, and also of changing from the photoexcited state to the electron state of electron injection to the working electrode. In consequence, the sensitizing dye used may have the above electron state with the working electrode, particularly with the electron accepting layer, making it possible to use various types of sensitizing dyes and to eliminate the need of using an expensive dye.

From the aspect of individual detection of a plurality of analytes, the sensitizing dyes with which the respective analytes are labeled may be excited by light differing in wavelength from each other, for example, the analytes being required to be individually excited by selecting one wavelength of the irradiated light. For example, when a plurality of sensitizing dyes corresponding to a plurality of analytes are used and the light irradiated varies in exciting wavelengths for each sensitizing dye, even if a plurality of probes are located on the same spot, the signals can be detected individually. In the method of the present invention, the number of analytes is not limited, but, considering the wavelength of light irradiated from the light source and the absorption properties of the sensitizing dye, 1 to 5 kinds of the analytes may be appropriate. A sensitizing dye usable in the aspect may be only photoexcitable within the wavelength range of the irradiated light, and the absorption maximum is not necessarily required to be within the wavelength range. In this connection, the presence/absence of the light absorbing reaction of the sensitizing dye in a certain wavelength can be measured by use of an ultraviolet-visible spectrophotometer (e.g., UV-3150 produced by Shimadzu Company).

Specific examples of the sensitizing dye include a metal complex and an organic dye. Preferred examples of the metal complex include a metal phthalocyanine such as copper phthalocyanine and titanyl phthalocyanine; chlorophyll or its derivative; and complexes of hemin, ruthenium described in Japanese Patent Laid-Open Publication No. H1-220380 and Japanese Patent Laid-Open Publication No. H5-504023, osmium, iron and zinc (e.g., cis-dicyanate-bis(2,2'-bipyridyl-4,4'-dicarboxylate)ruthenium (II)). Preferred examples of the organic dye include metal-free phthalocyanine, 9-phenylxanthene dye, cyanine dye, metallocyanine dye, xanthene dye, triphenylmethane dye, acridine dye, oxazine dye, coumarin dye, merocyanine dye, rhodacyanine dye, polymethine dye, indigo dye and the like. Other preferred examples of the sensitizing dye include Cy3, Cy3.5, Cy5, Cy5.5, Cy7, Cy7.5 and Cy9 which are produced by Amersham Biosciences Company; AlexaFluor355, AlexaFluor405, AlexaFluor430, AlexaFluor488, AlexaFluor532, AlexaFluor546, AlexaFluor555, AlexaFluor568, AlexaFluor594, AlexaFluor633, AlexaFluor647, AlexaFluor660, AlexaFluor680, AlexaFluor700 and AlexaFluor750 which are produced by Molecular Probe Company; and DY-610, DY-615, DY-630, DY-631, DY-633, DY-635, DY-636, EVOblue10, EVOblue30, DY-647, DY-650, DY-651, DYQ-660 and DYQ-661 which are produced by Dyomics Company.

Preferred examples of the sensitizing dye capable of intercalating into a double-stranded nucleic acid include acridine orange and ethidium bromide. In the use of such a sensitizing dye, simply by adding the sensitizing dye to the sample liquid after hybridization, a double-stranded nucleic acid labeled with the sensitizing dye is formed, which therefore, eliminates the need for preliminarily labeling a single-stranded nucleic acid.

Working Electrode and Manufacturing Thereof

The working electrode employed in the present invention is an electrode having a surface on which the probe substance is provided, which is capable of accepting electrons released from the sensitizing dye immobilized via the probe substance in response to photoexcitation. Accordingly, the configuration and the materials of the working electrode are not limited as long as the electron transition occurs between the working electrode and the sensitizing dye used, and various configurations and various materials may be employed.

According to a preferred aspect of the present invention, it is preferable that the working electrode comprises an electron accepting layer comprising an electron accepting substance capable of accepting the electrons released from the sensitizing dye in response to photoexcitation, and the probe substance is provided on the surface of the electron accepting layer. Also, according to a more preferred aspect of the present invention, it is preferable that the working electrode further comprises a conductive substrate, and the electron accepting layer is formed on the conductive substrate. The electrode in this aspect is illustrated in FIG. 2 and FIG. 3. The working electrode 3 illustrated in FIG. 2 and FIG. 3 comprises a conductive substrate 5, and an electron accepting layer 6 formed on the conductive substrate 5 and comprising an electron accepting substance. A probe substance 4 is supported on the surface of the electron accepting layer 6.

The electron accepting layer 6 in the present invention comprises an electron accepting substance capable of accepting the electrons released from the sensitizing dye immobilized through the probe substance 4 in response to photoexcitation. In other words, the electron accepting substance may be a substance capable of having an energy level at which electrons can be injected from the labeling dye when photoexcited. In this case, the energy level (A) at which electrons can be injected from the photoexcited labeling dye means a conduction band (CB) when a semiconductor is used as an electron accepting material, for example. That is, the electron accepting substance employed in the present invention may have a level A that is lower than the energy level of the LUMO of the sensitizing dye.

Examples of the electron accepting substance include an elemental semiconductor such as silicon and germanium; an oxide semiconductor of titanium, tin, zinc, iron, tungsten, zirconium, hafnium, strontium, indium, cerium, yttrium, lanthanum, vanadium, niobium or tantalum; a perovskite semiconductor such as strontium titanate, calcium titanate, sodium titanate, barium titanate and potassium niobate; sulfide semiconductor of cadmium, zinc, lead, silver or stibium, bismuth; selenide semiconductor of cadmium or lead; a telluride semiconductor of cadmium; a phosphide semiconductor of zinc, gallium, indium or cadmium; and a compound semiconductor such as gallium arsenide, copper-indium-selenide and copper-indium-sulfide. It should be noted that the above-described semiconductors may be either an intrinsic semiconductor or an impurity semiconductor.

According to a preferred aspect of the present invention, an oxide semiconductor is employed as the electron accepting substance. More preferably, $TiO_2$, ZnO, $SnO_2$, $Fe_2O_3$, $WO_3$, $Nb_2O_5$, $Ta_2O_3$, $In_2O_3$, and strontium titanate may be employed. Most preferably, $TiO_2$, indium-tin composite oxide (ITO) or fluorine-doped tin oxide (FTO) may be used. Since ITO and FTO have a function as a conductive substrate as well as the electron accepting layer, the use of these materials allows the electron accepting layer alone to function as the working electrode without the conductive substrate.

When a semiconductor is used as the electron accepting substance, the semiconductor may be either a single crystal or polycrystal, but preferably is a polycrystal, and more preferably, a polycrystal having porosity rather than density. By the use of this, the specific surface area is increased, resulting in the mass adsorption of the analyte and the sensitizing dye so as to detect the analyte with higher sensitivity. In consequence, according to a preferred aspect of the present invention, the electron accepting layer has porosity with a diameter of each hole ranging preferably from 3 nm to 1000 nm, more preferably from 10 nm to 100 nm.

According to a preferred aspect of the present invention, the surface area of the electron accepting layer located on the conductive substrate is preferably ten or more times, more preferably 100 or more times that of the projected area. The upper limit of the surface area is not specially limited, but will be typically on the order of 1000 times. A particle diameter of fine particles of the electron accepting substance forming the electron accepting layer has an average particle diameter when the projected area is converted into a circle ranging preferably from 5 nm to 200 nm, more preferably from 8 nm to 100 nm, and furthermore preferably from 20 nm to 60 nm, as the primary particles. An average particle diameter of the fine particles (secondary particles) of the electron accepting substance in the dispersion ranges preferably from 0.01 μm to 100 μm. For the purpose of scattering the incoming light to improve the light capturing rate, the electron accepting layer may be formed by the additional use of fine particles of the electron accepting substance having a greater particle diameter of approximately 300 nm, for example.

The irregular surface structure increases the surface area of the electron accepting layer 6 for the immobilization of a larger number of probe molecules so as to make it possible to increase the detection sensitivity. Since the size of a biomolecule ranges from approximately 0.1 nm to 20 nm, a preferable diameter of pores created by the irregular surface structure ranges from 20 nm or more to 150 nm or less. If an entry port to a space created by the irregular surface structure is equal to or less than the above diameter, the specific surface area increases but the bond between the biomolecule and the probe is not made, resulting in a reduction in intensity of a detected signal. If a distance between the irregular is large, the surface area does not so much increase, resulting in a less increase in signal intensity. A more preferable range suitable for sensing the biomolecule is from 50 nm or more to 150 nm or less.

According to a preferred aspect of the present invention, a pillar structure is preferably employed as the convexity structure in which nanoscale pillars are regularly arranged on the surface. Various methods for constructing the pillar structure are known. A method of using an anodized alumina template with nanoscale holes is typical. One method is to perform etching to remove an alumina template after a ceramic sol has been filled into the template and then thermally treated, and another method is to perform thermal treatment after the filled ceramic sol has been removed from the template. Examples of the method of manufacturing the pillar-shaped nanostructure include a method, disclosed in Japanese Patent Laid-Open Publication No. 2004-130171, in which a nanostructure is produced on a transparent substrate and a transparent conductive layer. In the method employed here, a titania sol is filled into an anodic alumina template, then is thermally treated at 300° C. to 400° C., and the template is then removed by etching. As a result, titania nanotubes and titania nanowires are produced as a nanostructure.

According to a preferred aspect of the present invention, voids are preferably employed for the concavity structure, which are created because of a gas phase resulting from oxidative destruction of organic matter caused by calcining an inorganic-organic hybrid precursor comprising a ceramic component. In the inorganic-organic hybrid precursor, a metal-oxygen network structure produced by the oxidation of an organometallic compound (metal alkoxide) and polycondensation reaction occurring subsequent to this oxidation, an organic polymer and the like coexist together. In addition, another method is for an organic polymer and/or the like to be added to commercially available titanium oxide particles (e.g., anatase crystal, AMT-600 (trade name) (average particle diameter of 30 nm) produced by Tayca Company) or a titanium oxide dispersion. Various suggestions have been made for these compositions. For example, Japanese Patent Laid-Open Publication No. H10-212120 proposes a composition in which titanium oxide particles are dispersed into a glyme based solvent (HO—(—$CH_2CH_2O$—)$_n$—R, where n is 1 to 10, R is an alkyl group or aryl group) and an organic polymer is added as a dispersing agent. A coating of the fluid dispersion of this composition is applied to a support by an appropriate method (dip coating, spray coating, spinner coating, blade coating, roller coating, wiper bar coating or reverse roll coating), and is then calcined at 200° C. to 800° C. In this case, a specific surface area of 40 $cm^2$ to 50 $cm^2$ per $cm^2$ (1m thick) is formed. Also, in Japanese Patent Laid-Open Publication No. 2001-233615, a sol solution of tetraalkoxy titan, and ethylene oxide, propylene oxide, ethylene oxide block copolymer, as well as a stabilizer and a solvent is dripped on the substrate, and then the solvent is vaporized by rotating the substrate at high speeds to turn into a gel in order to obtain an organic-inorganic composite titania thin-film with a three-dimensional structure which is then calcined at high temperatures to remove the block copolymer, thus forming a fine three-dimensional concavity structure. In addition, a method using oligosaccharide (trehalose) as an organic polymer is disclosed (Japanese Patent Laid-Open Publication No. 2004-83376), by which a ceramic porous film with a porosity of 38% to 56% is obtained.

In this manner, various methods for controlling a fine ceramic irregular surface structure are proposed. When these methods are applied to a ceramic electrode material suitable for this technique, it is possible to create and manufacture an electrode material with a large specific surface area.

According to a preferred aspect of the present invention, it is preferable that the working electrode further comprises a conductive substrate, and the electron accepting layer is provided on the conductive substrate. A conductive substrate suitable for use in the present invention may be not only one having a support which itself has conductivity as in the case of a metal such as titan, but also one having a conductive layer provided on the surface of a glass or plastic support. When a conductive substrate having a conductive layer is used, the electron accepting layer is formed on the conductive layer. Examples of conductive materials forming the conductive layer include metal such as platinum, gold, silver, copper, aluminum, rhodium and indium; conductive ceramics such as carbon, carbide and nitride; and conductive metallic oxide such as indium-tin composite oxide, fluorine-doped tin oxide, antimony-doped tin oxide, gallium-doped zinc oxide and aluminum-doped zinc oxide, preferably, indium-tin composite oxide (ITO) and fluorine-doped tin oxide as the metal oxide (FTO). However, as described earlier, when the electron accepting layer itself functions as a conductive substrate, the conductive substrate may be omitted. Also, in the present invention, the conductive substrate is not limited as long as the material can provide conductivity, and includes a thin-film-form or spot-shaped conductive layer without having in itself the strength required as a support.

According to a preferred aspect of the present invention, the conductive substrate is substantially transparent and more specifically, has preferably a light transmittance of 10% or more, preferably 50% or more, furthermore preferably 70% or more. This makes it possible to configure a cell such that light is irradiated from the back side (i.e., a conductive substrate) of the working electrode and the light traveling through the working electrode (i.e., the conductive substrate and the electron accepting layer) excites the sensitizing dye. Also, according to a preferred aspect of the present invention, the conductive substrate has preferably a thickness of the order of 0.02 μm to 10 μm. Also, according to a preferred aspect of the present invention, the conductive substrate has preferably an electrical surface resistance of 100 or less $\Omega/cm^2$, more preferably, of 40 or less $\Omega/cm^2$. The lower limit of the surface resistance of the conductive substrate is not specially limited, but will be typically approximately 0.1 $\Omega/cm^2$.

Examples of the preferred method of providing the electron accepting layer on the conductive substrate include a method in which a conductive support is coated with a fluid dispersion or colloid solution of the electron accepting substance; a method in which a coating of a precursor to semiconductor fine-particles is applied to an conductive support, and then is hydrolyzed by the moisture in the air to obtain a fine-particle film (sol-gel process); sputtering; CVD; PVD; and vapor-deposition techniques. Examples of the method of producing the fluid dispersion of semiconductor fine-particles as the electron accepting substance include the above-described sol-gel process, a method in which the particles are ground in a mortar; a method in which the particles are dispersed while being crushed using a mill; or a method in which the particles are precipitated during synthesis of a semiconductor to be used as they are. Examples of the dispersion medium used in this method comprise water and various organic solvents (e.g., methanol, ethanol, isopropyl alcohol, dichloromethane, acetone, acetonitrile, ethyl acetate and the like). In the dispersing process, if necessary, a polymer, surfactant, acid, chelating agent or the like may be used as a dispersing aid.

Preferred examples of the method of applying a coating of the fluid dispersion or colloid solution of the electron accepting substance include roller coating and dipping coating in the application system; air-knife coating and blade coating in the metering system; and, in the system using application and metering to coat the same part, wire-bar coating disclosed in Japanese Patent Publication No. S58-4589, slide hopper coating, extrusion coating, curtain coating, spin coating and spray coating described in U.S. Pat. No. 2,681,294, U.S. Pat. No. 2,761,419, U.S. Pat. No. 2,761,791 and the like.

According to a preferred aspect of the present invention, when the electron accepting layer comprises semiconductor fine-particles, the film thickness of the electron accepting layer is preferably from 0.1 μm to 200 μm, more preferably from 0.1 μm to 100 μm, furthermore preferably from 1 μm to 30 μm, most preferably from 2 μm to 25 μm. In this way, it is possible to increase the amounts of the probe substance and the sensitizing dye immobilized thereon per unit project area to increase the amount of photocurrent flow and also to reduce the loss of electrons generated by charge recombination. Also, the coating amount of the semiconductor fine-particles per $m^2$ on the conductive substrate is preferably from 0.5 g to 400 g, more preferably from 5 g to 100 g.

According to a preferred aspect of the present invention, when the electron accepting substance comprises indium-tin composite oxide (ITO) or fluorine-doped tin oxide as the metal oxide (FTO), the film thickness of the electron accepting layer is preferably 1 nm or more, more preferably from 10 nm to 1 µm.

According to a preferred aspect of the present invention, the heating treatment is preferably performed after the conductive substrate is coated with the semiconductor fine-particles. As a result, the particles come into electrical contact with each other, and an improvement in coating strength and an improvement in adhesion properties to the support can be achieved. The temperature of the heating treatment is preferably from 40° C. to 700° C., more preferably from 100° C. to 600° C. A preferable time period of the heating treatment is from approximately 10 minutes to approximately 10 hours.

According to another preferred aspect of the present invention, when the conductive substrate used has a low melting point or softening point such as a polymer film, for the purpose of preventing heat deterioration, the film is preferably formed by a method not using heat-temperature treatment. Examples of such a method for forming a film include pressing, low-temperature heating, electron-beam irradiation, microwave irradiation, electrophoresis, sputtering, CVD, PVD, vapor deposition, and the like.

The probe substance is supported on the surface of the electron accepting layer of the working electrode thus produced. The probe substance may be supported on the working electrode in accordance with well-known methods. According to a preferred aspect of the present invention, in the case of using a single-stranded nucleic acid as the probe substance, an oxidized layer is formed on the surface of the working electrode, and then the nucleic-acid probe and the working electrode are combined with the oxidized layer in between. At this point, the immobilization of the nucleic-acid probe on the working electrode can be achieved by introducing a functional group to an end of the nucleic acid. As a result, the nucleic-acid probe to which the functional group is introduced can be immobilized on a carrier by the immobilization reaction without change. The introduction of the functional group to the nucleic acid end can be achieved by use of an enzyme reaction or a DNA synthesizer. Examples of enzymes used in the enzyme reaction include terminal deoxynucleotidyl transferase, poly(A)polymerase, polynucleotide kinase, DNA polymerase, polynucleotide adenyltransferase and RNA ligase. Also, the functional group can be introduced by polymerase chain reaction (PCR technique), nick translation or random primer technique. The functional group may be introduced to any part of the nucleic acid, which includes a 3'-end, a 5'-end or a random position.

According to a preferred aspect of the present invention, as the functional group for immobilizing the nucleic-acid probe on the working electrode, amine, carboxylic acid, sulfonic acid, thiol, hydroxyl group, phosphoric acid, and the like can be preferably used. In addition, according to a preferred aspect of the present invention, it is possible to use a material for forming cross-link between the working electrode and the nucleic-acid probe to tightly immobilize the nucleic-acid probe on the working electrode. Preferred examples of such cross-link materials include a silane coupling agent, a titanate coupling agent and a conductive polymer such as polythiophene, polyacetylene, polypyrole and polyaniline.

According to a preferred aspect of the present invention, it is possible to use a simpler operation, so-called physical adsorption, to efficiently immobilize the nucleic-acid probe.

The physical adsorption of the nucleic-acid probe to the electrode surface is carried out in the following manner, for example.

First, the electrode surface is cleaned with distilled water and alcohol using an ultrasonic cleaner. Then, the electrode is inserted into a buffer solution containing a nucleic-acid probe to cause the nucleic-acid probe to be adsorbed onto the surface of the carrier.

In addition, after the adsorption of the nucleic-acid probe, a blocking agent is added in order to suppress nonspecific adsorption. A blocking agent which can be used for this purpose is not limited, provided that it is a substance capable of blocking a site of the electron accepting layer surface which does not adsorb the nucleic-acid probe and of being adsorbed to the electron accepting substance by chemical adsorption, physical adsorption or the like, but the blocking agent is preferably a substance having a functional group which can be adsorbed through chemical bond. For example, preferred examples of the blocking agent when titanium oxide is used as the electron accepting layer include a substance having a functional group adsorbable to titanium oxide, such as a carboxylic acid group, phosphoric acid group, sulfonic acid group, hydroxyl group, amino group, pyridyl group, amide and the like.

According to a preferred aspect of the present invention, it is preferred that the probe substance is separately supported on each of a plurality of regions isolated from each other on the working electrode, for each region to be individually irradiated with light from the light source. This makes it possible to measure a plurality of samples on a single working electrode, enabling integration of a DNA chip and the like. According to a more preferred aspect of the present invention, the working electrode is patterned with a plurality of mutually isolated regions on which the probe substance is supported, and preferably during the scanning of the light irradiated from the light source, the detection and quantitative determination of the analytes are continuously performed on the samples in the respective regions by a single operating action.

According to a more preferred aspect of the present invention, a plurality of the kinds of probe substances may be supported on each of the plurality of the regions isolated from each other on the working electrode. This makes it possible to simultaneously measure a large number of samples, equal to the number made by multiplying the number of regions by the number of kinds of probe substances in each region.

According to a more preferred aspect of the present invention, different probe substances may be supported in each region of the plurality of the regions isolated from each other on the working electrode. Since this makes it possible to support the number of kinds of probe substances corresponding to the number of isolated regions, a simultaneous measurement can be made on a large number of kinds of analytes. This aspect can be preferably used for multiplex analysis of single nucleotide polymorphisms (SNPs) since an analysis of the analyte differing in each region is possible to conduct.

Counter Electrode

The choice of a counter electrode employed in the present invention is not specially limited, provided that an electric current flowing between the counter electrode and the working electrode when the counter electrode contacts with an electrolyte medium, and one made by evaporating metal or conductive oxide onto an electrical insulating support such as glass, plastic and ceramics can be used. In addition, a technique of vapor deposition, sputtering or the like can be used to deposit the metal thin-film serving as the counter electrode such that the metal thin-film has a thickness of 5 µm or less, preferably ranging from 3 nm to 3 µm. Preferable examples of materials which can be employed for the counter electrode include a conductive polymer such as platinum, gold, palladium, nickel, carbon and polythiophene; conductive ceramics such as oxide, carbide and nitride, more preferably, platinum and carbon, most preferably, platinum. These materials are capable of forming a thin film by the same methods as those for the electron accepting layer.

Method and Device for Measurement

In the method of the present invention, the sample liquid is brought into contact with the working electrode under the presence of the sensitizing dye to specifically bind the analyte directly or indirectly to the probe substance. By this bond, the sensitizing dye is immobilized on the working electrode. In this process, the buffer solution of the present invention, which will be described later, is used as a solvent of the sample liquid, thereby improving the sensitivity when the working electrode detects the analyte.

According to a preferred aspect of the present invention, when a single-stranded nucleic acid preliminarily labeled with the sensitizing dye is an analyte, it is possible to initiate hybridization reaction between the single-stranded nucleic acid and another single-stranded nucleic acid which is a probe substance. A preferable temperature for the hybridization reaction ranges from 37° C. to 72° C., but the optimum temperature differs according to the length of the base sequence of the probe used and the like.

According to another preferred aspect of the present invention, in the case of using a sensitizing dye capable of intercalating into a conjugate of the analyte and the probe substance (e.g., a double-stranded nucleic acid after hybridization), the addition of the sensitizing dye to the sample liquid enables the conjugate to be labeled specifically with the sensitizing dye.

According to a preferred aspect of the present invention, it is preferable that by cleaning with a cleaning fluid the working electrode having the analyte specifically bonded directly or indirectly to the probe substance, the analyte not bonded to the working electrode is removed. The cleaning fluid used in this case may further comprise a surfactant.

In the method of the present invention, the working electrode on which the analyte and the sensitizing dye is immobilized is brought into contact with an electrolyte medium together with the counter electrode, and the working electrode is irradiated with light to photoexcite the sensitizing dye. Detection is then conducted for the photocurrent flowing between the working electrode and the counter electrode which results from the electron transfer from the photoexcited sensitizing dye to the working electrode. The relatively positional relationship of the working electrode and the counter electrode is not limited, provided that the working electrode and the counter electrode do not electrically short to each other and are in contact with an electrolyte medium. The working electrode and the counter electrode may be disposed to face each other or disposed at a distance from each other in the same plane. It should be noted that, when the working electrode and the counter electrode are disposed at a distance from each other in the same plane, both the electrodes are preferably provided on an electrical-insulating substrate in order to prevent an electrical short circuit between the working electrode and the counter electrode.

Figure 4:
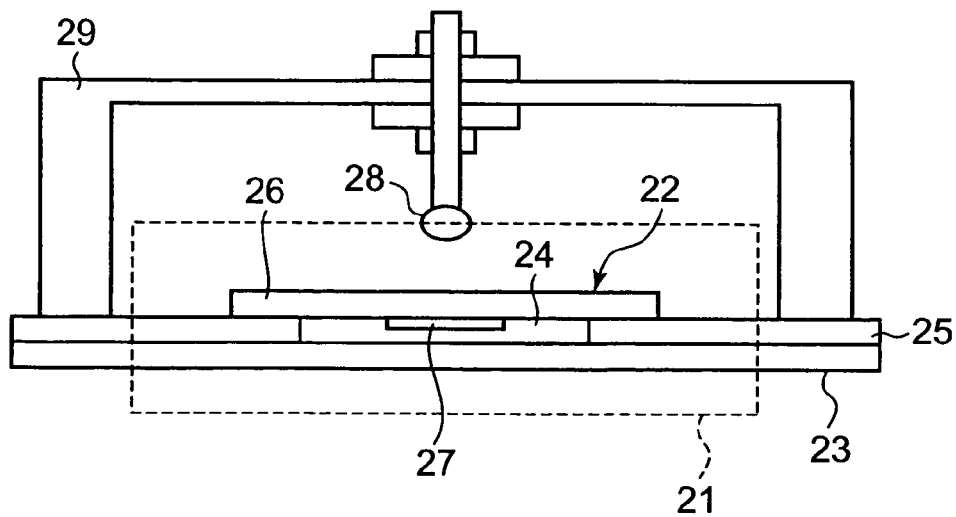
FIG. 4 is a diagram illustrating a measuring cell in which a light source is disposed and which is a part 21 surrounded by the dotted line.
Figure 5:
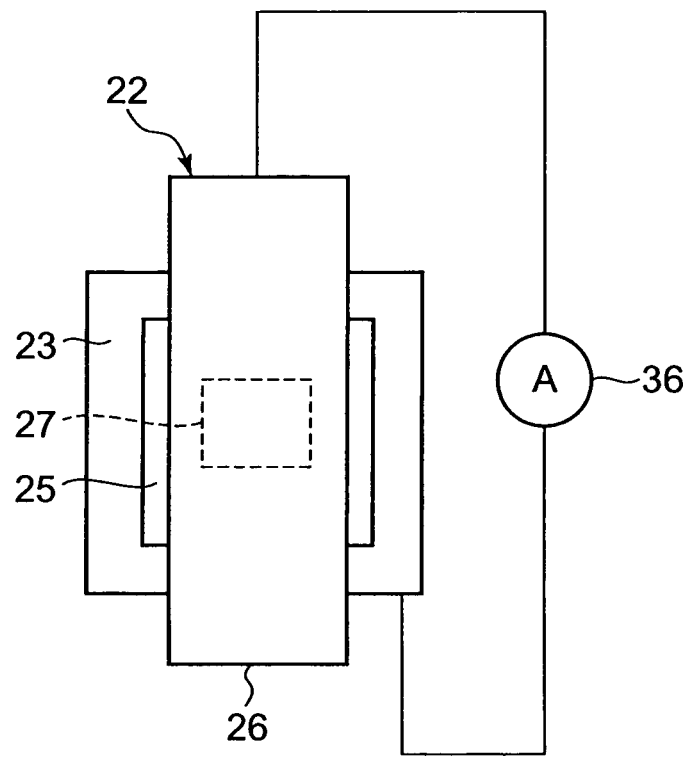
FIG. 5 is a plan view of the measuring cell shown in FIG. 4.

An example of such a measuring cell is illustrated in FIG. 4 and FIG. 5. The measuring cell 21 shown in FIG. 4 and FIG. 5 has a space 24 created between a working electrode 22 and a counter electrode 23 and filled with an electrolytic solution. The working electrode 22 comprises a conductive substrate 26 and an electron accepting layer 27, and is positioned such that the electron accepting layer 27 is in contact with the electrolyte solution. An electrical-insulating spacer 25 is inserted between the working electrode 22 and the counter electrode 23 in order to provide the space 24 for containing the electrolyte solution. A shorter distance between the electrodes is preferable for the purpose of efficiently initiating the oxidation reduction cycle, and a distance of tens of µm is preferable in view of the necessary accuracy in the fabricating process. Also, if a manufacturing method such as MEMS is used, a shorter distance between the electrodes can be made.

A light source 28 is disposed above the working electrode 22 with a light-source cover 29 in between. In other words, the cell is configured such that the back side of the working electrode 22 (i.e., from the conductive substrate) is irradiated with light, and then the light traveling through the working electrode (i.e., the conductive substrate and the electron accepting layer) excites the sensitizing dye. However, needless to say, the back side of the counter electrode may be irradiated with light by using translucent materials to form the counter electrode, or the working electrode and the counter electrode may be irradiated with light parallel to these electrodes. The light source employed in the present invention is not limited, provided that the light source is capable of emitting light of a wavelength that is able to photoexcite the labeling dye, and preferable examples include a fluorescent tube, a blacklight, a germicidal lamp, an incandescent lamp, a low-pressure mercury lamp, a high-pressure mercury lamp, an xenon lamp, a mercury-xenon lamp, a halogen lamp, a metal halide lamp, an LED (white, blue, green, red), a laser ($CO_2$ laser, dye laser, semiconductor laser), and sunlight, more preferably, a fluorescent tube, an incandescent lamp, an xenon lamp, a halogen lamp, a metal halide lamp, an LED (white, blue, green, red), sunlight, and the like. Also, if necessary, a spectrograph or a band-pass filter may be used to emit only light of a specific wavelength region for irradiation.

Figure 6:
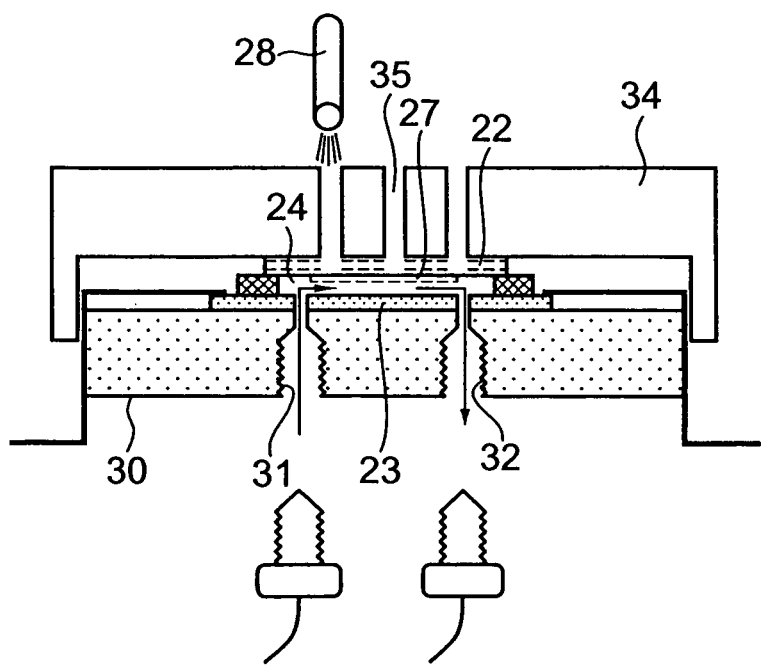
FIG. 6 is a sectional view of another example of the measuring cell.
Figure 7:
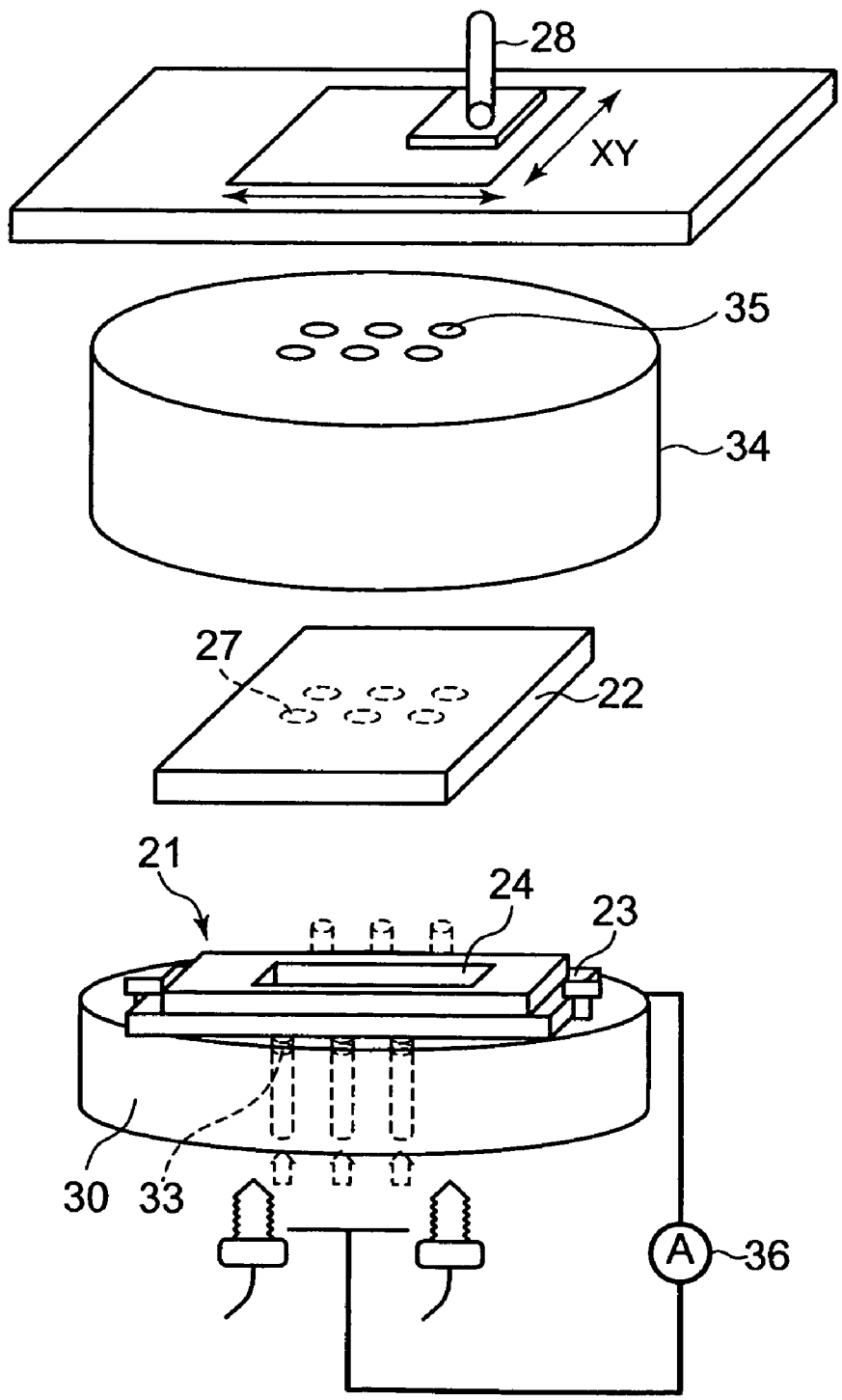
FIG. 7 is an exploded perspective view of the measuring cell shown in FIG. 6.

FIG. 6 is a sectional view of an example of another measuring cell and FIG. 7 is an exploded perspective view of the measuring cell. A counter electrode 23 is provided on a substrate 30. A feed orifice 31 and a discharge orifice 32 are formed for the electrolyte solution or the cleaning fluid in the substrate 30. The insulating spacer 25 having the space 24 for containing the electrolyte solution is disposed on the counter electrode 23. The counter electrode 22 is provided on the insulating spacer 25. A plurality of electron accepting layers 27 are arranged at intervals from each other on the face of the working electrode 22 facing the space 24.

Working-electrode contacts 33 extend through the substrate 30 in such a manner as to prevent interference with the counter electrode 23. The working-electrode contacts 33 are electrically connected with the electrode by using the probes bonded to the electron accepting layer 27 as electric contacts.

A retainer member 34 is provided over the working electrode 22, and has through-holes 35 formed in positions respectively corresponding to the plurality of the electron accepting layers 27. The working electrode 22 is irradiated with the light from the light source 28 through the through-hole 35. An electric-current meter 36 is connected between the working electrode 22 and the counter electrode 23, so that the electric-current meter 36 measures the photocurrent flowing through the system by the light irradiation.

According to a preferred aspect of the present invention, when two or more kinds of sensitizing dyes which are capable of being respectively excited by different wavelengths are used to detect a plurality of kinds of analytes, the irradiation with light of a specific wavelength though a wavelength selecting means from the light source makes it possible to excite individually the plurality of dyes. Examples of the wavelength selecting means used include a spectroscope, a colored glass filter, an interference filter, a band-pass filter and the like. It is possible to use a plurality of light sources which are capable of emitting light of different wavelengths depending on the kinds of sensitizing dyes. Examples of a preferable light source in this case include an LED or laser light for emitting light of a specific wavelength. For the purpose of efficiently irradiating the working electrode with light, a quartz, glass or liquid light guide may be used to guide the light.

According to a preferred aspect of the present invention, the light emitted from the light source preferably originally contain substantially no ultraviolet ray or, in the alternative, the light is preferably emitted from the light source through means for removing ultraviolet ray. Thereby, it is possible to make measurements with increased accuracy by effectively suppressing the background electric-current, that is, noises, caused by the photoexcitation of the electron accepting substance itself which may possibly be produced when the irradiated light contains ultraviolet ray of a wavelength of 400 nm or less. In this connection, since the sensitizing dye is typically excited by absorption of visible light, even if ultraviolet ray is removed, the photocurrent with a high sensitivity can be detected by the irradiation with the visible light.

Preferable examples of the means for removing ultraviolet ray include an optical filter and a spectroscope. The use of an optical filter or a spectroscope makes it possible to control the wavelength of the irradiated light, and in turn to excite only the sensitizing dye while preventing the working electrode itself from being photoexcited. An example of a preferable optical filter may be a colored glass filter such as an ultraviolet cut-filter. An example of a preferable spectroscope may be a spectroscope incorporating a diffraction grating with regard to the capability of strictly controlling the wavelength.

Preferable examples of the light source emitting light containing substantially no ultraviolet ray include a laser, an inorganic electroluminescence (EL) device, an organic electroluminescent (EL) device, and a light emitting diode (LED), most preferably a light emitting diode (LED) or a laser diode. By use of these, it is possible to emit controlled light with a narrow wavelength distribution, resulting in the advantages of a reduction in size, a reduction in weight, low electric-power consumption and longer operating life.

According to a preferred aspect of the present invention, it is preferable to remove light of a wavelength shorter than a cut-off wavelength shown in Table 1 which is calculated by inserting a given band gap of the electron accepting substance used into the following equation. This makes it possible to effectively reduce the generation of background electric-current in accordance with the properties of the electron accepting substance.

Band gap $(eV) = h\nu = hc/\lambda = 1239.8/\lambda(nm)$
(h: Planck's constant, c: velocity of light)

TABLE 1

| Electron accepting substance | Band gap (eV) | Suitable cutoff wavelength (nm) |
| --- | --- | --- |
| Rutile titanium oxide | 3.2 | 387 |
| Anatase titanium oxide | 3.0 | 413 |
| Zinc oxide | 3.1 | 400 |
| Strontium titanate | 3.2 | 387 |
| Tin oxide | 3.5 | 354 |
| Tungsten oxide | 2.8 | 443 |
| Niobium oxide | 3.1 | 400 |
| Iron oxide | 2.2 | 564 |

It should be noted that since the electron accepting substance may have an impurity level, it is possible, just to make sure, that the cutoff wavelength is set longer than the wavelength shown in Table 1. Also, when the working electrode is formed of a plurality of electron accepting substances, it is preferable to remove a wavelength shorter than the cutoff wavelength of the component having the smallest band gap of the constituent components.

As described earlier, the electric-current meter 36 is connected between the working electrode 22 and the counter electrode 23, so that the photocurrent flowing in the system by the light irradiation is measured by the electric-current meter. This enables detection of the analyte. The current value at this point reflects the amount of sensitizing dye trapped on the working electrode. For example, when the analyte is a nucleic acid, the amount of double-stranded formed between complementary nucleic acids is reflected as the current value. Accordingly, the analyte can be quantitatively determined from the obtained current value. In consequence, according to a preferred aspect of the present invention, the electric-current meter further comprises means for calculating the concentration of the analyte in the sample liquid from the obtained amount of the electric-current or the obtained electric quantity.

According to a preferred aspect of the present invention, in the process of detecting the photocurrent, the current value is measured and the concentration of the analyte in the sample liquid can be calculated from the obtained amount of the electric-current or the obtained electric quantity. This calculation for the analyte concentration can be performed by applying the measured electric current value or electric quantity to a pre-created calibration line of analyte concentration versus electric current value or electric quantity. In the method of the present invention, since the amount of the sensitizing dye trapped on the working electrode is reflected in the current value, an exact current value corresponding to the analyte concentration is obtained, rendering the method suitable for quantitative measurement.

According to another preferred aspect of the present invention, it is possible to use an analyte pre-labeled with the sensitizing dye as a competitive substance to quantitatively determine a second analyte which is not labeled with the sensitizing dye and is capable of specifically bonding to a probe substance. The second analyte preferably has properties of more easily bonding specifically to the probe substance than the labeled analyte. If these two kinds of analytes compete with each other to specifically bond to the probe substance, the correlation between the detected current value and the concentration of the second analyte is shown. That is, since the number of competitive substances specifically bonded to the probe substance is reduced as the number of second analytes not labeled with dye increases, a calibration line in which the detected current value is reduced as the concentration of the second analyte increases can be obtained. As a result, it is possible to detect and quantitatively determine the second analyte not labeled with the sensitizing dye.

Figure 8:
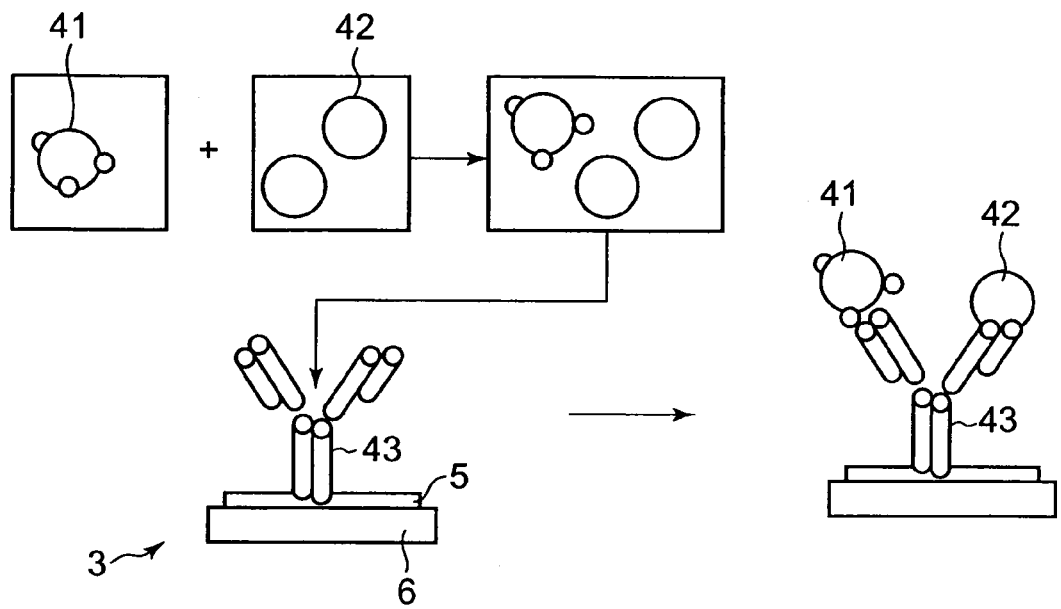
FIG. 8 is a diagram illustrating the process of immobilizing analytes on a probe substance in a case where the analyte and the second analyte competing with each other and having specific bonding properties are antigens, and the probe substance is an antibody.

According to a more preferable aspect of the present invention, the analyte and the second analyte are preferably antigens and the probe substance is preferably an antibody. FIG. 8 illustrates the process of immobilizing the analyte and the second analyte on the probe substance in this aspect. As shown in FIG. 8, an antigen 41 labeled with the sensitizing dye and an antigen 42 not labeled with the dye compete to specifically bond to an antibody 43. Accordingly, as the number of antigens 42 not labeled with the dye increases, the number of antigens 43 labeled with the dye specifically bonded to the antibody decreases. Because of this, it is possible to obtain a calibration line in which the detected current value is reduced as the concentration of the second analyte increases.

Figure 9:
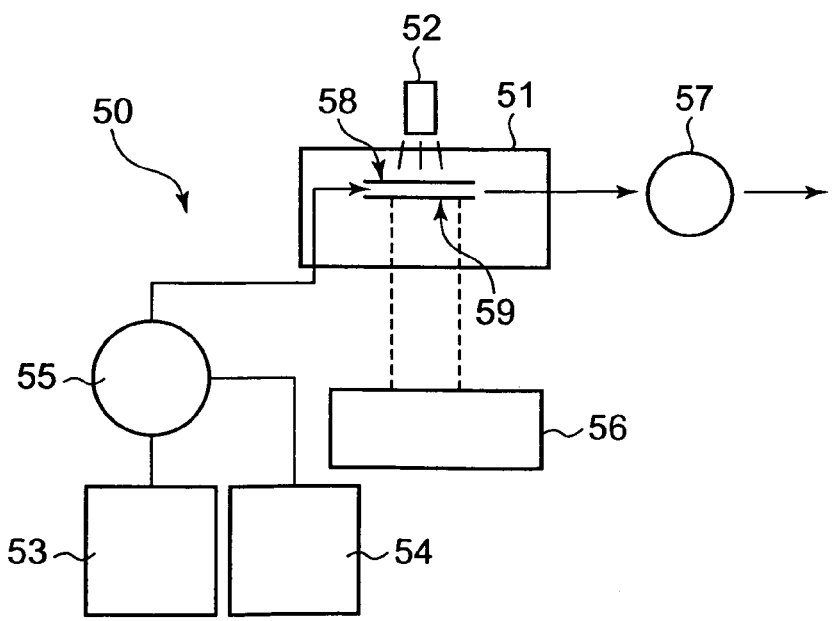
FIG. 9 is a diagram illustrating an example of a device using a flow-type measuring cell and a patterned working electrode.

Method and Device for Measuring Using Flow-Type Measuring Cell and Patterned Electrode As an example of a preferred embodiment of the method and the device of the present invention, a method and a device for measuring using a flow-type measuring cell and a patterned electrode is described. FIG. 9 illustrates the entire structure of the device. The device 50 shown in FIG. 9 comprises a flow-type measuring cell 51, a light source 52, an electrolytic tank 53, a cleaning fluid tank 54, a feed pump 55, an electric-current meter 56 and a discharge pump 57. The flow-type measuring cell 51 comprises a working electrode 58 subjected to patterning and a counter electrode 59 facing the working electrode, and has a flow path formed between the working electrode 58 and the counter electrode 59 for storing and passing the electrolytic solution or the cleaning fluid. That is, the electrolytic solution or the cleaning fluid fed into the measuring cell 51 by the feed pump 55 flows through the flow path while making contact with the working electrode 58 and the counter electrode 59, and then is discharged from the measuring cell 51 by the discharge pump 57. The control of the series of operations and the analysis of the photocurrent values are carried out by a control analyzer which is not shown.

The working electrode 58 is patterned in such a manner as to form, on the electron accepting layer, a plurality of regions isolated from each other on which the probe substance is supported, and is configured such that during the scanning of the light irradiated from the light source, the detection and quantitative determination of the analytes are continuously performed on the samples in the respective regions by a single operating action. An example of such a patterned working electrode is illustrated in FIGS. 10A to 10D and FIGS. 11A to 11C.

Figure 10A:
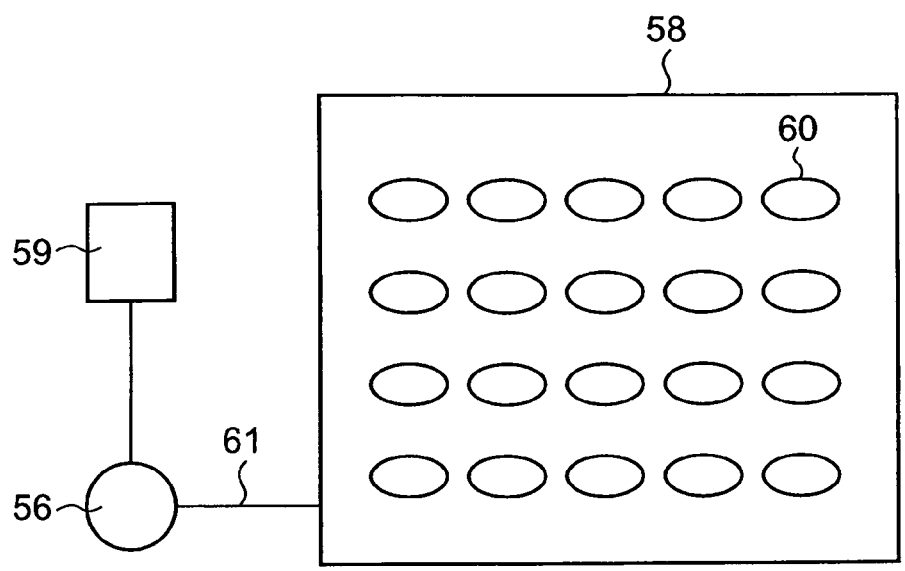
FIGS. 10A to 10D are diagrams illustrating an example of a patterned working electrode.
Figure 10B:
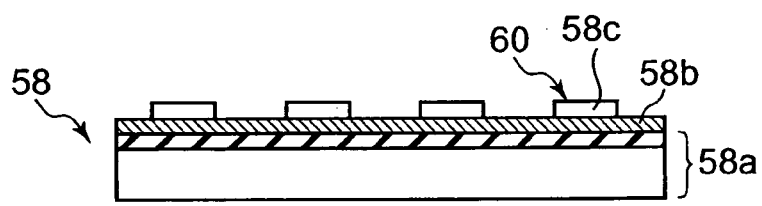
Figure 10C:
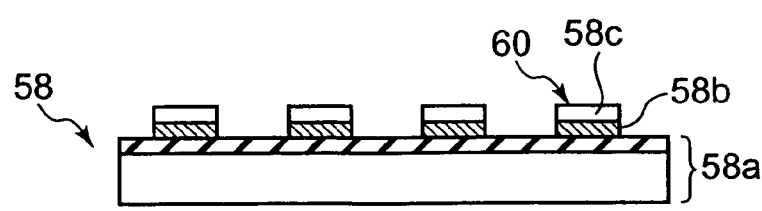
Figure 10D:
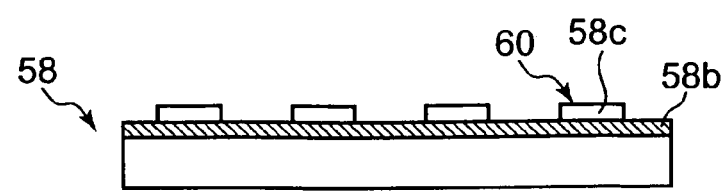
Figure 12:
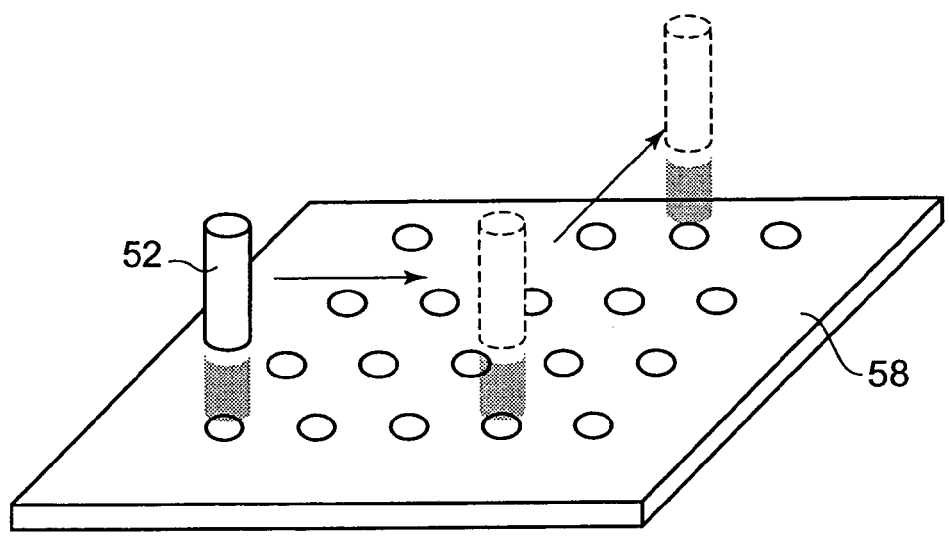
FIG. 12 is a diagram illustrating an example of light sources used for a patterned working electrode.
Figure 13:
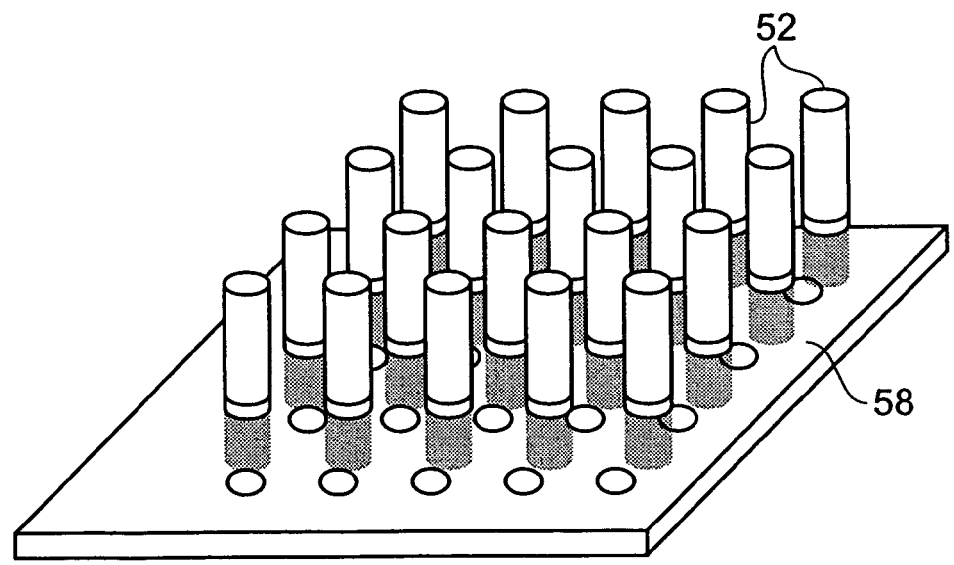
FIG. 13 is a diagram illustrating another example of light sources used for a patterned working electrode.

The working electrode 58 shown in FIGS. 10A and 10B is patterned to form, on an electron accepting layer 58b deposited on the entire face of a conductive substrate 58a, a plurality of spots 60 arranged in rows and columns on which the probe substances 58c are supported. A lead wire 61 is connected to the conductive substrate of the working electrode 58, so that the entire working electrode 58 is connected to the electric-current meter 56 through the lead wire 61. With this working electrode 58, the sequential light irradiation of each spot makes it possible to measure the photocurrent generated between the working electrode 58 and the counter electrode 59 in each spot. Also, since the electrode configuration is relatively simple, the manufacturing of the electrode is easy and the advantage is that a conventional manufacturing technique for a DNA chip can be utilized. Also, in examples of modification, as illustrated in FIG. 10C, the electron accepting layer 58b itself may be shaped in a spot form and the probe substance 58c may be supported thereon, or as shown in FIG. 10D, the conductive substrate may be omitted, the spot-shaped working electrode 58 may be composed of the electron accepting layer 58b alone on which the probe substance 58c is supported, and the lead wire 61 may be connected to the electron accepting layer 58b. In particular, the latter has the advantages that the manufacturing process is simplified and the manufacturing cost is reduced. A light source 52 used for the working electrode may be either a light source that moves above the working electrode 58 in the row and column directions as shown in FIG. 12, or a plurality of light sources that are arranged in correspondence with the spots of the working electrode 58 and are each turned on and off in order as shown in FIG. 13.

Figure 11A:
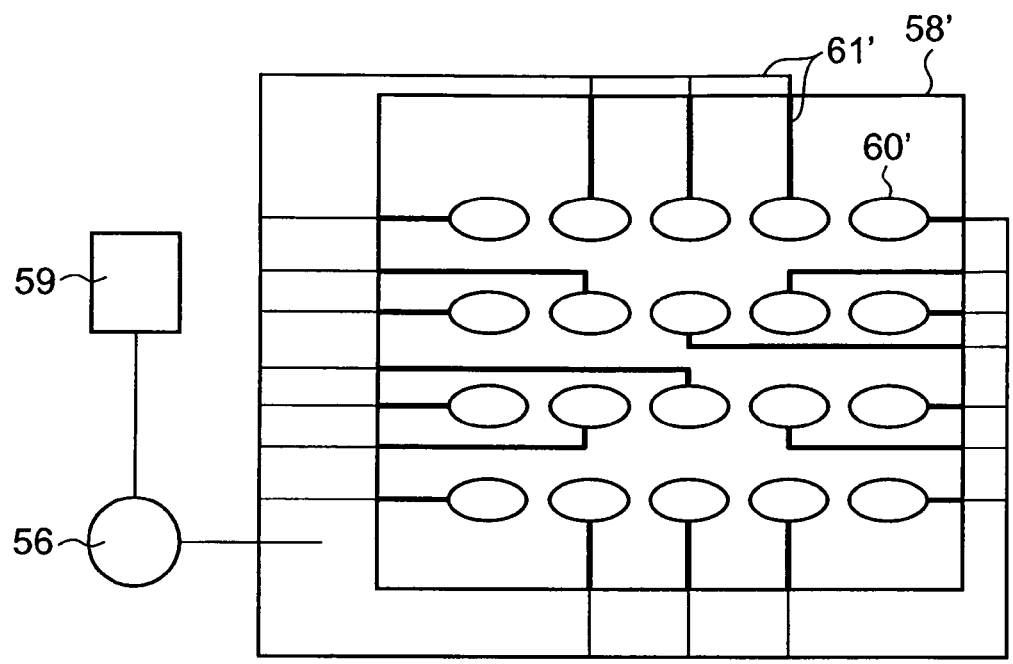
FIGS. 11A to 11C are diagrams illustrating another example of a patterned working electrode.
Figure 11B:
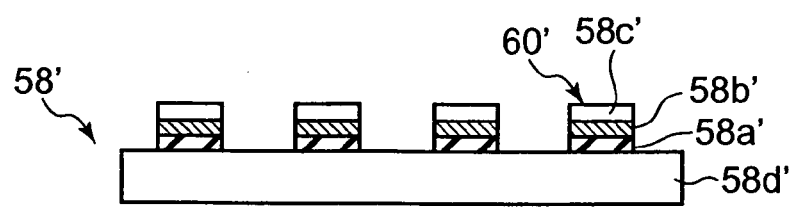
Figure 11C:
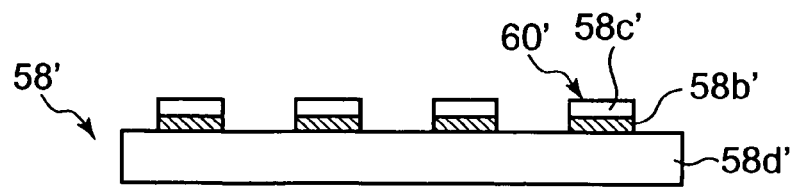

A working electrode 58' illustrated in FIGS. 11A and 11B has an insulating substrate 58d' patterned with a plurality of spots 60' each composed of a conductive substrate 58a' and an electron accepting layer 58b' and arranged in the row and column directions, in which a probe substance 58c' is supported on the electron accepting layer 58b'. Lead wires 61' are respectively connected to the conductive substrates in the respective spots 60', so that each of the spots 60' is connected to the electric-current meter 56 through the lead wire 61'. With the working electrode 58', simply by irradiating the overall surface of the working electrode simultaneously with light, the photocurrent generated in the respective spots is able to be simultaneously and individually measured. Also, the working electrode has the advantage that, since it is possible to achieve the individual measurement of the photocurrent in each spot, photocurrent generated in another spot is not detected as noise. In an example of the modification, as shown in FIG. 11C, the conductive substrate may be omitted, the spot-shaped working electrode 58' may be composed of the electron accepting layer 58b' alone on which the probe substance 58c' may be supported, and the lead wire 61' may be connected to the electron accepting layer 58b', resulting in the advantages of a simplification of the manufacturing process and a reduction in manufacturing cost. A light source 52 used for the working electrode 58' may be, as in the case of the working electrode in FIG. 9, either a light source that moves above the working electrode 58 in the row and column directions, or a plurality of light sources that are arranged in correspondence with the spots of the working electrode 58 and are each turned on and off in order.

An example of the measuring method using the above device will be described below.

First, a sample liquid is brought into contact with the working electrode under the presence of a sensitizing dye to specifically bond an analyte directly or indirectly to a probe substance. By this bond, the sensitizing dye is immobilized on the working electrode 58. In this connection, the electron accepting layer of the working electrode 58 is masked with a spot pattern shown in FIG. 10 to obtain the working electrode 58 patterned with a plurality of spots 60 which are arranged in the row and the column directions and on which the probe substance is supported. The working electrode 58 thus produced is mounted in a flow-type measuring cell 51.

Next, the feed pump 55 is actuated to feed the electrolyte solution from the electrolyte tank 53 into the measuring cell 51 so as to fill the flow path in the measuring cell with the electrolyte solution, and then the solution feeding is stopped. The working electrode 58 is irradiated with light from the light source 52, and then the photocurrent generated between the working electrode 58 and the counter electrode 59 is measured by the electric-current meter 56. In the measurement of the photocurrent value, a value detected after a lapse of tens of seconds from the beginning of the irradiation is preferably adopted. Then, in the control analyzer which is not shown, an analyte concentration is calculated by applying the detected current value to a pre-created calibration line of analyte concentrations versus current values. After completing the measurement of the photocurrent, the feed pump 55 is actuated to feed the cleaning fluid from the cleaning-fluid tank 53 into the measuring cell 51, and at the same time, the discharge pump 57 is actuated to discharge the electrolyte solution from the measuring cell 51, so that the cleaning fluid is substituted for the electrolyte solution in the flow path in the measuring cell, and then the feeding and the discharging of the solution are stopped. As a result, the measuring cell 51 which has been cleaned with the cleaning fluid can be used for the next measurement following the same steps as described above.

Measuring Device with Light Irradiation Mechanism

According to another preferred aspect of the present invention, it is preferable that a plurality of light sources are provided in advance, and the aforementioned measuring device comprises a plurality of stationary light irradiation mechanisms in which the switching between the plurality of light sources is carried out for light irradiation.

Figure 14A:
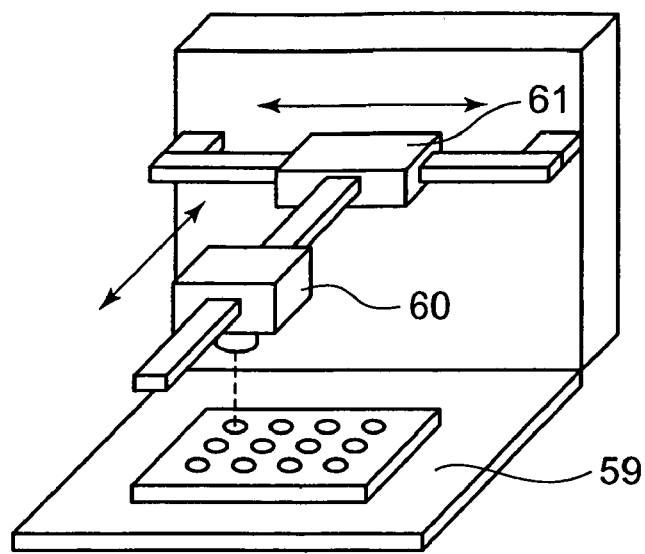
FIGS. 14A and 14B are diagrams illustrating an example of a measuring device comprising a movable-light-source-type light irradiation mechanism.
Figure 14B:
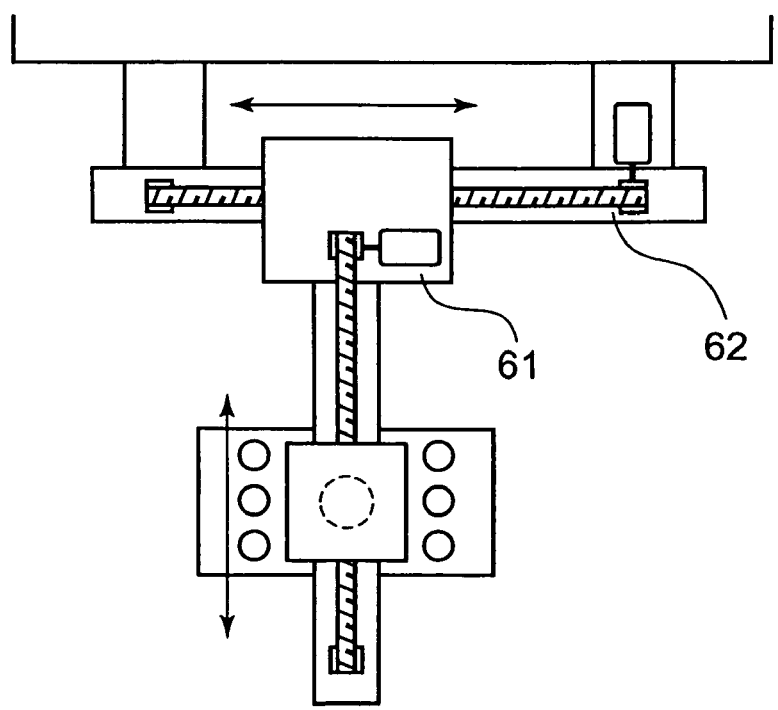

According to another preferred aspect of the present invention, the measuring device preferably comprises a movable-light-source-type light irradiation mechanism in which the light source moves in the X-Y direction with respect to the working electrode in the measuring cell to irradiate an arbitrary region on the working electrode with light. Examples of the device in this aspect include a device in which a light source is attached to an arm movable in the X-Y direction and a sensor unit serving as the measuring cell is fixed. FIG. 14A shows an entire perspective view of an example of the measuring device of such an aspect, and FIG. 14B shows a top view of the example. As shown in FIGS. 14A and 14B, a sensor unit 59 is fixed and a light source 60 moves to the opening of the sensor unit 59 for light irradiation. FIGS. 14A and 14B illustrate a belt drive mechanism which converts the rotation of a motor 61 to a linear motion by a belt 62 as a mechanism for moving in the X-Y direction by way of example, but other mechanisms, for example, a mechanism of using a motor to drive a rack-and-pinion mechanism, and the like, may be used. The start, stop and rotational speeds of the motor rotation are controlled in order to sequentially irradiate biomolecule immobilization regions (spots) on a sensor chip stored in the sensor unit, in which it is possible to set the velocity of emission and whether or not movement is required for irradiation. The sensor unit used in this case may be formed of a structure allowing the electrolyte medium of the present invention to fill the space between the counter electrode and the working electrode. The light source may stop when irradiating the region of the working electrode immobilizing the analyte with the sensitizing dye bonded thereto through the probe substance, or may move continuously from region to region of the work electrode immobilizing the analyte with the sensitizing dye bonded thereto through the probe substance.

Figure 15A:
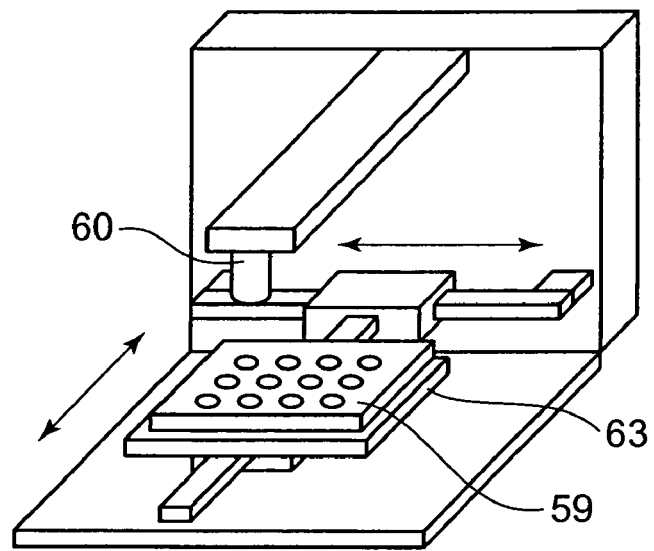
FIGS. 15A and 15B are diagrams illustrating an example of a measuring device comprising a movable-cell-type light irradiation mechanism.
Figure 15B:
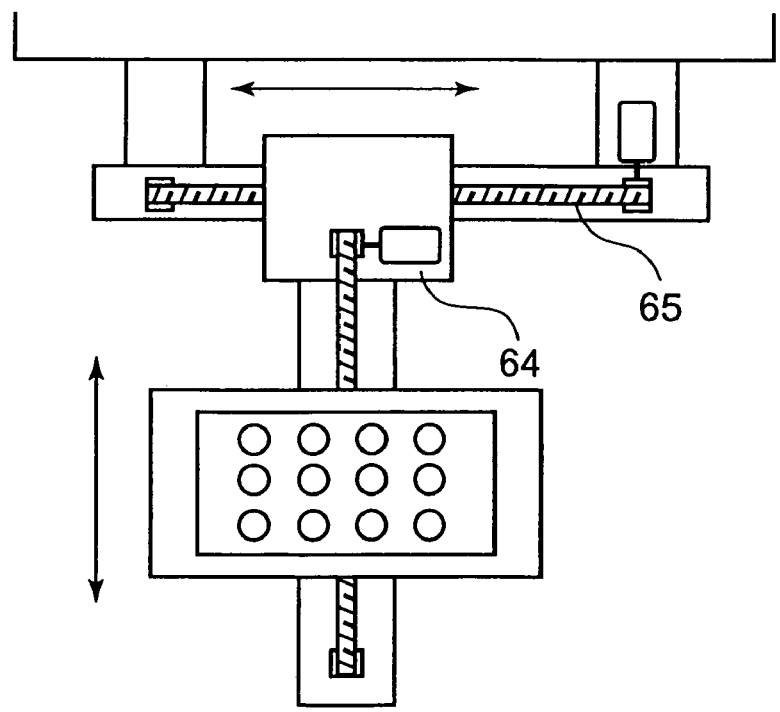

According to further another preferred aspect of the present invention, the measuring device preferably comprises a movable-cell-type light irradiation mechanism in which the light source is fixed and the measuring cell is moved in the X-Y direction with respect to the fixed light source to irradiate an arbitrary region on the working electrode. Examples of the device in this aspect include a device having a sensor unit serving as the measuring cell attached to a stage movable in the X-Y direction and the light source is fixed. FIG. 15A shows an entire perspective view of an example of the measuring device of such an aspect, and FIG. 15B shows the top view. As shown in FIG. 15, the light source 60 is fixed and a stage 63 carrying the sensor unit 59 moves in the X-Y direction, thus irradiating the sensor-unit opening with light. FIGS. 15A and 15B illustrates a belt drive mechanism which converts the rotation of a motor 64 to a linear motion by a belt 65 as a mechanism for moving in the X-Y direction by an example, but other mechanisms, for example, a mechanism using a motor to drive a rack-and-pinion mechanism, and the like, may be used. The start, stop and rotational speeds of the motor rotation are controlled in order to sequentially irradiate biomolecule immobilization regions (spots) on a sensor chip stored in the sensor unit 59, in which it is possible to set the velocity of emission and whether or not movement is required for irradiation. The sensor unit 59 used in this case may have a structure allowing the electrolyte medium of the present invention to fill the space between the counter electrode and the working electrode. The measuring cell may stop when irradiating the region of the working electrode immobilizing the analyte with the sensitizing dye bonded thereto through the probe substance, or may move continuously in a region of the work electrode immobilizing the analyte with the sensitizing dye bonded thereto through the probe substance.

Figure 16:
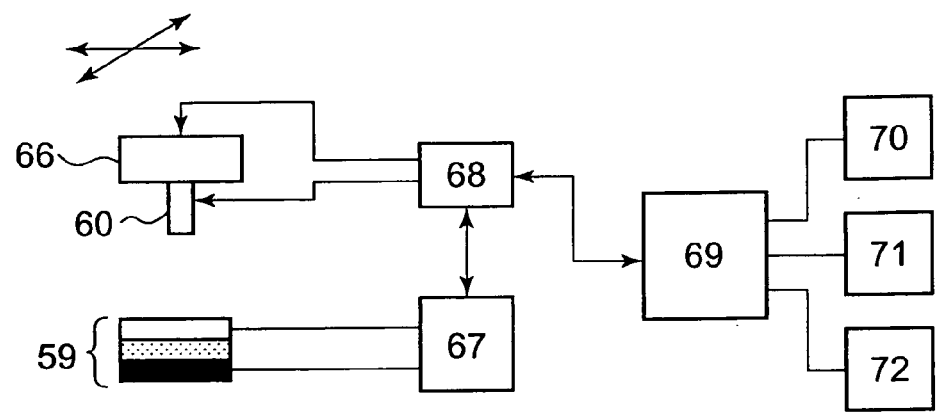
FIG. 16 is a diagram illustrating an example of the movable-light-source-type light irradiation mechanism in the device shown in FIGS. 14A and 14B.
Figure 17:
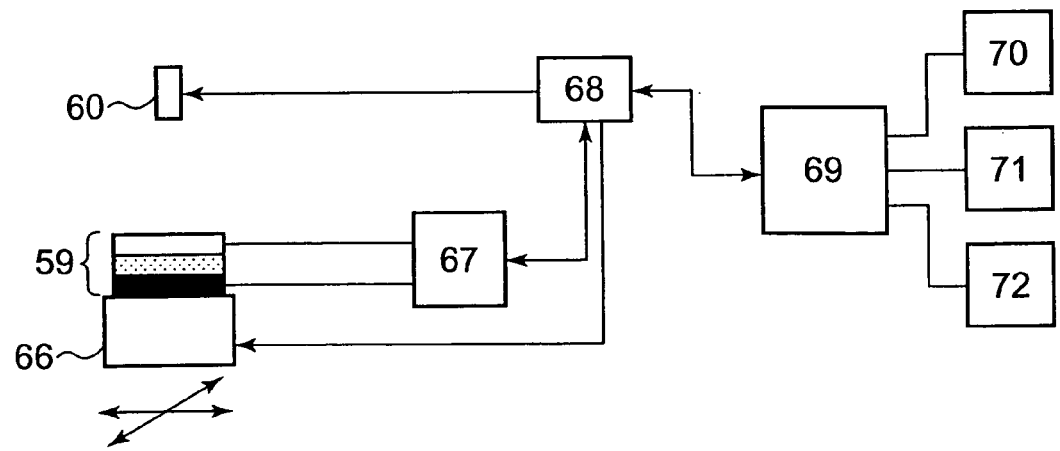
FIG. 17 is a diagram illustrating an example of the movable-cell-type light irradiation mechanism in the device shown in FIG. 15.

As an example of the movable-light-source-type light irradiation mechanism in the device shown in FIG. 14, a block diagram of the device having the light source 60 attached to an XY moving mechanism 66 is shown in FIG. 16. Also, as an example of the movable-cell-type light irradiation mechanism in the device shown in FIG. 15, a block diagram of the device having the sensor unit 63 attached to an XY moving mechanism 66 is shown in FIG. 17. As shown in FIGS. 16 and 17, a computer 69, through an interface board 68, turns on/off the light source 60, controls the XY moving mechanism 66, controls an electric-current meter 67 and receives a current signal. In this case, an external PC may be used as the computer 69. Alternatively, a microcomputer installed in the device may be used, while an input unit 70, a display unit 71 and a storage unit 72 may also be installed in the measuring device. The functions of the input unit 70, the display unit 71 and the storage unit (not shown) may be appropriately assigned to the microcomputer incorporated in the device and the external PC.

Figure 18A:
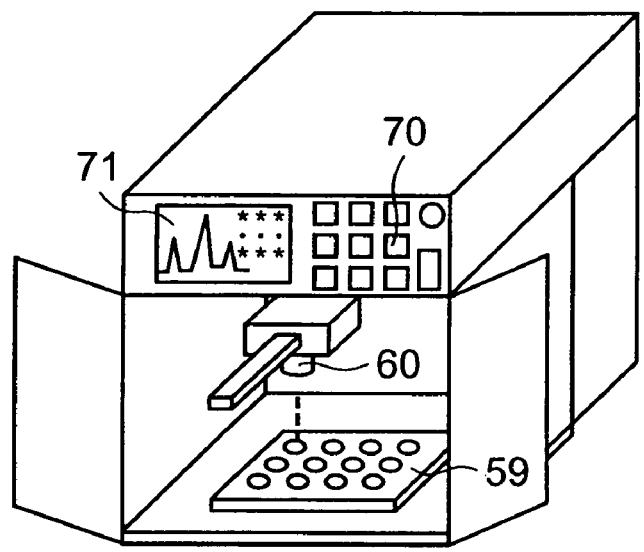
FIGS. 18A and 18B are diagrams illustrating examples of a measuring device comprising a light irradiation mechanism.
Figure 18B:
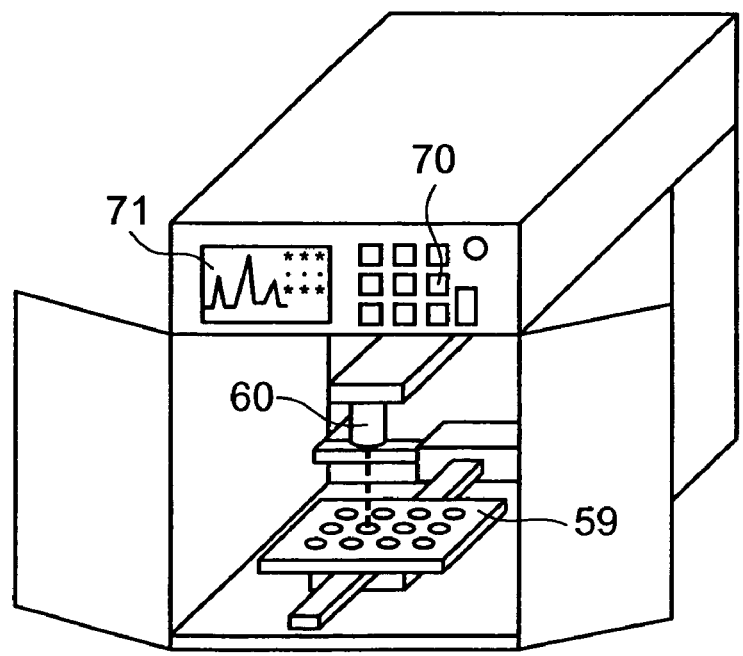

FIG. 18 shows an outside perspective view of an example of the measuring device comprising such an irradiated-light-moving mechanism. As shown in FIG. 18, the device may be designed to incorporate an input unit 70 such as a key, a button and the like for inputting the operational conditions, a display unit 71 for setting conditions and measurement results, and a storage unit. These functions may all be performed by the external PC.

Photocurrent Detector Using Manufacturing Method such as MEMS

Figure 19:
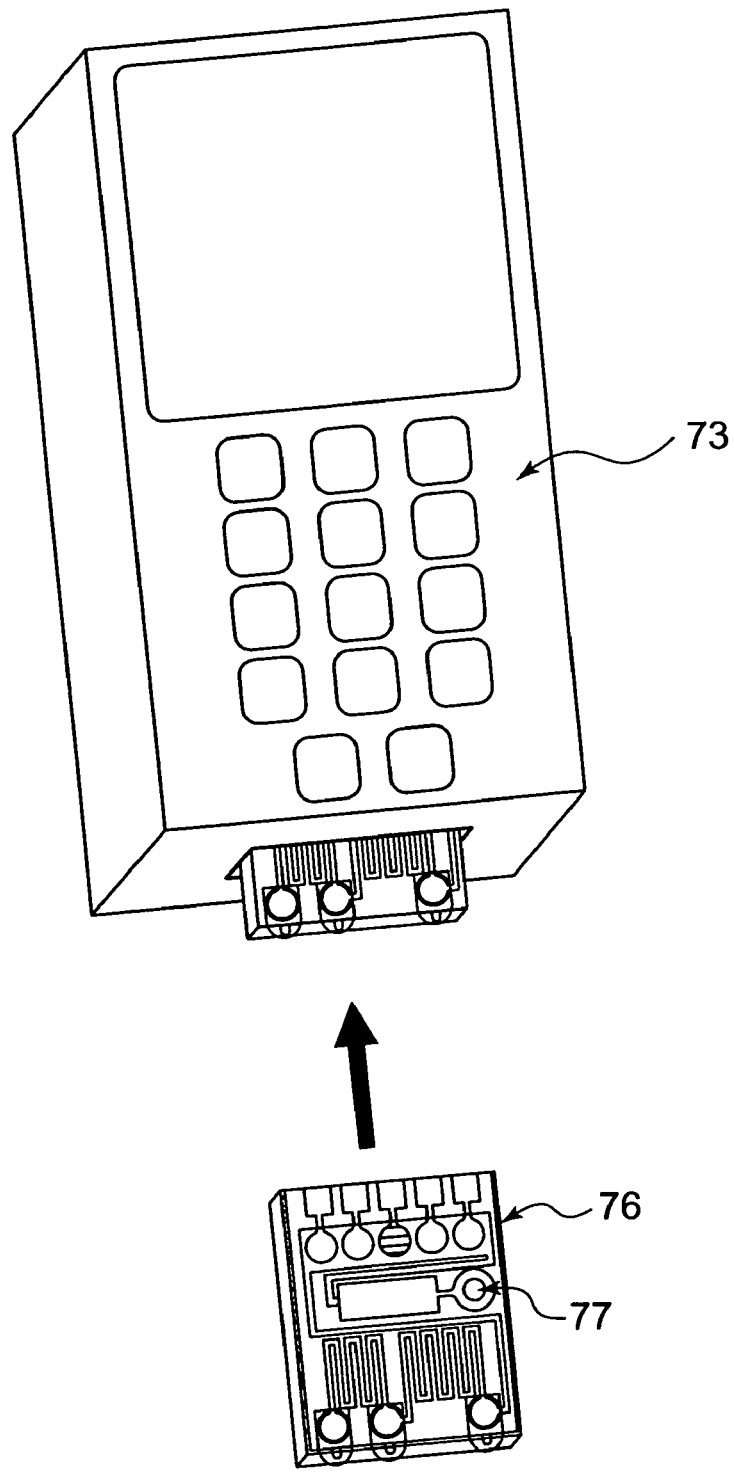
FIG. 19 is a schematic perspective view of an example of a photocurrent detector using a manufacturing method such as MEMS.
Figure 20:
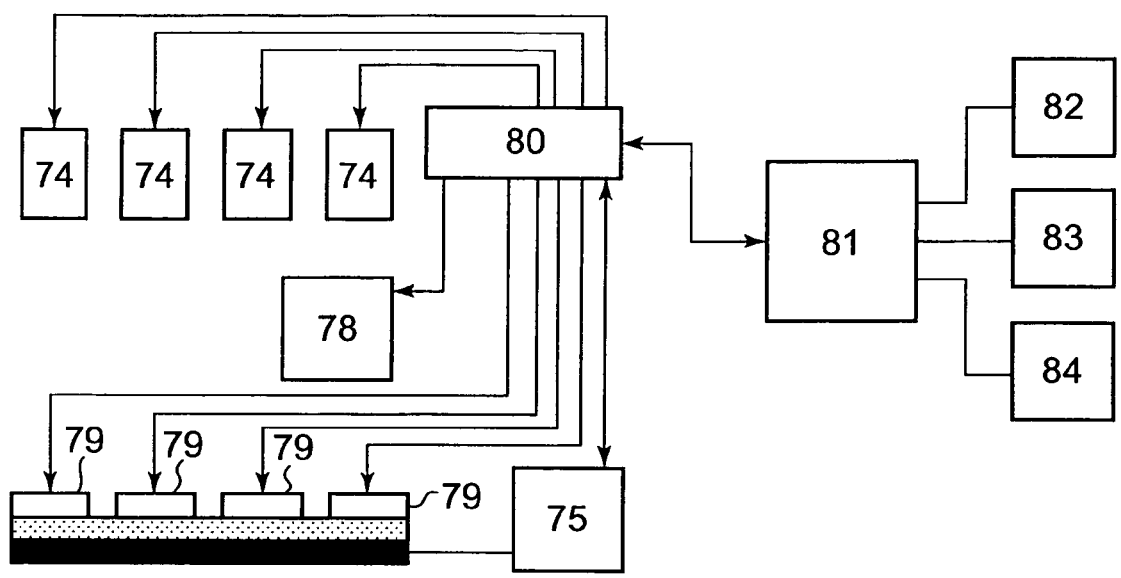
FIG. 20 is a configuration diagram of the photocurrent detector shown in FIG. 19.
Figure 21:
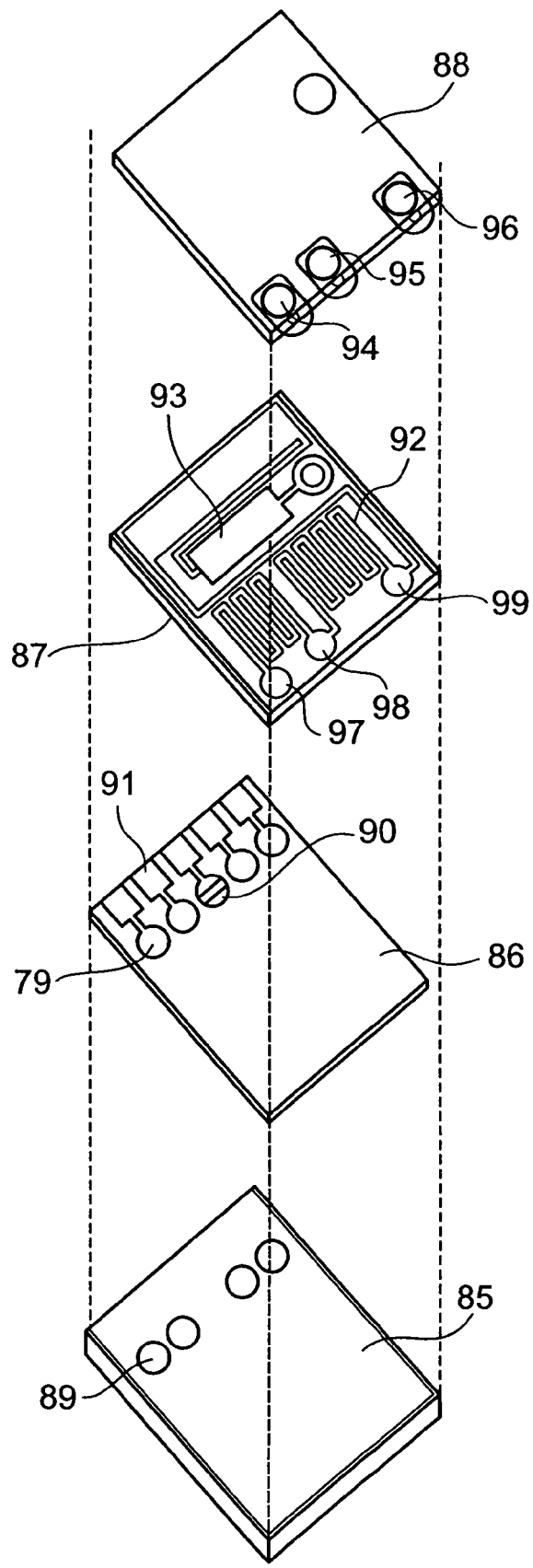
FIG. 21 is an exploded perspective view of a detector chip shown in FIG. 19.

FIG. 19 shows a schematic perspective view of an example of a photocurrent detector using a manufacturing method such as MEMS, FIG. 20 shows a block diagram of the detector, and FIG. 21 shows an exploded perspective view of a detection chip used in the detector. The photocurrent detector 73 is provided with a light source 74, an electric-current meter 75, a function for fixing a detection chip 76, and a pump 78 sucking through a suck port 77 of the detection chip 76. A computer 81, through an interface board 80, selects a light source 74 (a plurality of light sources) and a working electrode 79 (this example shows the example using the patterned electrode shown in FIG. 11), controls the suction pump 78 and the electric-current meter 75 and receives a current signal. In this case, a microcomputer installed in the device is used as the computer 81, and an input unit 82, a display unit 83 and a storage unit 84 are also installed in the measuring device. The input unit 82 is provided with a key, a button and the like for inputting the operational conditions and the setting conditions, and the display unit 83 displays the measurement results. The measurement results can be stored in the storage unit 84. The detection chip 76 comprises a lower member 85, an electrode substrate 86, a PDMS chip 87 and an upper member 88, while the lower member 85 has openings 89 provided for the passage of the light from the light source 74. The electrode substrate 86 is provided with a working electrode 79, a counter electrode 90 and a terminal 91 for electrically connecting to a reader. The PDMS chip 87 is provided with a solution-feeding flow path 92 and a waste fluid bin 93, and also with solution ports 97, 98, 99 which are coupled to an electrolyte inlet 94, a cleaning fluid inlet 95 and a sample solution inlet 96 formed in the upper member 88. The use of the photocurrent reader and the detection chip using a manufacturing method such as MEMS makes it possible to measure an analyte having specific bonding properties such as a nucleic acid, an endocrine disruptor, an antigen and the like with a slight amount of sample solution and a simple operation.

Buffer Solution Used in Contact with Working Electrode

According to a preferred aspect of the present invention, as the buffer solution used in contact with the working electrode, it is preferred to use a buffer solution comprising a buffer agent which is free from a carboxyl group, a phosphoric acid group and an amino group, and a solvent. Examples of the use in contact with the working electrode include a process for immobilizing the probe substance on the working electrode, a process for immobilizing the analyte through the probe substance on the working electrode, a process for cleaning the working electrode after the immobilization of the analyte, and the like. The use of the buffer solution comprising the above-described buffer agent makes it possible to dramatically improve the sensitivity of detecting an analyte by use of photocurrent without impairing the properties of the object to be measured and the working electrode. This property is particularly notable when the surface of the working electrode comprises titanium oxide or strontium titanate.

Though it is not known exactly why the detecting sensitivity is dramatically improved when the above-described buffer solution is used, it is conceivable that this is because the interaction with the working electrode does not easily occur, unlike a buffer solution generally used in the field of biochemistry which comprises primarily a phosphate buffer solution and either amine or carboxylic acid. Specifically, it is conceivable that if a buffer agent comprises a carboxyl group, a phosphate group and an amino group, these groups initiate an interaction with the working electrode, which then causes removal of the probe substance on the working electrode and/or inhibition of electron injection from the dye to the working electrode, resulting in a reduction in values of the detected current. However, the present invention is not limited to this.

The aforementioned buffer agent is not limited, provided that it has a chemical structure not comprising a carboxyl group, a phosphate group and an amino group and has buffering effects, but examples of preferable buffing agents include compounds expressed by the following formula (1):

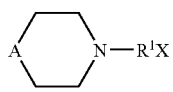

(I)

(in which R1 is an alkylene group with carbon numbers from 1 to 4 which may be substituted by a hydroxyl group, X is a sulfonic acid group or a salt thereof, A is O or YR2-N (wherein R2 is synonymous with R1, Y is a sulfonic acid group or a salt thereof, or a hydroxyl group)). These buffer agents have the advantage that an analyte having specific bonding properties such as a nucleic acid, an endocrine disruptor, an antigen and the like are stably held to improve the measuring accuracy.

According to a preferred aspect of the present invention, the alkylene group is preferably an ethylene group. Specific examples of such a buffer agent include 2-[4-(2-hydroxyethyl)-1-piperazinyl]ethanesulfonic acid (HEPES), piperazine-1,4-bis(2-ethanesulfonic acid) (PIPES), piperazine-1,4-bis(2-ethanesulfonic acid), sesquisodium salt (PIPES sesquisodium) and 2-morpholinoethane sulfonic acid (MES).

According to a preferred aspect of the present invention, the alkylene group is preferably a propylene group. Specific examples of such a buffer agent include 3-[4-(2-hydroxyethyl)-1-piperazinyl]propanesulfonic acid (EPPS), 2-hydroxy-3-[4-(2-hydroxyethyl)-1-piperazinyl]propanesulfonic acid (HEPPSO), 3-morpholinopropanesulfonic acid (MOPS), 2-hydroxy-3-morpholinopropanesulfonic acid (MOPSO) and piperazine-1,4-bis(2-hydroxy-3-propanesulfonic acid) (POPSO).

According to a preferred aspect of the present invention, the concentration of the buffer agent is preferably set to a range from 1 mM to 200 mM, more preferably from 1 mM to 100 mM, furthermore preferably from 10 mM to 50 mM.

A solvent used for the aforementioned buffer agent is not limited, provided that it does not impair the properties of the analyte and the working electrode.

According to a preferred aspect of the present invention, in order to stably hold an analyte having specific bonding properties such as a nucleic acid, an endocrine disrupter, an antigen and the like for an improvement in measuring accuracy, the buffer solution has a PH ranging preferably from 5.0 to 9.0, more preferably from 6.0 to 8.0, furthermore preferably from 6.5 to 7.5.

The application of the aforementioned buffer solution is not limited, provided that it is used in contact with the working electrode used in the method of the present invention. Examples of the preferable application include, as described above, a solvent of a sample liquid containing an analyte, a solvent of a solution containing a probe substance capable of specifically bonding directly or indirectly to an analyte, a cleaning fluid for a working electrode or a measuring cell, and the like.

EXAMPLES

The present invention will be described in more detail by use of the following examples. The present invention is not limited to these examples.

Example 1

Reference

This example shows that the photoelectric conversion can be achieved even in the bond through a silane coupling agent. Specifically, the conductive faces of an FTO glass and an ITO glass were treated with the silane coupling agent to introduce an amino group onto the surfaces. The amino group was made react with a dye having an active ester group so that the dye was immobilized by a covalent bond. This was irradiated with exciting light, and the photocurrent was measured. The details are as follows.

A fluorine-doped tin oxide ($F$—$SnO_2$:FTO) coated glass (produced by Al Tokushu Garasu Company, U-film, sheet resistance: 15Ω/☐0) and a tin-doped indium oxide ($Sn$—$In_2$:ITO) coated glass (produced by Toyo Seimitsu Kogyo Kabushiki Kaisha, 100Ω/☐) were subjected to ultrasonic cleaning in an acetone, then in ultra-pure water including 0.1 vol % of Tween20, and further in ultra-pure water for 15 minutes each to remove contaminant and residual organic substance. Then, the glasses were shaken for 15 minutes in 5M aqueous sodium hydroxide. Then, for removing the sodium hydroxide, the shaking for 5 minutes in ultra-pure water was repeated three times, changing the water each time. The glasses were taken out and air was blown on the glasses to blow away the residual water, and then the glasses were immersed in anhydrous methanol for hydroextraction.

The solution used in the coupling treatment was prepared by adding 2 vol % of 3-aminopropyltrimethoxysilane (APTMS) to a solvent comprising 95% methanol and 5% ultra-pure water and then stirring the mixture for 5 minutes at room temperature.

The above glasses were immersed in the coupling treating solution and then slowly shaken for 15 minutes. Then, the glasses were taken out and subjected to 3 sets of the process of shaking them approximately 10 times in methanol for removing the surplus coupling treating solution, changing the methanol for each process. Then, the glasses were kept at 110° C. for 30 minutes to bond the coupling agent to the glasses. After cooling them at room temperature, a spacer perforated (5 mm square) tape was affixed to the glasses, and then tweezers were used to remove the air remaining on the adhesive surface of the tape. In addition, a silicone sheet having 5-mm-square openings formed therein was placed on and brought into close contact with the tape.

Next, 25 μl of either a rhodamine adjusted to 100 μM by being dissolved in 50 mM HEPES pH0.7 and having an active ester group (Tetramethylrhodamine Protein Labeling Kit, Molecular Probes Company) or Cy5 having an active ester group (Cy5 Mono-Reactive Dye Pack, Amersham Biosciences Company) was filled to spread uniformly to the openings placed on the glasses which had undergone the foregoing treatment. Then, each of these glasses was covered right from above with a prepared glass to prevent air bubbles from entering the dye solution, was then housed in a plastic container in which the vapor pressure had been adjusted by moist paper or the like, and was then incubated overnight at 37° C.

After completion of the incubation, the prepared glass was removed and the glass was shaken in ultra-pure water to be cleaned (ten minutes×3 sets). Then, air was blown to remove the residual water, and then the glasses were dried at room temperature.

The electrodes thus obtained were mounted in a flow-type measuring cell (example 1 of the device). Regarding the structure of the cell portion, the working electrode was placed opposite a platinum counter electrode so as to prevent the working electrode and the counter electrode from coming into contact with each other to make a short circuit, and additionally, for the purpose of creating a space to be filled with an electrolytic solution, a 500 μm-thick silicone sheet was inserted. The silicone sheet has a hole of well over 5 mm square formed therein, into which the electrolytic solution is sent and stored so that the probe-immobilized face of the working electrode makes contact with the electrolytic solution. The working electrode was electrically connected to a spring probe through which the working electrode was connected to a potentiostat (ALS Model 832A, PAS Kabushiki-Kaisha), while the platinum counter electrode was connected at an end with a lead wire through which the counter electrode is connected to the potentiostat. The fluid used as the electrolytic solution was a fluid mixture of a mixed solvent of an acetonitrile and an ethylene carbonate at a volume ratio of 7:3, and iodine 0.01M and tetrapropylammonium iodide 0.1M which were dissolved in the mixed solvent. This electrolyte solution was filled into the space between the working electrode and the platinum counter electrode which had been mounted in the aforementioned flow-type measuring cell. Next, an LED (CCS Kabushiki-Kaisha, HLV-24GR-NR-3W, central wavelength:530 nm, output power:67 mW in the case of using rhodamine, HLV-27-NR-R, central wavelength: 627 nm, output power:67 mW in the case of using Cy5) fixed in the flow-type measuring cell was used as a light source to irradiate the surface of the working electrode with light, and the current flowing between the working electrode and the platinum counter electrode was measured with time. The measurement was made for 180 seconds, but the light irradiation was conducted only for 60 seconds, beginning 60 seconds after the time when the current measurement had been started. The observed current values were corrected by subtracting the value after a lapse of 180 seconds from the value after a lapse of 120 seconds.

Figure 22A:
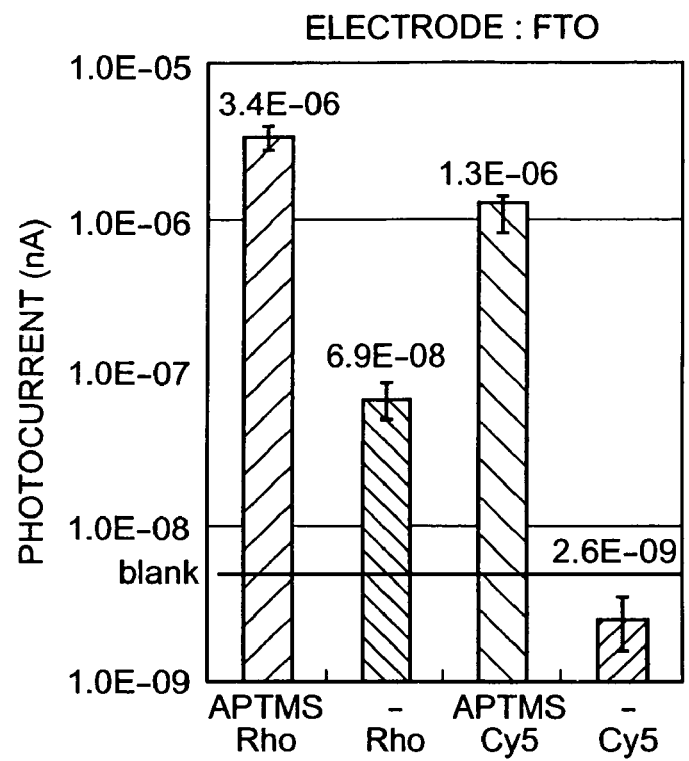
FIGS. 22A and 22B are graphs showing the detected current values measured in Example 1.
Figure 22B:
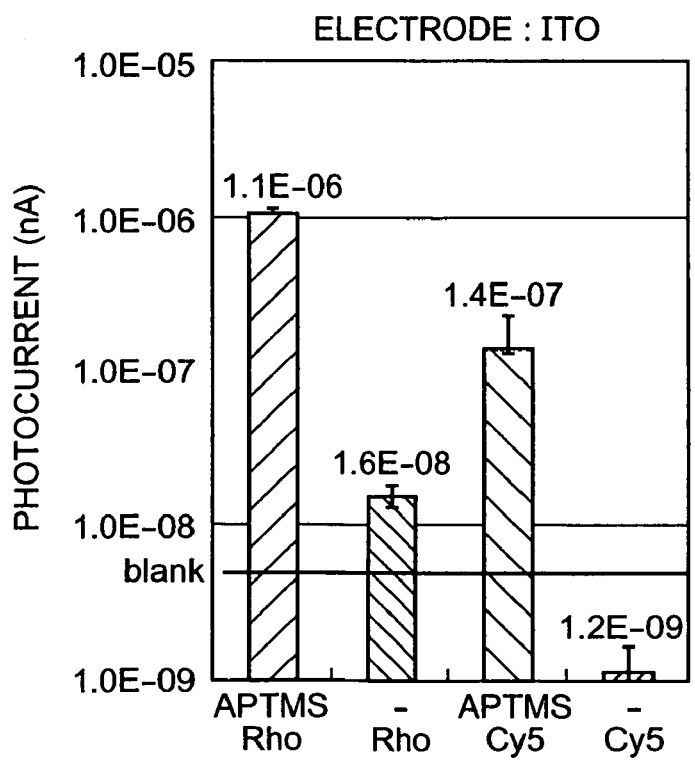

In consequence, the photocurrent values in the case of using the FTO electrode and the ITO electrode are measured as respectively shown FIGS. 22A and 22B. It can be recognized from these graphs that the photocurrent derived from the dye is greater when the silane coupling agent is used for the bond than when it is not used for the bond. It is seen from this that the amount of dye immobilized is increased by the silane coupling agent and the conductivity of the electrode is provided even after the silane coupling treatment. From the foregoing it can be shown that the FTO glass and the ITO glass which are subjected to the silane coupling treatment can be used as a material for a working electrode of a dye-sensitized biosensor.

Example 2

Reference

This example shows a difference between the current values observed in the complementary DNA and non-complementary DNA. Specifically, an FTO glass was treated with the silane coupling agent to introduce an amino group onto the surfaces. The amino group and the probe DNA were bonded with electrostatic action to each other, followed by ultraviolet-ray irradiation to form a covalent bond to immobilize the probe on the electrode. This was hybridized with target DNA labeled with Cy5, and then irradiated with exciting light, followed by measurement of the photocurrent. The details are as follows.

A fluorine-doped tin oxide (F—$SnO_2$:FTO) coated glass (produced by AI Tokushu Garasu Company, U-film, sheet resistance: 15Ω/□) was subjected to ultrasonic cleaning in an acetone, then in ultra-pure water including 0.1 vol % of Tween20, and further in ultra-pure water for 15 minutes each to remove contaminant and residual organic substance. This was shaken for 15 minutes in 5M aqueous sodium hydroxide. Then, for removing the sodium hydroxide, the shaking for 5 minutes in ultra-pure water was repeated three times, changing the water each time. The glass was taken out and air was blown on the glass to blow away the residual water, and then the glass was immersed in anhydrous methanol for hydroextraction.

The solution used in the coupling treatment was prepared by adding 2 vol % of 3-aminopropyltrimethoxysilane (APTMS) to a solvent comprising 95% methanol and 5% ultra-pure water and then stirring it for 5 minutes at room temperature.

The above glass was immersed in this coupling treating solution and then slowly shaken for 15 minutes. Then, the glass was taken out and subjected to 3 sets of the process of shaking it approximately 10 times in methanol for removing the surplus coupling treating solution, changing the methanol for each process. Then, the glass was kept at 110° C. for 30 minutes to bond the coupling agent to the glass. After cooling it at room temperature, a spacer perforated (5 mm square) tape was affixed to the glass, and then tweezers were used to remove the air remaining on the adhesive surface of the tape. In addition, a silicone sheet having 5-mm-square openings formed therein was placed on and brought into close contact with the tape.

Next, the probe DNA prepared to 1 μM by being dissolved in 2×SSC (5'NH2-ACCTTCATCAAAAACATCAT-CATCC3') was maintained at 95° C. for 5 minutes, and then the probe DNA was immediately moved onto ice and maintained for 10 minutes to denature the DNA, 25 μM of which was then filled to spread uniformly to the openings on the glass which had undergone the foregoing treatment.

Then, this was maintained for one hour at 75° C. to vapor the solvent, and then the silicone sheet was peeled off. Then, a UV cross-linker (UVP Corporation, CL-1000 model) was used to irradiate the glass with 120 mJ of ultraviolet ray to provide a working electrode with the probe immobilized thereon.

This electrode was subjected to 2 sets of the process of being shaken 10 times in ultra pure water to remove the SSC component (NaCl and sodium citrate), changing the ultra pure water for each process. The electrode was immersed in boiling water for 2 minutes, taken out, and then aired to blow away the residual water. The electrode was immersed in anhydrous ethanol at 4° C. for one minute for hydroextraction, and then aired to blow away the residual ethanol. Then, a silicone sheet having 5-mm-square openings formed therein was placed on and brought into close contact with the working electrode.

Next, DNA complementary to the probe, adjusted to reach 10 nM of the concentration by being dissolved in a 5×SSC+ 0.5% SDS (5'GGATGATGATGTTTTTGATGAAGGT-Cy5-3') and non-complementary DNA (5'TTGAGCAAGT-TCAGCCTGGTTAAG-Cy5-3') were maintained at 95° C. for 5 minutes, and then they were immediately moved onto ice and maintained for 10 minutes to denature the DNA, 25 μl of which respectively were then filled to spread uniformly to the openings on the working electrode which had undergone the foregoing treatment. The working electrode was covered right from above with a prepared glass to prevent air bubbles from entering the DNA solution, was then housed in a plastic container in which the vapor pressure had been adjusted by moist paper or the like, and was then incubated overnight at 37° C.

After completion of the incubation, the prepared glass was removed, and the working electrode was cleaned for approximately 2 seconds with a 2×SSC+0.1% SDS heated to 37° C. The electrode was propped against a slide glass and cleaned in the following steps.

(1) 2×SSC+0.2% SDS
   Room Temperature
   Shaking 3 min.×3 times with the solution changed each time
(2) 0.2×SSC+0.2% SDS
   Ordinary Temperature
   Shaking 3 min.×2 times with the solution changed each time
(3) 0.2×SSC+0.2% SDS
   37° C.
   Shaking 10 min.×2 times with the solution changed each time
(4) 0.2×SSC+0.2% SDS
   Ordinary Temperature
   Shaking 3 min.×1 time
(5) 0.2×SSC
   Ordinary Temperature
   Shaking 10 times×3 times with the solution changed each time
(6) Ultra Pure Water
   Ordinary Temperature
   Swinging 10 times×2 times with solution changed
(7) Aired to Remove the Residual Water.

The electrodes thus obtained were mounted in a flow-type measuring cell. Regarding the structure of the cell portion, the working electrode was placed opposite a platinum counter electrode so as to prevent the working electrode and the counter electrode from coming into contact with each other to make a short circuit, and additionally for the purpose of creating a space to be filled with an electrolytic solution, a 500 μm-thick silicone sheet was inserted. The silicone sheet had a hole of well over 5 mm square formed therein, into which the electrolytic solution was sent and stored so that the probe-immobilized face of the working electrode made contact with the electrolytic solution. The working electrode was electrically connected to a spring probe through which the working electrode was connected to a potentiostat (ALS Model 832A, PAS Kabushiki-Kaisha), while the platinum counter electrode was connected at one end with a lead wire through which the counter electrode was in connection to the potentiostat. As the electrolytic solution, a fluid mixture of a mixed solvent of an acetonitrile and an ethylene carbonate at a volume ratio of 7:3, and iodine 10 mM and tetrapropylammonium iodide 100 mM which were dissolved in the mixed solvent was used. This electrolyte solution was filled into the space between the working electrode and the platinum counter electrode which had been mounted in the aforementioned flow-type measuring cell. Next, an LED (CCS Kabushiki-Kaisha, HLV-27-NR-R, central wavelength: 627 nm) fixed in the flow-type measuring cell was used as a light source to irradiate the surface of the working electrode with light, and the current flowing between the working electrode and the platinum counter electrode was measured with time. The measurement was made for 180 seconds, but the light irradiation was conducted only for 60 seconds, beginning 60 seconds after the time when the current measurement had been started. The observed current values were corrected by subtracting the value after a lapse of 180 seconds from the value after a lapse of 120 seconds.

Figure 23:
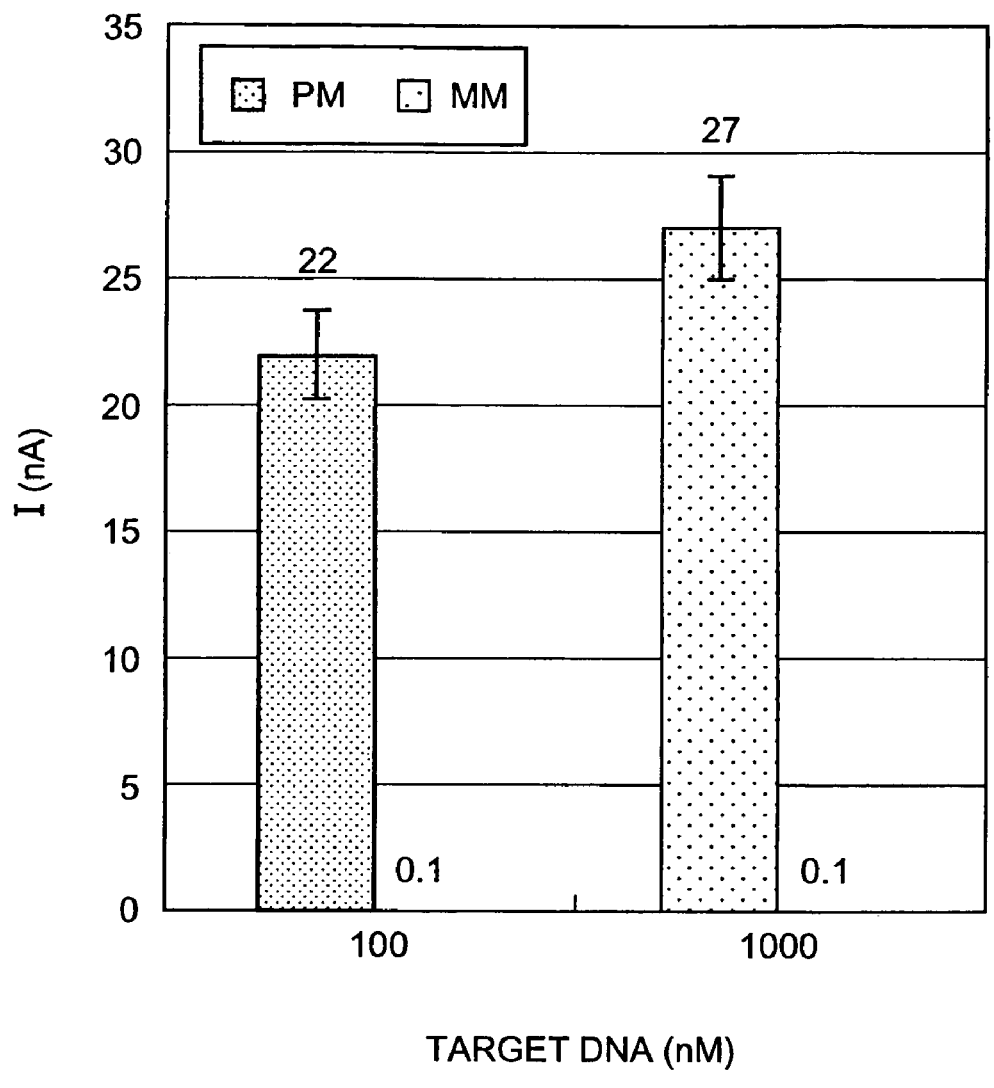
FIG. 23 is a graph showing a difference between the detected current values of complementary DNA and non-complementary DNA measured in Example 2, wherein PM indicates the use of DNA complementary to the probe and MM indicates the use of DNA non-complementary to the probe.

In consequence, as shown in FIG. 23, when the DNA complementary to the probe reacted, a current derived from the label dye (Cy5) was observed. On the other hand, with the non-complementary DNA caused to react, a current derived from Cy5 was not observed. It can be shown from this that a DNA sensor fabricated by the foregoing probe immobilization method is exceptional and highly sensitive.

Example 3

This example shows a difference between the current values of an electrolyte solution including metallic iodine and an electrolyte solution not including it, and shows that the electrolyte solution without the metallic iodine has the advantage over the other in the detection of single nucleotide conversion (SNPs). Specifically, an FTO glass was treated with the silane coupling agent to introduce an amino group onto the surfaces. The amino group and the probe DNA were bonded with electrostatic action to each other, followed by ultraviolet-ray irradiation to form a covalent bond to immobilize the probe on the electrode. This was hybridized with target DNA labeled with rhodamine, and then irradiated with exciting light, followed by measurement of the photocurrent to detect the single nucleotide conversion on the target. The details are as follows.

A fluorine-doped tin oxide (F—$SnO_2$:FTO) coated glass (produced by AI Tokushu Garasu Company, U-film, sheet resistance: 15Ω/□) was subjected to ultrasonic cleaning in an acetone, then in ultra-pure water including 0.1 vol % of Tween20, and further in ultra-pure water for 15 minutes each to remove contaminant and residual organic substance. This was shaken for 15 minutes in 5M aqueous sodium hydroxide. Then, for removing the sodium hydroxide, the shaking for 5 minutes in ultra-pure water was repeated three times, changing the water each time. The glass was taken out and air was blown on the glass to blow away the residual water, and then the glass was immersed in anhydrous methanol for hydroextraction.

The solution used in the coupling treatment was prepared by adding 2 vol % of 3-aminopropyltrimethoxysilane (APTMS) to a solvent comprising 95% methanol and 5% ultra-pure water and then stirring the mixture for 5 minutes at room temperature.

The above glass was immersed in this coupling treating solution and then slowly shaken for 15 minutes. Then, the glass was taken out and subjected to 3 sets of the process of shaking it approximately 10 times in methanol for removing the surplus coupling treating solution, changing the methanol for each process. Then, the glass was kept at 110° C. for 30 minutes to bond the coupling agent to the glass. After cooling it at room temperature, a spacer perforated (5 mm square) tape was affixed to the glass, and then tweezers were used to remove the air remaining on the adhesive surface of the tape. In addition, a silicone sheet having 5-mm-square openings formed therein was placed on and brought into close contact with the tape.

Next, the probe DNA prepared to 1 µM by being dissolved in 2×SSC (which is either one having a base sequence perfectly complementary to the target: 5'—NH2-AGGATGGGCCTCAGGTTCATGCCGC-3' or one being complementary to the target but having a different base: 5'—NH2-AGGATGGGCCTCGGGTTCATGCCGC-3') was maintained at 95° C. for 5 minutes, and then the probe DNA was immediately moved onto ice and maintained for 10 minutes to denature the DNA, 25 µl of which was then filled to spread uniformly to the openings on the glass which had undergone the foregoing treatment.

Then, this was maintained for one hour at 75° C. to vapor the solvent, and then the silicone sheet was peeled off. Then, a UV cross-linker (UVP Corporation, CL-1000 model) was used to irradiate the glass with 120 mJ of ultraviolet ray to provide a working electrode with the probe immobilized thereon.

This working electrode was subjected to 2 sets of the process of being shaken 10 times in ultra-pure water to remove the SSC component (NaCl and sodium citrate), changing the ultra-pure water for each process. Then, the electrode was immersed in boiling water for 2 minutes, taken out, and then aired to blow away the residual water. Then, the electrode was immersed in anhydrous ethanol at 4° C. for one minute for hydroextraction, and then aired to blow away the residual ethanol.

Next, target DNA adjusted to reach 10 nM of the concentration by being dissolved in a 5×SSC+0.5% SDS (Rho-DP53-t: 5'-Rho-GCGGCATGAACCTGAGGCCCATCCT-3') was maintained at 95° C. for 5 minutes, and then was immediately moved onto ice and maintained for 10 minutes to denature the DNA, 10 µl of which was then filled to spread uniformly to the openings on the glass which had undergone the foregoing treatments. Then, the glass was covered right from above with a prepared glass to prevent air bubbles from entering the DNA solution, was then housed in a plastic container in which the vapor pressure had been adjusted by moist paper or the like, and was then incubated overnight at 37° C.

After completion of the incubation, the prepared glass was removed and the working electrode was cleaned for approximately 2 seconds with ultra-pure water. Then, the electrode was propped against a slide-glass cleaning rack and cleaned in the following steps.
(1) 0.2×SSC+0.2% SDS
  63° C.
  Immersing for 3 Min. (Using a 5 L Water Tank)
(2) Shaking 10 times in ultra-pure water×2 sets with the solution changed each set
(3) Blowing air to remove the residual water The electrodes thus obtained were mounted in a flow-type measuring cell. Regarding the structure of the cell portion, the working electrode was placed opposite a platinum counter electrode so as to prevent the working electrode and the counter electrode from coming into contact with each other to make a short circuit, and additionally for the purpose of creating a space to be filled with an electrolytic solution, a 500 µm-thick silicone sheet was inserted. The silicone sheet had a hole of well over 5 mm square formed therein, into which the electrolytic solution was sent and stored so that the probe-immobilized face of the working electrode made contact with the electrolytic solution. The working electrode was electrically connected to a spring probe through which the working electrode was connected to a potentiostat (ALS Model 832A, PAS Kabushiki-Kaisha), while the platinum counter electrode was connected at one end with a lead wire through which the counter electrode was in connection to the potentiostat. As the electrolytic solution, the following two kinds were prepared.
(1) Electrolytic Solution A
  Tetrapropylammonium iodide 100 mM was dissolved in acetonitrile which was a solvent.
(2) Electrolytic Solution B
  Iodine 10 mM and tetrapropylammonium iodide 100 mM were dissolved in acetonitrile which was a solvent.

Each of these electrolyte solutions was filled into the space between the working electrode and the platinum counter electrode which had been mounted in the aforementioned flow-type measuring cell. Next, an LED (CCS Kabushiki-Kaisha, HLV-24GR-NR-3W, central wavelength: 530 nm, output power:67 mW) fixed in the flow-type measuring cell was used as a light source to irradiate the surface of the working electrode with light, and the current flowing between the working electrode and the platinum counter electrode was measured with time. The measurement was made for 180 seconds, but the light irradiation was conducted only for 60 seconds, beginning 60 seconds after the time when the current measurement had been started. The observed current values were corrected by subtracting the value after a lapse of 180 seconds from the value after a lapse of 120 seconds.

Figure 24A:
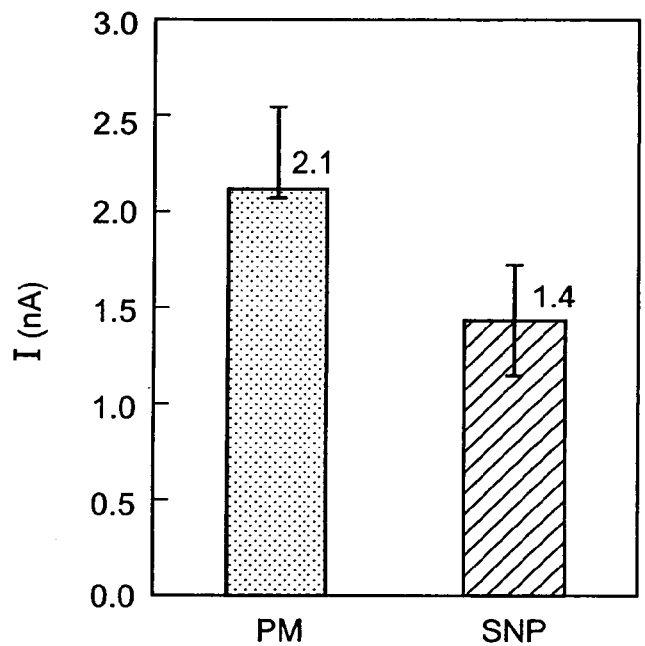
FIGS. 24A and 24B are graphs showing the detected current values measured in Example 3.
Figure 24B:
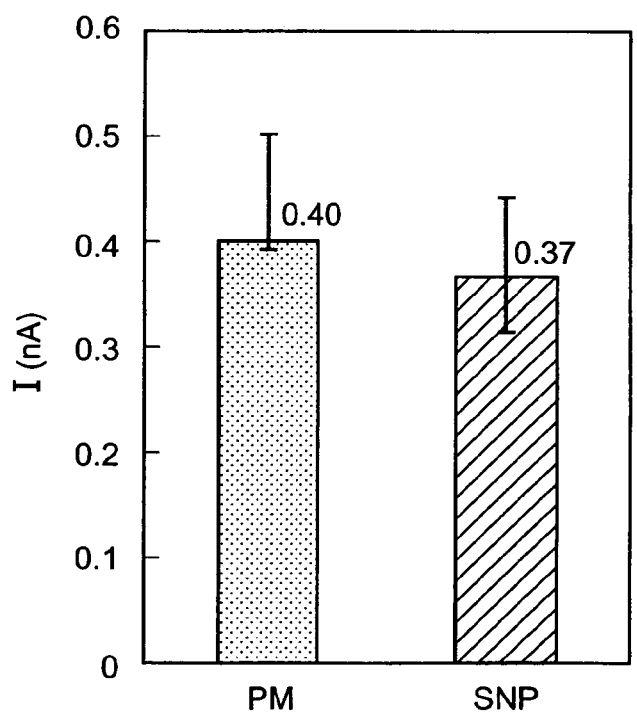

In consequence, FIGS. 24A and 24B respectively show the current values measured in the use of the electrolytic solution A without iodine and the electrolytic solution B with iodine. As shown in FIGS. 24A and 24B, by comparing the electrode on which a perfectly complementary strand is immobilized (PM in FIGS. 24A and 24B) with the electrode on which a complementary stand having a different base is immobilized (SNP in FIGS. 24A and 24B), it is statistically shown that there is a significant difference in the average current value in the measurement on the electrolytic solution A (N number: 5, significance level: 1%). It is established from this that a single nucleotide polymorphism in a nucleic acid sequence can be detected by a current sensing chip using a dye-sensitization phenomenon.

In addition, in the measurement on the electrolytic solution B, the current values were lower than those in the case of the electrolytic solution A and there was no significant difference in the average current value (N number: 5, significance level: 1%). It can be recognized that the use of the electrolytic solution not comprising iodine is more suitable for measurement for detecting an extremely low current.

Example 4

This is an example of the detection of a single nucleotide conversion (SNPs) using a plurality of spots. Specifically, an FTO glass was treated with the silane coupling agent to introduce an amino group onto the surfaces. Probe DNA was caused to be supported on spots created on the working electrode, and two 5'-end-Cy5-labeled target DNAs having different bases at a certain position were respectively hybridized to the working electrode which was then cleaned in certain conditions. The working electrode and a counter electrode formed of platinum in the same plane as the working electrode were mounted in a cell. Then, the working electrode was irradiated with exciting light, followed by measurement of the photocurrent. The photocurrent was compared between the probe DNAs. The details are as follows.

Supporting Probe onto Electrode

A fluorine-doped tin oxide (F—$SnO_2$:FTO) coated glass (produced by AI Tokushu Garasu Company, U-film, sheet resistance: 15Ω/□) was subjected to ultrasonic cleaning in an acetone, then in ultra-pure water including 0.1 vol % of Tween20, and further in ultra-pure water for 15 minutes each to remove contaminant and residual organic substance. This was shaken for 15 minutes in 5M aqueous sodium hydroxide. Then, for removing the sodium hydroxide, the shaking for 5 minutes in ultra-pure water was repeated three times, changing the water each time. The glass was taken out and air was blown on the glass to blow away the residual water, and then the glass was immersed in anhydrous methanol for hydroextraction.

The solution used in the coupling treatment was prepared by adding 2 vol % of 3-aminopropyltrimethoxysilane (APTMS) to a solvent comprising 95% methanol and 5% ultra-pure water and then stirring the mixture for 5 minutes at room temperature.

The above glass was immersed in this coupling treating solution and then slowly shaken for 15 minutes. Then, the glass was taken out and subjected to 3 sets of the process of shaking it approximately 10 times in methanol for removing the surplus coupling treating solution, changing the methanol for each process. Then, the glass was kept at 110° C. for 30 minutes to bond the coupling agent to the glass. After cooling it at room temperature, a spacer perforated tape (hole: φ=3 mm×6 spots, thickness:50 μm) was affixed to the glass. A silicone sheet (thickness: 1 mm) having the number of openings of φ=3 mm equal to the number of spots was placed on and brought into close contact with the tape.

Next, the probe DNA prepared to 1 μM by being dissolved in 2×SSC (5'—NH2-AGGATGGGCCTCAGGTTCATGC-CGC-3' produced by Proligo LLC) was maintained at 95° C. for 5 minutes, and then the probe DNA was immediately moved onto ice and maintained for 10 minutes to denature the DNA, 7 μl of which was then filled to the opening on each spot.

Then, this was maintained for one hour at 75° C. to vapor the solvent, and then the silicone sheet was peeled off. Then, a UV cross-linker (UVP Corporation, CL-1000 model) was used to irradiate the glass with 120 mJ of ultraviolet ray to provide a working electrode with the probe DNA immobilized thereon.

This working electrode was subjected to 2 sets of the process of being shaken 10 times in ultra-pure water to remove the SSC component (NaCl and sodium citrate), changing the ultra-pure water for each process. Then, the electrode was immersed in boiling water for 2 minutes, taken out, and then aired to blow away the residual water. Then, the electrode was immersed in anhydrous ethanol at 4° C. for one minute for hydroextraction, and then aired to blow away the residual ethanol.

Hybridization and Cleaning

Next, two kinds of 5'-end-Cy5-labeled target DNAs, that is, target DNA-1 perfectly complementary to the probe (5'-Cy5-GCGGCATGAACCTGAGGCCCATCCT-3' produced by Proligo LLC) and target DNA-2 in which the 13th T from the 5'-end was replaced with G (5'-Cy5-GCGGCATGAACCG-GAGGCCCATCCT-3' produced by Proligo LLC), were independently dissolved in a 5×SSC+0.5% SDS to be adjusted to reach 1 μM of the concentration. Then, the target DNAs were maintained at 95° C. for 5 minutes, and then 5 μl of the target DNA-1 was filled to each of the three spots, and 5 μl of the target DNA-2 was filled to each of the other three spots. Then, the glass was covered right from above with a prepared glass to prevent air bubbles from entering the DNA solution, was then housed in a plastic container in which the vapor pressure had been adjusted by moist paper or the like, and was then incubated overnight at 37° C.

After completion of the incubation, the prepared glass was removed and the electrode was propped against a slide glass. Then, the electrode was shaken for 3 minutes in a 2×SSC+ 0.1% SDS heated to 63° C., and then lightly shaken in ultra-pure water at ordinary temperature, and then air was blown to remove the residual water.

Measurement

The electrodes thus obtained were mounted in a flow-type measuring cell (example 2 of the device), on which an ARI-type stage (B05-41M produced by Suruga Seiki Kabushiki-Kaisha) for transferring the light source was attached. Regarding the structure of the cell portion, the working electrode and the platinum counter electrode were disposed in the same plane so as to prevent the working electrode and the counter electrode from coming into contact with each other to make a short circuit, and additionally for the purpose of creating a space to be filled with an electrolytic solution, a 500 μm-thick silicone sheet was inserted. The silicone sheet had a hole formed in a size enough for all the spots to fit inside, into which the electrolytic solution was sent and stored so that the DNA immobilized on the working electrode made contact with the electrolytic solution. The working electrode and the counter electrodes were electrically connected to a spring probe through which the working and counter electrodes were connected to a potentiostat (ALS Model 832A, PAS Kabushiki-Kaisha).

An electrolytic solution was prepared by dissolving tetra-propylammonium iodide 100 mM in acetonitrile. This electrolytic solution was filled into the aforementioned flow-type measuring cell.

Next, a red LED (CCS Kabushiki-Kaisha, HLV-27-NR-R, central wavelength: 627 nm) fixed in the light-source-transfer ARI type stage was used as a light source to irradiate the surface of the working electrode with light, and the current flowing between the working electrode and the platinum counter electrode was measured with time. The light source was moved by the ARI type stage to irradiate each of the spots with light. The measurement was made for 180 seconds, but the light irradiation was conducted only for 60 seconds from an elapse of 60 seconds after the time of starting the current measurement. The observed photocurrent was corrected by subtracting the photocurrent value after a lapse of 180 seconds from the photocurrent value after a lapse of 120 seconds.

In consequence, Table 2 shows the photocurrent values, the average value and a standard deviation (N number is 3) for each target DNA. By examining the difference between these average values, it was determined that there was a significant difference (significance level 5%). In other words, the difference in a single base pair between the target DNAs was able to be detected.

TABLE 2

|  |  | Target DNA-1 | Target DNA-2 |
| --- | --- | --- | --- |
| Photocurrent value (nA) | 1 | 0.45 | 0.32 |
|  | 2 | 0.42 | 0.22 |
|  | 3 | 0.31 | 0.24 |
| Average value (nA) |  | 0.39 | 0.26 |
| Standard deviation |  | 0.07 | 0.05 |

Example 5

This is an example of fabrication of a working electrode for immobilization of a dye-labeled single-stranded DNA.

A fluorine-doped tin oxide (F—$SnO_2$:FTO) coated glass (produced by AI Tokushu Garasu Company, U-film, sheet resistance: 12Ω/□, dimensions:50 mm×26 mm) was subjected to ultrasonic cleaning in an acetone, then in ultra-pure water including 0.1 vol % of Tween20, and further in ultra-pure water for 15 minutes each to remove contaminant and residual organic substance. This was shaken for 15 minutes in 5M aqueous sodium hydroxide. Then, for removing the sodium hydroxide, the shaking for 5 minutes in ultra-pure water was repeated three times, changing the water each time. The glass was taken out and air was blown on the glass to blow away the residual water, and then the glass was immersed in anhydrous methanol for hydroextraction.

The solution used in the coupling treatment was prepared by adding 2 vol % of 3-aminopropyltrimethoxysilane (APTMS) to a solvent comprising 95% methanol and 5% ultra-pure water and then stirring the mixture for 5 minutes at room temperature.

The above glass was immersed in this coupling treating solution and then slowly shaken for 15 minutes. Then, the glass was taken out and subjected to 3 sets of the process of shaking it approximately 10 times in methanol for removing the surplus coupling treating solution, changing the methanol for each process. Then, the glass was kept at 110° C. for 30 minutes to bond the coupling agent to the glass. After cooling it at room temperature, a PDMS sheet (thickness: 1.5 mm) having openings of ϕ=1 mm formed in 49 spots isolated every 1 mm was placed on and brought into close contact with the glass.

Next, the ssDNA (30 mer) labeled with rhodamine adjusted to 1 µM by being dissolved in 2×SSC was maintained at 95° C. for 5 minutes, then was immediately moved onto ice and maintained for 10 minutes to denature the DNA, 2 µl of which was then filled to each of the 49 openings formed in the PDMS sheet placed on the glass which had undergone the aforementioned treatment. Then, this was maintained for one hour at 75° C. to vapor the solvent, and then the PDMS sheet was peeled off. Then, a UV cross-linker (UVP Corporation, CL-1000 model) was used to irradiate the glass with 120 mJ of ultraviolet ray to provide a working electrode with the rhodamine-labeled ssDNA immobilized thereon.

Figure 25:
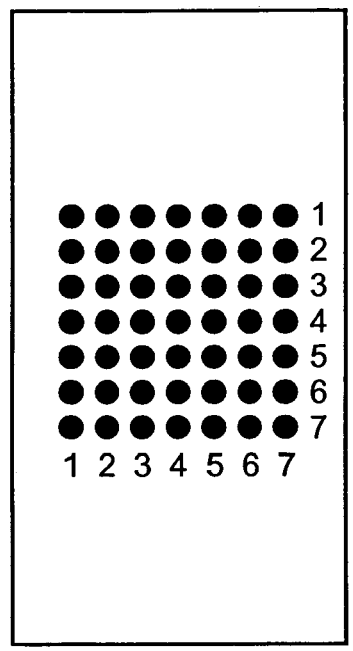
FIG. 25 is a schematic diagram illustrating a working electrode fabricated in Example 5 on which the DNA is immobilized in 49 locations.

This working electrode was subjected to 3 sets of the process of being soaked in a 0.2% SDS solution for 15 minutes, and then to the process of being shaken in ultra-pure water to remove the SSC component (NaCl and sodium citrate). Then, the electrode was immersed in boiling water for 2 minutes, taken out, and then aired to blow away the residual water. Then, the electrode was immersed in anhydrous ethanol at 4° C. for one minute for hydroextraction, and then aired to blow away the residual ethanol. FIG. 25 shows a schematic diagram of the working electrode immobilizing DNA in 49 spots thus obtained.

Example 6

This is an example of photocurrent detection using a mechanism for moving a light source in the X-Y direction to stop the light source at each spot region on the working electrode.

The working electrode fabricated by the method of Example 5 was mounted on the device having the light irradiation mechanism shown in FIG. 14, and the light source was stopped above the region on which a rhodamine-labeled ssDNA was immobilized and the photocurrent was measured. At this stage, a green laser diode having a luminous-flux diameter of 1 mm, a wavelength of 530 nm and an output power of 50 mW was used as the light source. During the light irradiation, 0.1M tetrapropylammonium iodide dissolved in acetonitrile was filled into the space between the counter electrode and the working electrode.

Figure 26:
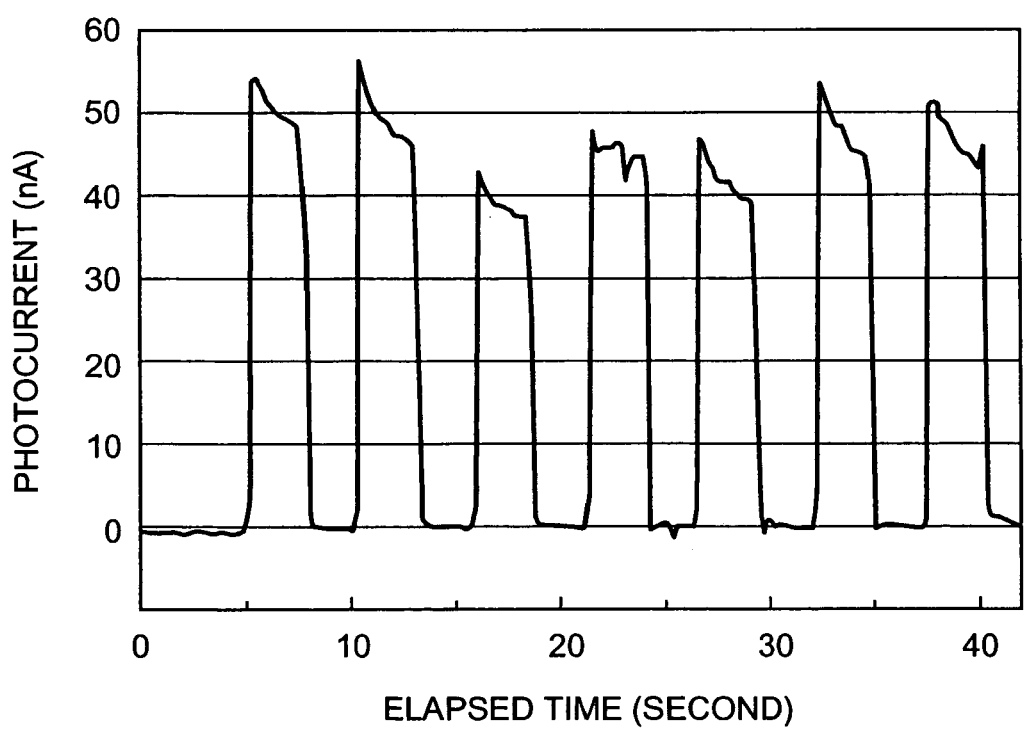
FIG. 26 is a graph showing the change with time in the photocurrent measured in Example 6.

FIG. 26 shows the results. The results shown in FIG. 26 are obtained in only one row of the immobilized DNA regions in 49 spots fabricated in Example 5. As is apparent from FIG. 26, the photocurrent values derived from the immobilized DNA regions are detected respectively as separated waveforms. The representative value for the photocurrent value readout may be either a value measured at a selected point during the light irradiation or the average value at a plurality of selected points. In either case, a preferable method is to collect data at regular time intervals for the duration of light irradiation.

Example 7

This is an example of detecting the photocurrents while a light source is continuously moved along the spot regions on the working electrode by use of a mechanism for moving the light source in the X-Y direction.

The working electrode fabricated by the method of Example 5 was mounted on the device having the light irradiation mechanism shown in FIG. 14, and the photocurrent was measured while the light source was continuously moved along the regions to which a rhodamine-labeled ssDNA was immobilized. At this stage, a green laser diode having a luminous-flux diameter of 1 mm, a wavelength of 530 nm and an output power of 50 mW was used as the light source. During the light irradiation, 0.1M tetrapropylammonium iodide dissolved in acetonitrile was filled into the space between the counter electrode and the working electrode.

Figure 27:
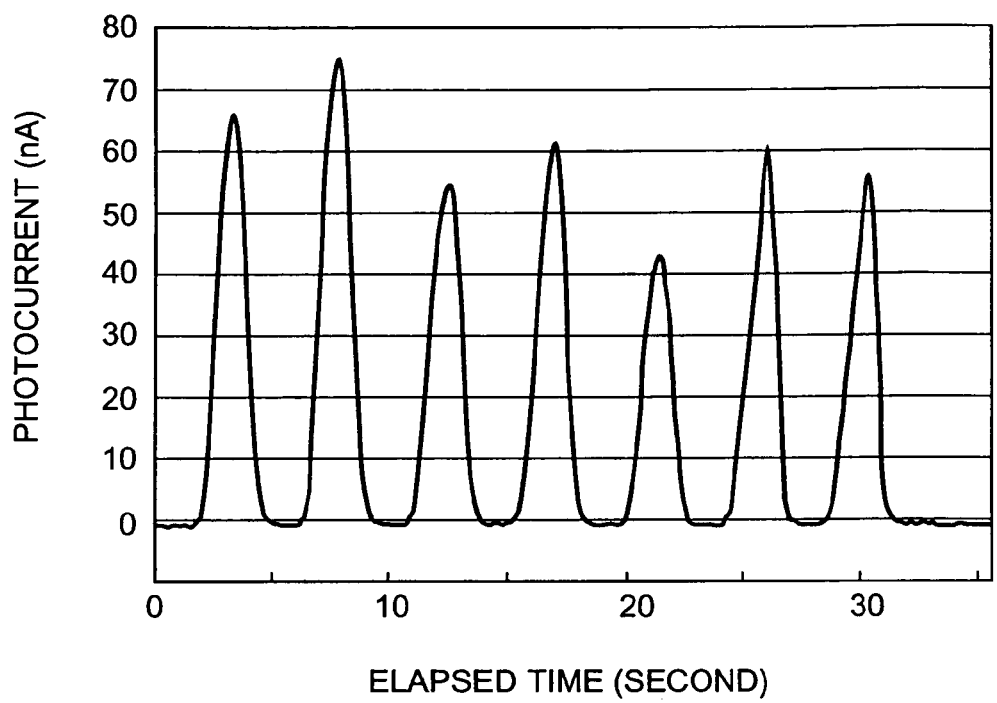
FIG. 27 is a graph showing the change with time in the photocurrent measured in Example 7.

FIG. 27 shows the results. The results shown in FIG. 27 are obtained in only one row of the immobilized DNA regions in 49 spots fabricated in Example 5. As is apparent from FIG. 26, the photocurrent values derived from the immobilized DNA regions are detected respectively as separated waveforms. For the photocurrent value readout, a simple and easy method is to use the highest value for the duration of light irradiation as the representative value.

Example 8

This is an example of photocurrent detection using a mechanism for moving a cell stage in the X-Y direction to stop the light source at each spot region on the working electrode.

The working electrode fabricated by the method of Example 5 was mounted on the device having the light irradiation mechanism shown in FIG. 15, and the light source was stopped at the region on which a rhodamine-labeled ssDNA was immobilized and the photocurrent was measured. At this stage, a green laser diode having a luminous-flux diameter of 1 mm, a wavelength of 530 nm and an output power of 50 mW was used as the light source. During the light irradiation, 0.1M tetrapropylammonium iodide dissolved in acetonitrile was filled into the space between the counter electrode and the working electrode.

Figure 28:
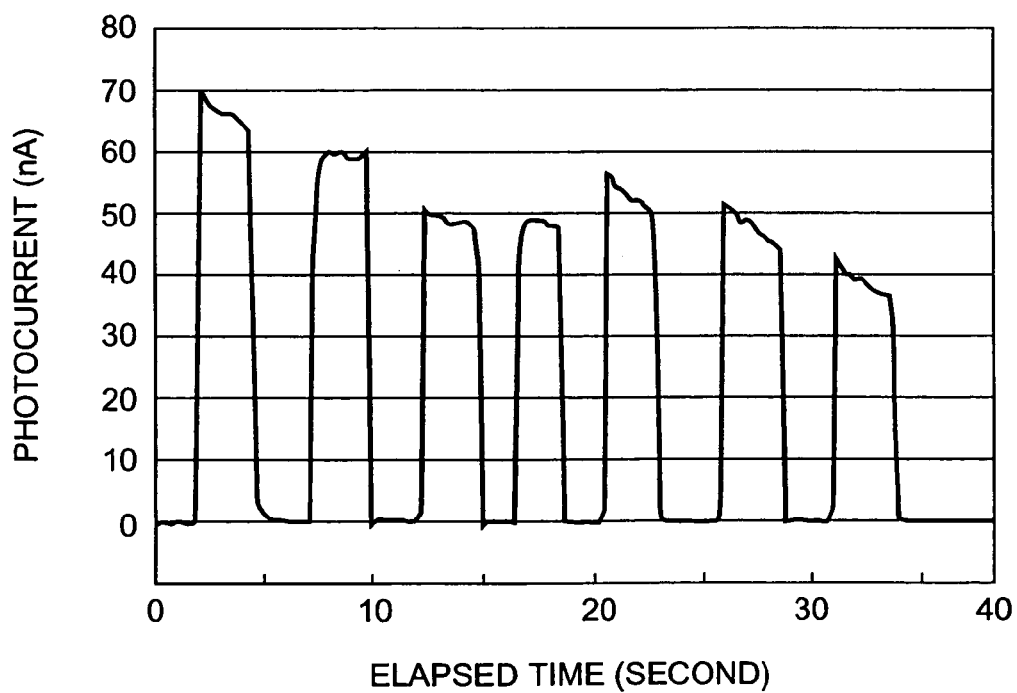
FIG. 28 is a graph showing the change with time in the photocurrent measured in Example 8.

FIG. 28 shows the results. The results shown in FIG. 28 are obtained in only one row of the immobilized DNA regions in 49 spots fabricated in Example 5. As is apparent from FIG. 28, the photocurrent values derived from the immobilized DNA regions are detected respectively as separated waveforms. The representative value for the photocurrent value readout may be either a value measured at a selected point during the light irradiation or the average value at a plurality of selected points. In either case, a preferable method is to collect data at regular time intervals for the duration of light irradiation.

Example 9

This is an example of detecting the photocurrents while a light source is continuously moved along the spot regions on the working electrode by use of a mechanism for moving a cell stage in the X-Y direction.

The working electrode fabricated by the method of Example 5 was mounted on the device having the light irradiation mechanism shown in FIG. 15, and the photocurrent was measured while the light source was continuously moved in a region on which a rhodamine-labeled ssDNA was immobilized. At this stage, a green laser diode having a luminous-flux diameter of 1 mm, a wavelength of 530 nm and an output power of 50 mW was used as the light source. During the light irradiation, 0.1M tetrapropylammonium iodide dissolved in acetonitrile was filled into the space between the counter electrode and the working electrode.

Figure 29:
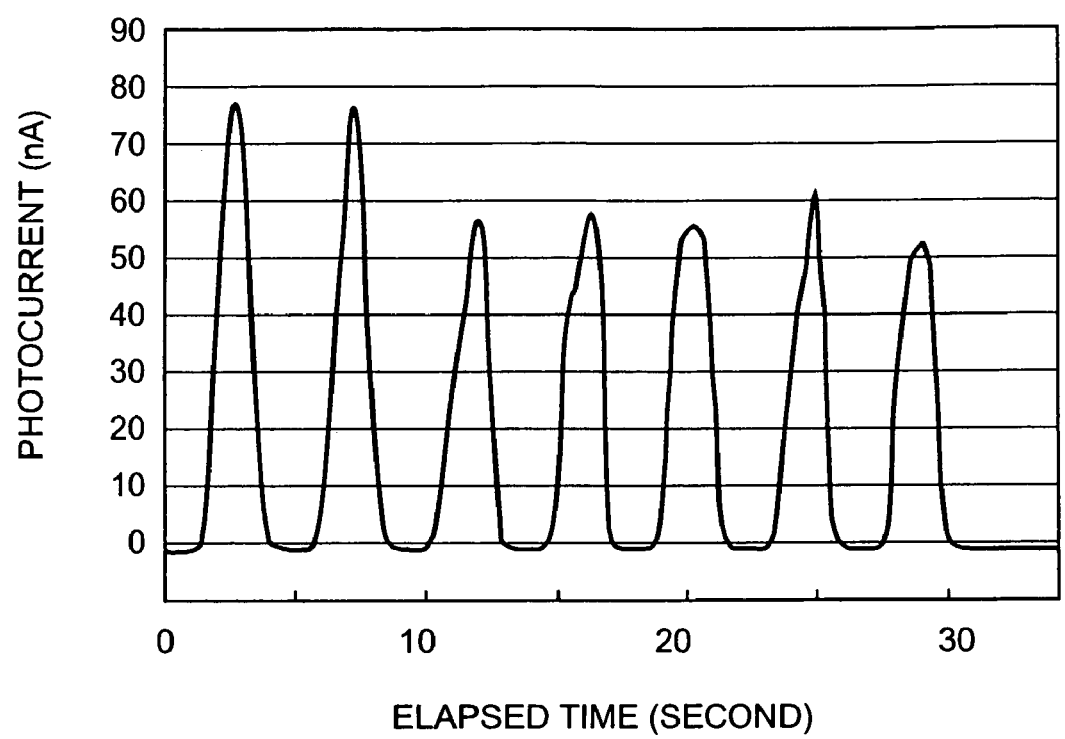
FIG. 29 is a graph showing the change with time in the photocurrent measured in Example 9.

FIG. 29 shows the results. The results shown in FIG. 29 are obtained in only one row of the immobilized DNA regions in 49 spots fabricated in Example 5. As is apparent from FIG. 29, the photocurrent values derived from the immobilized DNA regions are detected respectively as separated waveforms. For the photocurrent value readout, a simple and easy method is to use the highest value for the duration of light irradiation as the representative value.

Example 10

This is an example of detecting single nucleotide polymorphisms (SNPs) with an electrolyte solution using various electrolyte substances and aprotic solvents.

In this example, for the detection of single nucleotide polymorphisms in the p53 gene, a fluid mixture of acetonitrile and any one selected from the group consisting of NPr41(tetrapropylammonium iodide), sodium thiosulfate and sodium sulfite was used as the electrolyte solution. The concentration of the electrolyte substance was adjusted to 0.2M. A perfectly matching probe, a strand probe with a single nucleotide variation and a completely mismatching probe were immobilized on the working electrode. The following is the base sequences of the respective probes.

Perfectly Matching (PM) Probe:

5'-NH2-AGGATGGGCCTCAGGTTCATGCCGC-3'

Strand Probe with a Single Nucleotide Variation (SNP):

5'-NH2-AGGATGGGCCTCCGGTTCATGCCGC-3'

Completely Mismatching (MM) Probe:

5'-NH2-GCGGCATGAACCGGAGGCCCATCCT-3'

The following is a base sequence of a target DNA to be hybridized with these probes.

Target DNA:

5'-rhodamine-GCGGCATGAACCTGAGGCCCATCCT-3'

A fluorine-doped tin oxide (F—SnO$_2$:FTO) coated glass (produced by AI Tokushu Garasu Company, U-film, sheet resistance: 12Ω/□, dimensions:50 mm×26 mm) was subjected to ultrasonic cleaning in an acetone, then in ultra-pure water for 15 minutes each to remove contaminant and residual organic substance. This was shaken for 15 minutes in 5M aqueous sodium hydroxide. Then, for removing the sodium hydroxide, the shaking for 5 minutes in ultra-pure water was repeated three times, changing the water each time. The glass was taken out and air was blown on the glass to blow away the residual water.

The solution used in the coupling treatment was prepared by adding 2 vol % of 3-aminopropyltrimethoxysilane (APTMS) to a solvent comprising 95% methanol and 5% ultra-pure water and then stirring the mixture for 5 minutes at room temperature.

The above glass was immersed in this coupling treating solution and then slowly shaken for 15 minutes. Then, the glass was taken out and subjected to 3 sets of the process of shaking it approximately 10 times in methanol for removing the surplus coupling treating solution, changing the methanol for each process. Then, the glass was kept at 110° C. for 30 minutes to bond the coupling agent to the glass. After cooling it at room temperature, a self-adhesive seal (thickness: 0.5 mm) having openings of φ=3 mm formed in 9 spots was placed on and brought into close contact with the glass. Next, the perfectly matching strand probe, the strand probe with a single nucleotide variation and the completely mismatching strand probe (25 mer), which were prepared to 1 μM, were maintained at 95° C. for 10 minutes, then immediately moved onto ice and maintained for 10 minutes to denature the DNA, 5 μl of which were then filled to each of the 9 openings formed in the seal placed on the glass which had undergone the aforementioned treatment. The glass was maintained for 10 minutes at 95° C. to vapor the solvent. Then, a UV crosslinker (UVP Corporation, CL-1000 model) was used to irradiate the glass with 120 mJ of ultraviolet ray to immobilize the probe DNAs (each probe was immobilized in three spots).

Thereafter, the seal was peeled off and the glass was subjected to 3 sets of the process of being shaken in a 0.2% SDS solution for 15 minutes, and then rinsed three times in ultra-pure water, changing the water for each time. Then, the glass was immersed in boiling water for 2 minutes, taken out, and then aired to blow away the residual water. Then, the glass was immersed in anhydrous ethanol at 4° C. for one minute for hydroextraction, and then aired to blow away the residual ethanol.

Next, a 5×SSC, 0.5% SDS solution including the target DNA adjusted to reach 100 nM was placed on the electrode on which the probes had been immobilized, then was hermetically sealed with a cover glass, and then maintained at 37° C. for 10 hours. Then, the cover glass was removed in a 2×SSC at room temperature, and the electrode was propped against a rack. Then, the glass was shaken in a 2×SSC, 0.2% SDS solution at 40° C. for 30 minutes, then rinsed twice with water and then dried.

The electrode thus obtained was mounted in a measuring cell, on which an XY stage for automatically transferring the light source was attached. Regarding the structure of the cell portion, the working electrode and the platinum counter electrode were disposed opposite each other so as to prevent the working electrode and the counter electrode from coming into contact with each other to make a short circuit, and additionally for the purpose of creating a space to be filled with an electrolytic solution, a 500 μm-thick silicone sheet was inserted. The silicone sheet had a hole formed in a size enough for all the spots to fit inside, into which the electrolytic solution was sent and stored so that the DNA immobilized on the working electrode made contact with the electrolytic solution. The working electrode and the counter electrodes were electrically connected to a spring probe through which the working and counter electrodes were connected to a highly-sensitive ammeter.

Next, the back face of the working electrode was irradiated from above with light by the light source fixed to the automatic transfer XY stage, and the current flowing between the working electrode and the platinum counter electrode was measured with time. Above the working electrode, a light blocking member having the same shape as that of the spot formed on the FTO substrate was provided for preventing the light from passing to a spot adjacent to the target spot and also for providing a non-irradiated spot. For the measurement, the spots were scanned in order and simultaneously the current output from the spot was stored to a personal computer through the highly-sensitive ammeter connected to the personal computer.

Figure 30:
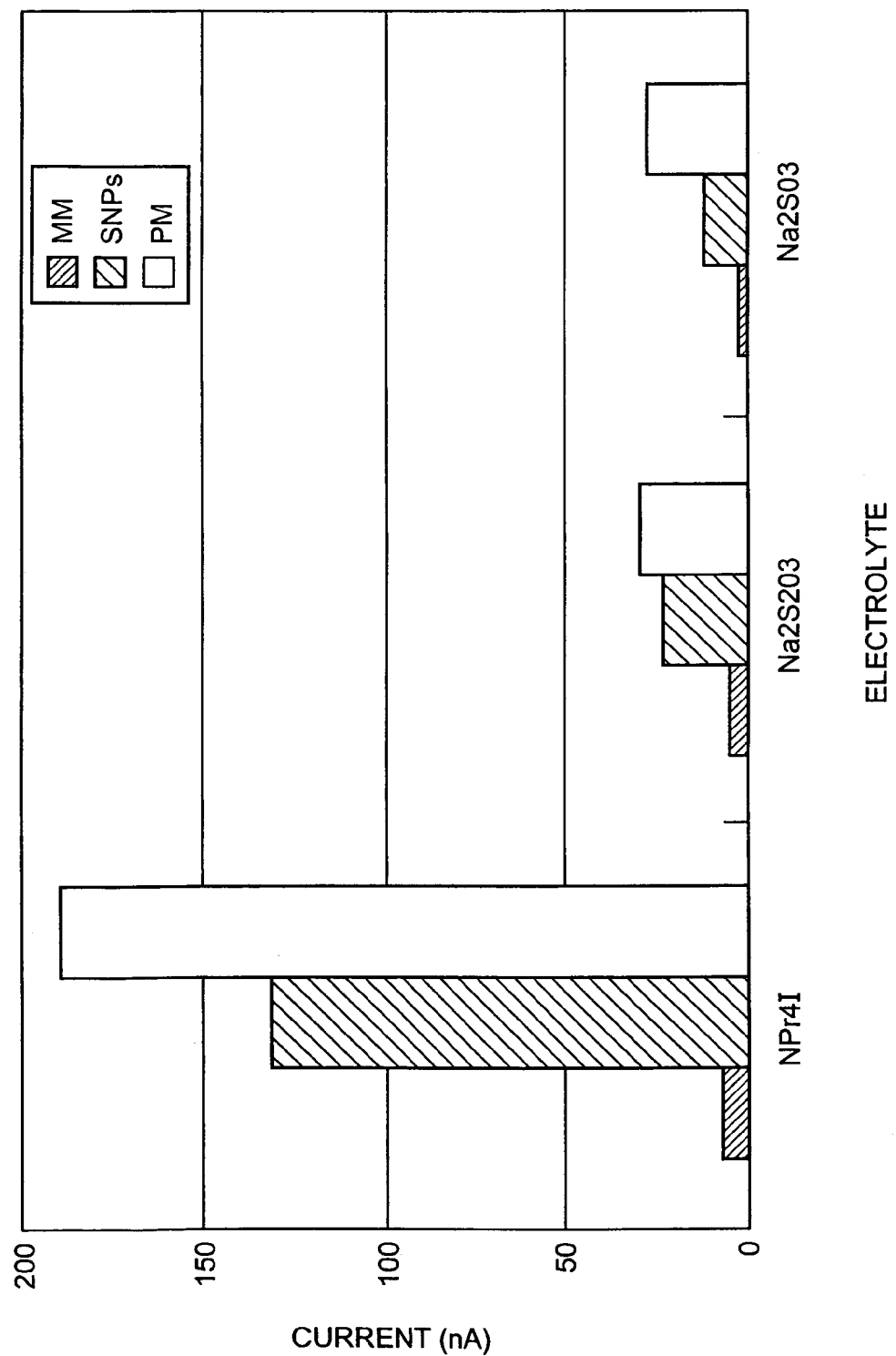
FIG. 30 is a graph showing the photocurrent values measured using various types of electrolytes in Example 10, wherein PM denotes a case of using a perfectly matching probe, SNP denotes a case of using a strand probe having a single nucleotide variation and MM denotes a case of using a completely mismatching probe.

FIG. 30 shows the results. As seen from the results of FIG. 30, single nucleotide polymorphisms (SNPs) were able to be detected as a difference of the photocurrent values even when an aprotic electrolyte solution was used.

Example 11

This is an example of using electrolyte solutions containing various concentrations of acetonitrile to detect single nucleotide polymorphisms (SNPs).

The measurement in this example was made in the same way as Example 10, except for use of, as an electrolyte solution, a fluid mixture including 0.2M NPr4I (tetrapropylammonium iodide) as an electrolyte substance, various concentrations of acetonitrile, and water for the detection of single nucleotide polymorphisms in the p53 gene.

Figure 31:
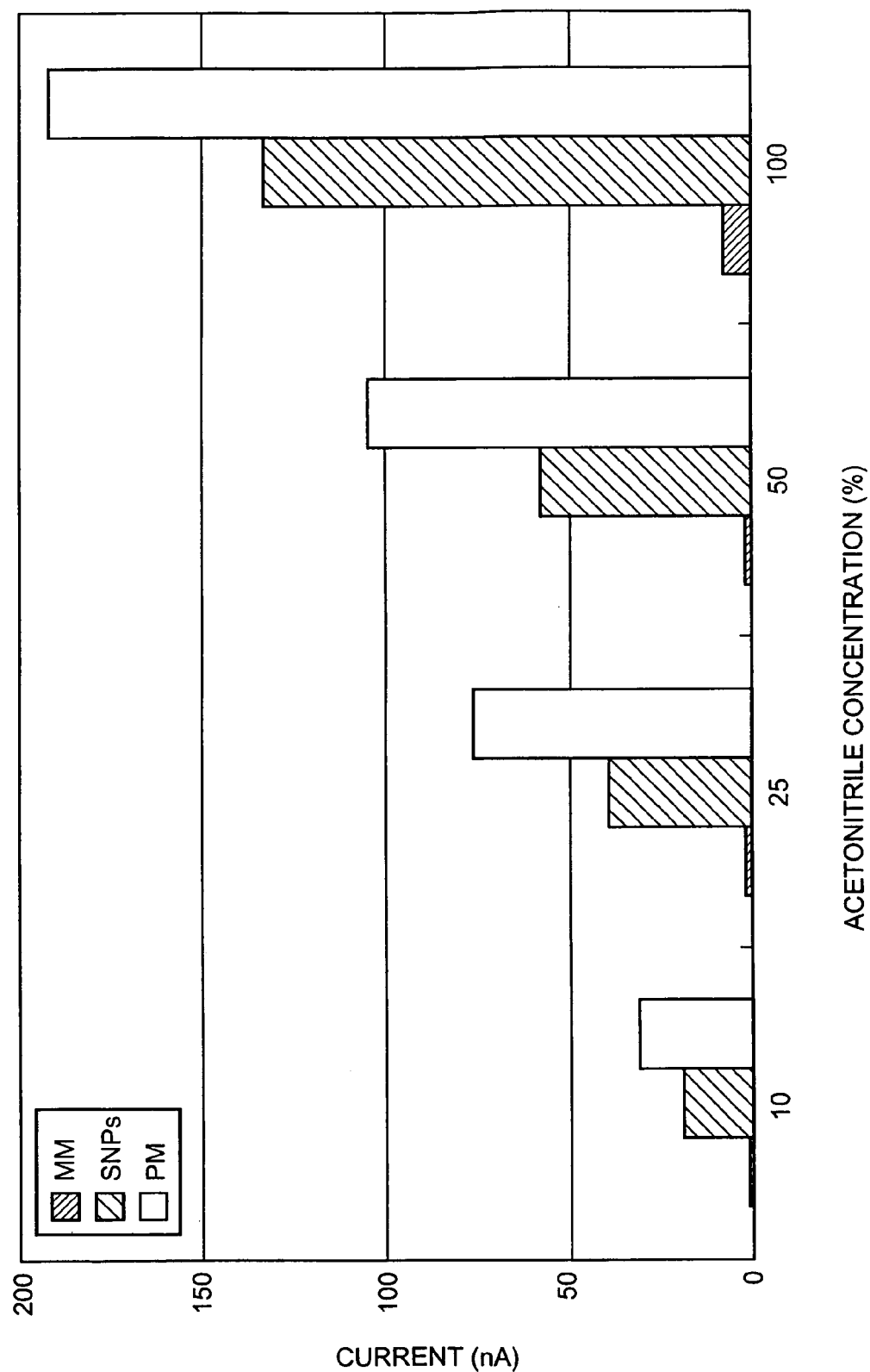
FIG. 31 is a graph showing the photocurrent values measured using various concentrations of acetonitrile in Example 11, wherein PM denotes a case of using a perfectly matching probe, SNP denotes a case of using a strand probe having a single nucleotide variation and MM denotes a case of using a completely mismatching probe.

FIG. 31 shows the results. As is apparent from the results in FIG. 31, single nucleotide polymorphisms (SNPS) were able to be detected as a difference of the photocurrent values even in the use of the electrolyte solution having an acetonitrile concentration of from 100% to 100%.

Example 12

This is an example of producing a working electrode for the immobilization of a dye-labeled single-stranded DNA.

A fluorine-doped tin oxide (F—$SnO_2$:FTO) coated glass (produced by AI Tokushu Garasu Company, U-film, sheet resistance: 12Ω/□, dimensions:50 mm×26 mm) was subjected to ultrasonic cleaning in an acetone, then in ultra-pure water for 15 minutes each to remove contaminant and residual organic substance. This was shaken for 15 minutes in 5M aqueous sodium hydroxide. Then, for removing the sodium hydroxide, the shaking for 5 minutes in ultra-pure water was repeated three times, changing the water each time. The glass was taken out and air was blown on the glass to blow away the residual water, and then it was immersed in anhydrous methanol for dehydration.

The solution used in the coupling treatment was prepared by adding 2 vol % of 3-aminopropyltrimethoxysilane (APTMS) to a solvent comprising 95% methanol and 5% ultra-pure water and then stirring the mixture for 5 minutes at room temperature.

The above glass was immersed in this coupling treating solution and then slowly shaken for 15 minutes. Then, the glass was taken out and subjected to 3 sets of the process of shaking it approximately 10 times in methanol for removing the surplus coupling treating solution, changing the methanol for each process. Then, the glass was kept at 110° C. for 30 minutes to bond the coupling agent to the glass. After cooling it at room temperature, a self-adhesive seal (thickness: 0.5 mm) having openings of φ=3 mm formed in 9 spots was placed on and brought into close contact with the glass. Next, the ssDNAs (25 mer) labeled with rhodamine of adjusted concentrations (100 nM, 10 nM, 0 nM) were maintained at 95° C. for 10 minutes, then were immediately moved onto ice and maintained for 10 minutes to denature the DNA, 5 μl of which were then filled to each of the 9 openings formed in the seal placed on the glass which had undergone the aforementioned treatment. Then, the glass was maintained for 10 minutes at 95° C. to vapor the solvent. Then, a UV cross-linker (UVP Corporation, CL-1000 model) was used to irradiate the glass with 120 mJ of ultraviolet ray to immobilize labeled ssDNAs.

Then, the seal was peeled off and the glass was subjected to 3 sets of the process of being shaken in a 0.2% SDS solution for 15 minutes, and then rinsed three times in ultra-pure water, changing the water for each time. Then, the glass was immersed in boiling water for 2 minutes, taken out, and then aired to blow away the residual water. Then, the glass was immersed in anhydrous ethanol at 4° C. for one minute for hydroextraction, and then aired to blow away the residual ethanol.

Example 13

This is an example of dye-labeled single-stranded DNA with an electrolyte solution using various electrolyte substances and water.

In this example, for the detection of rhodamine-labeled ssDNA (30 mer), a fluid mixture of water and any one selected from the group consisting of NaI, KI, $CaI_2$, LiI, $NH_4I$, $NPr_4I$ (tetrapropylammonium iodide), sodium thiosulfate and sodium sulfite was used as the electrolyte solution. The concentration of the electrolyte substance was 0.2M. As for the steps of the detection, the working electrode fabricated by the method of Example 12 was mounted in a device having the light irradiation mechanism shown in FIG. 2, and then the light source was stopped at the region on which the rhodamine-labeled ssDNA was immobilized, and then the photocurrent was measured. In this detection, the concentrations of the ssDNA to be immobilized were three, 0 nM, 10 nM and 100 nM.

Figure 32:
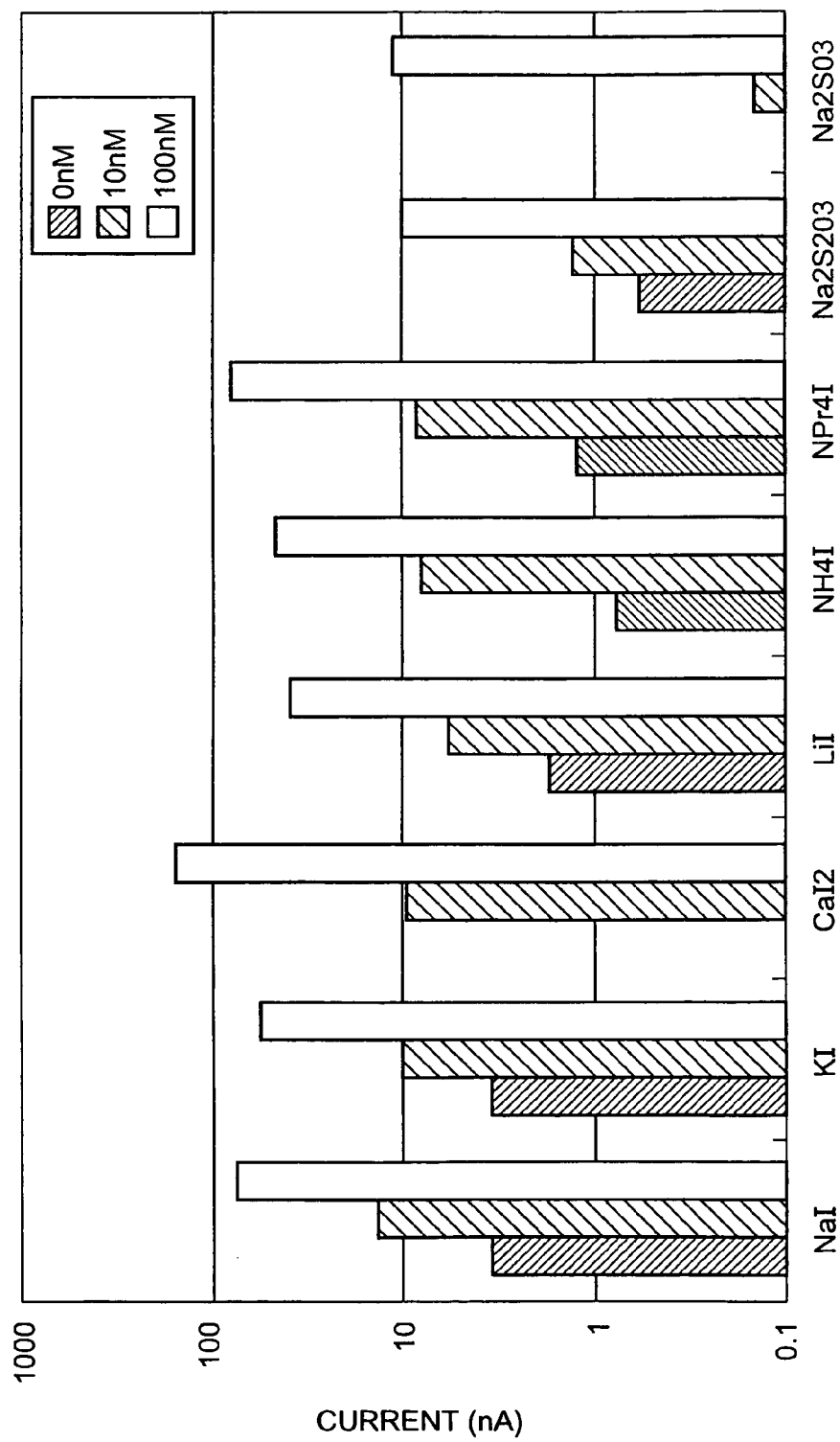
FIG. 32 is a graph showing the photocurrent values measured using various types of electrolytes in Example 13.

FIG. 32 shows the results. As is apparent from the results in FIG. 32, an increase in photocurrent dependent on the amount of ssDNA immobilized is recognized even in the use of any electrolyte which has been studied. In consequence, it is apparent that it is possible to use all the electrolytes studied.

Example 14

This is an example of using a fluid mixture including water and NPr$_4$I (tetrapropylammonium iodide) as an electrolyte solution to detect single nucleotide polymorphisms (SNPs).

The measurement in this example was made in the same way as Example 10, except for use of, as an electrolyte solution, a fluid mixture including 0.2M NPr4I (tetrapropylammonium iodide) as an electrolyte substance and water for the detection of single nucleotide polymorphisms in the p53 gene.

Figure 33:
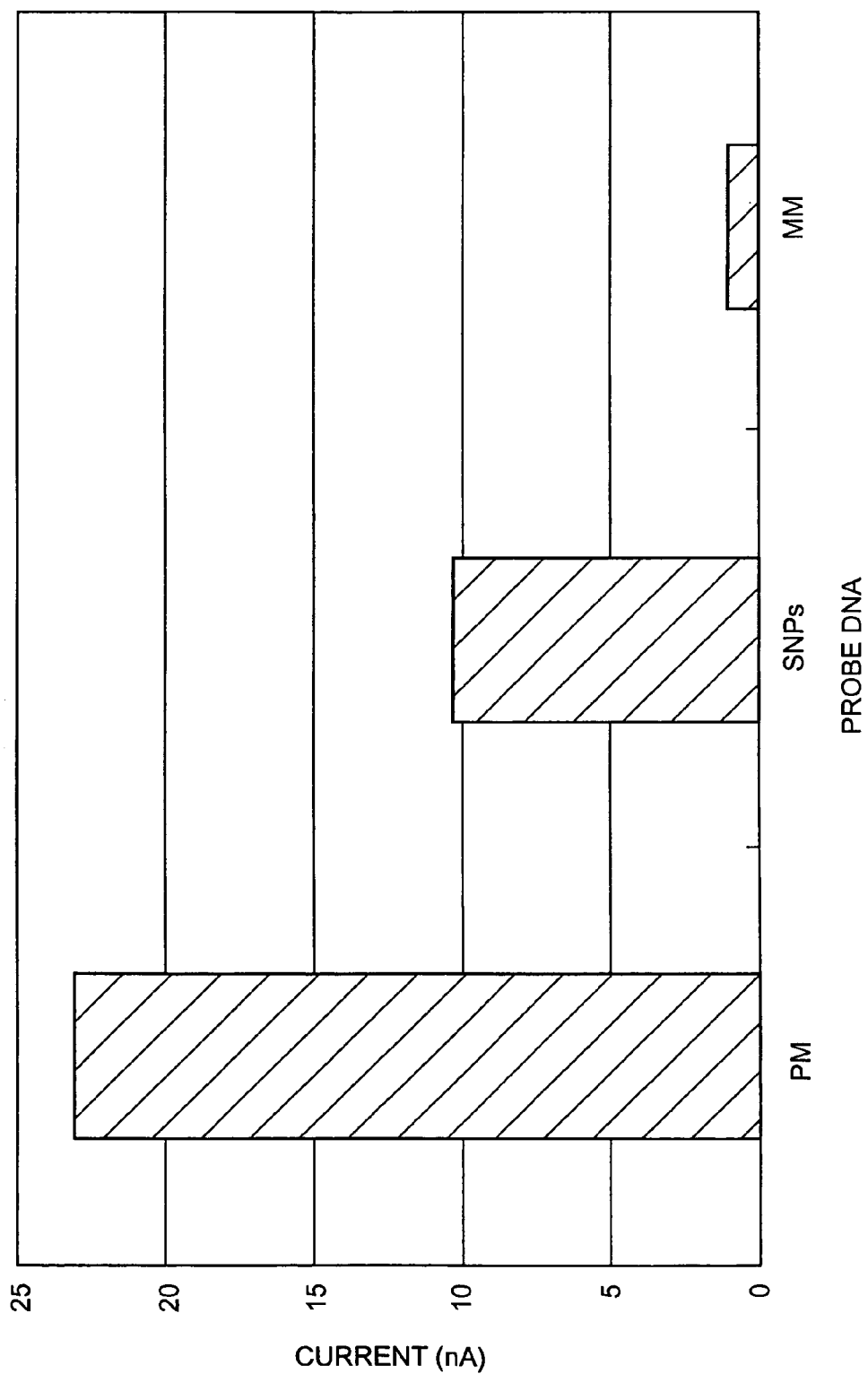
FIG. 33 is a graph showing the photocurrent values of single nucleotide polymorphisms (SNPs) measured by the use of an aqueous electrolytic solution in Example 14.

FIG. 33 shows the results. As is apparent from the results in FIG. 33, single nucleotide polymorphisms (SNPs) were able to be detected as a difference of the photocurrent values even in the use of the electrolyte solution of the aqueous solution system.

Example 15

This is an example of detecting a dye-labeled protein through dye-sensitized biosensor technology.
Silane Coupling Treatment on FTO Glass A fluorine-doped tin oxide (F—SnO$_2$:FTO) coated glass (produced by Al Tokushu Garasu Company, U-film, sheet resistance: 15Ω/□) was subjected to ultrasonic cleaning in an acetone, then in ultra-pure water including 0.1 vol % of Tween20, and further in ultra-pure water for 15 minutes each to remove contaminant and residual organic substance. Then, this was shaken for 15 minutes in 5M aqueous sodium hydroxide. Then, for removing the sodium hydroxide, the shaking for 5 minutes in ultra-pure water was repeated three times, changing the water each time. The FTO glass was taken out and air was blown on the glass to blow away the residual water, and then the glass was immersed in anhydrous methanol for hydroextraction. Air was blown on the glass to blow away the methanol to dry the FTO glass.

The solution used in the coupling treatment was prepared by adding 2 vol % of 3-aminopropyltrimethoxysilane (APTMS: produced by AVOCADO Company) to a solution mixture comprising 95 vol % methanol and 5 vol % ultra-pure water and then stirring it for 5 minutes at room temperature.

The above FTO glass was immersed in this coupling treating solution and then slowly shaken for 15 minutes. Then, the FTO glass was taken out and subjected to 3 sets of the process of shaking it approximately 10 times in anhydrous methanol for removing the surplus coupling treating solution, changing the anhydrous methanol for each process. Then, the glass was kept at 110° C. for 30 minutes to bind the coupling agent to the glass. After cooling it at room temperature, a spacer perforated tape (hole: φ=3 mm×6 spots, thickness: 50 μm) was affixed to the glass.
Immobilization of Oligo DNA A 5'-end-biotin-labeled oligo DNA or non-labeled oligo DNA (produced by Proligo LLC: sequence is 5'-TggCTCCT-gACCTggAgTCTTCCAgTgTgA-3') was adjusted to 1 μM by being dissolved into ultra-pure water, then maintained at 95° C. for 5 minutes to denature the DNA, 7 μl of which was then dripped to the tape opening (spot electrode). Then, this was maintained for 10 minutes at 95° C. to be dried. Then, a UV cross-linker (UVP Company, CL-1000 model) was used to irradiate the glass with 120 mJ of ultraviolet ray to provide a working electrode with the oligo DNA immobilized thereon.

This working electrode was subjected to 3 sets of the process of being shaken in a 0.2% SDS solution for 15 minutes, changing the solution for each process. Then, the working electrode was cleaned by being shaken approximately ten times in ultra-pure water to remove the SDS, changing the water 3 times. Then, the electrode was immersed in boiling water for 2 minutes, taken out, and then aired to blow away the residual water. Then, the electrode was immersed in anhydrous ethanol at 4° C. for one minute for hydroextraction, and then aired to blow away the residual ethanol.
Rhodamine-Labeled Protein Incubation and Cleaning Streptavidin labeled with rhodamine by the use of a kit commercially available from Molecular Probes Company (labeling ratio: 3.1) was diluted to 10 ug/ml with a buffer solution (10 mM HEPES pH7.4+150 mM NaCl+0.05% Tween20).

The protein solution 7 μl was dripped to the spot electrode, and then a prepared glass was placed thereon, which was then incubated at 37° C. for one hour.

After completion of the incubation, the prepared glass was removed and the working electrode was propped against a rack, which was then sunk in a staining vat filled with the above-mentioned buffer solution, and then cleaned by being shaken approximately 10 times with changing the buffer solution 3 times. It should be noted that the working electrode was immersed in the buffer solution until just before the measurement.
Measurement The working electrode thus obtained was lightly shaken in ultra-pure water immediately before the measurement, then was aired to blow away the residual water before being mounted in a flow-type measuring cell. In the cell the working electrode and the platinum counter electrode were disposed opposite each other between which a 500 μm-thick silicone sheet was inserted. The silicone sheet had a hole formed in a size enough for all the spot electrodes to fit inside, into which the electrolytic solution was sent and stored so that the spot electrode made contact with the electrolytic solution. The electrolyte solution used was a fluid mixture of a 1M sodium thiosulfate and a 0.1M salt solution. The working electrode and the counter electrodes were electrically connected respectively to spring probes through which the working and counter electrodes were connected to an ammeter (produced by ADVANTEST Company: R8240).

A light blocking member having openings corresponding to the respective spots was placed over the flow-type measuring cell and the electrolyte solution was filled. Then, a movable laser light source (central wavelength: 532 nm) provided on the light-blocking member irradiated the spots in order, and the current flowing between the working electrode and the platinum counter electrode was measured with time. Each of the spots was irradiated for 5 seconds. The correction was made by subtracting the base current value from the photocurrent value after a lapse of 5 seconds.

Figure 34:
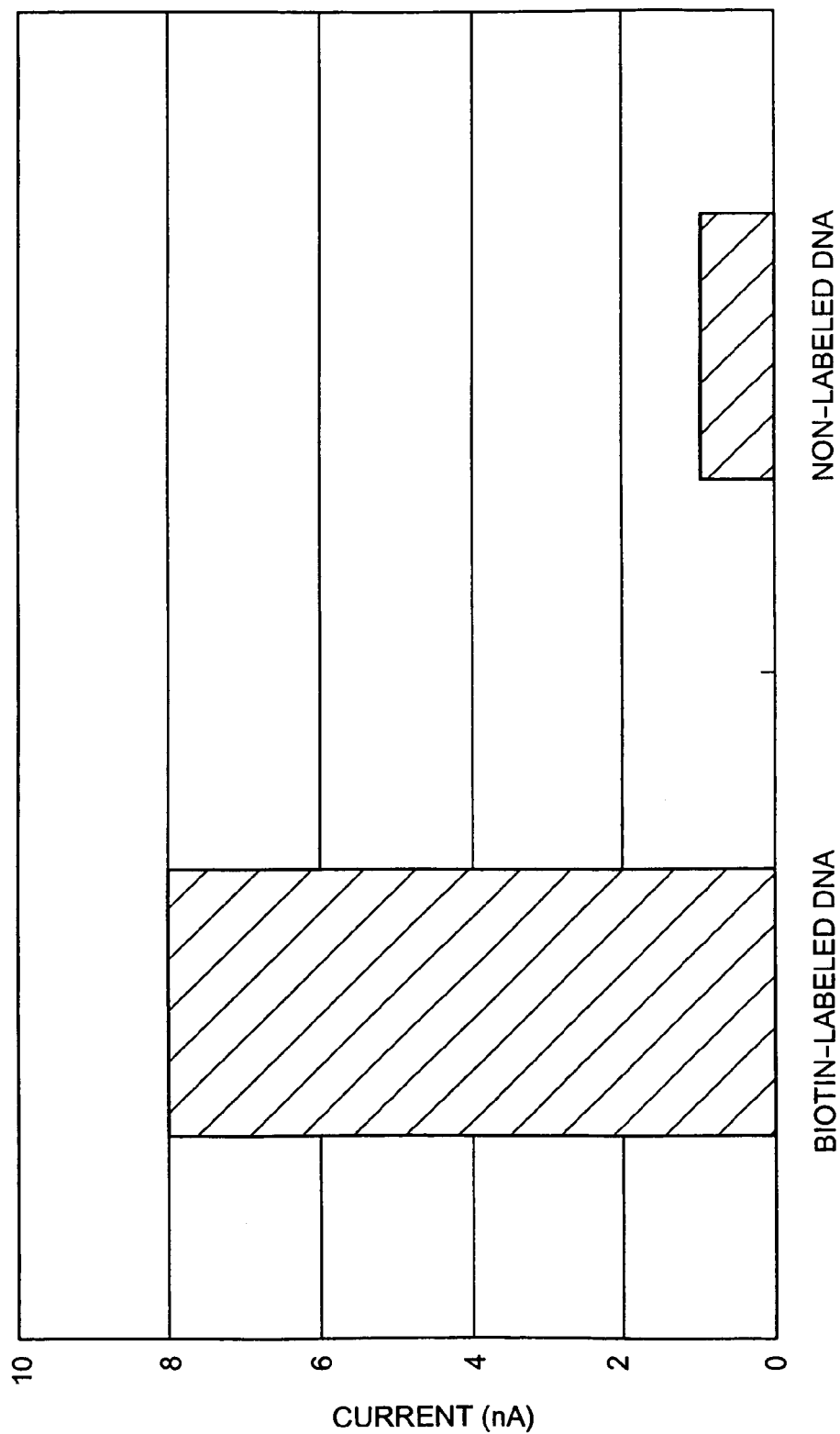
FIG. 34 is a graph showing the respectively measured photocurrent values of rhodamine labeled protein and non-labeled protein in Example 16.

FIG. 34 shows the results. As is seen from the results in FIG. 34, it could be demonstrated that the detection of protein was achieved by use of dye-sensitized biosensor technology.

Example 17

This is an example of dye-labeled single-stranded DNA with an electrolyte solution using various electrolyte substances and water.

In this example, for the detection of rhodamine-labeled ssDNA (30 mer), a fluid mixture including water and any one selected from the group consisting of hydroquinone, triethanolamine, potassium ferricyanide, and $NPr_4I$ (tetrapropylammonium iodide) was used as the electrolyte solution. The concentration of the electrolyte substance was 0.2M. As for the steps of the detection, the working electrode fabricated by the method of Example 12 was mounted in a device having the light irradiation mechanism shown in FIG. 14, and then the light source was stopped at the region on which the rhodamine-labeled ssDNA was immobilized, and then the photocurrent was measured.

Figure 35:
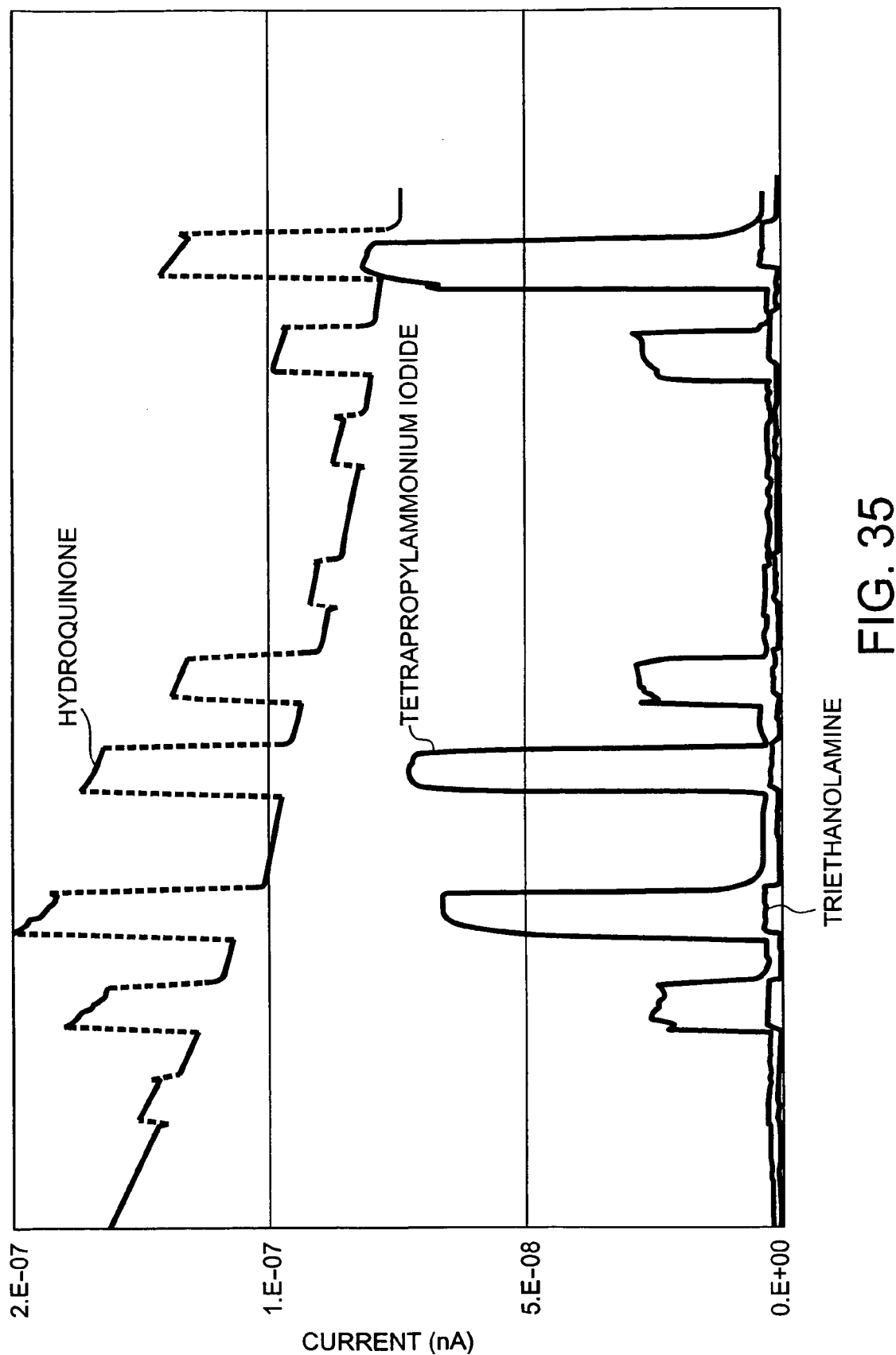
FIG. 35 is a graph showing the change with time of the measured photocurrent values of a liquid mixture of water and any one selected from the group consisting of hydroquinone, triethanolamine and $NPr_4I$ in Example 17.
Figure 36:
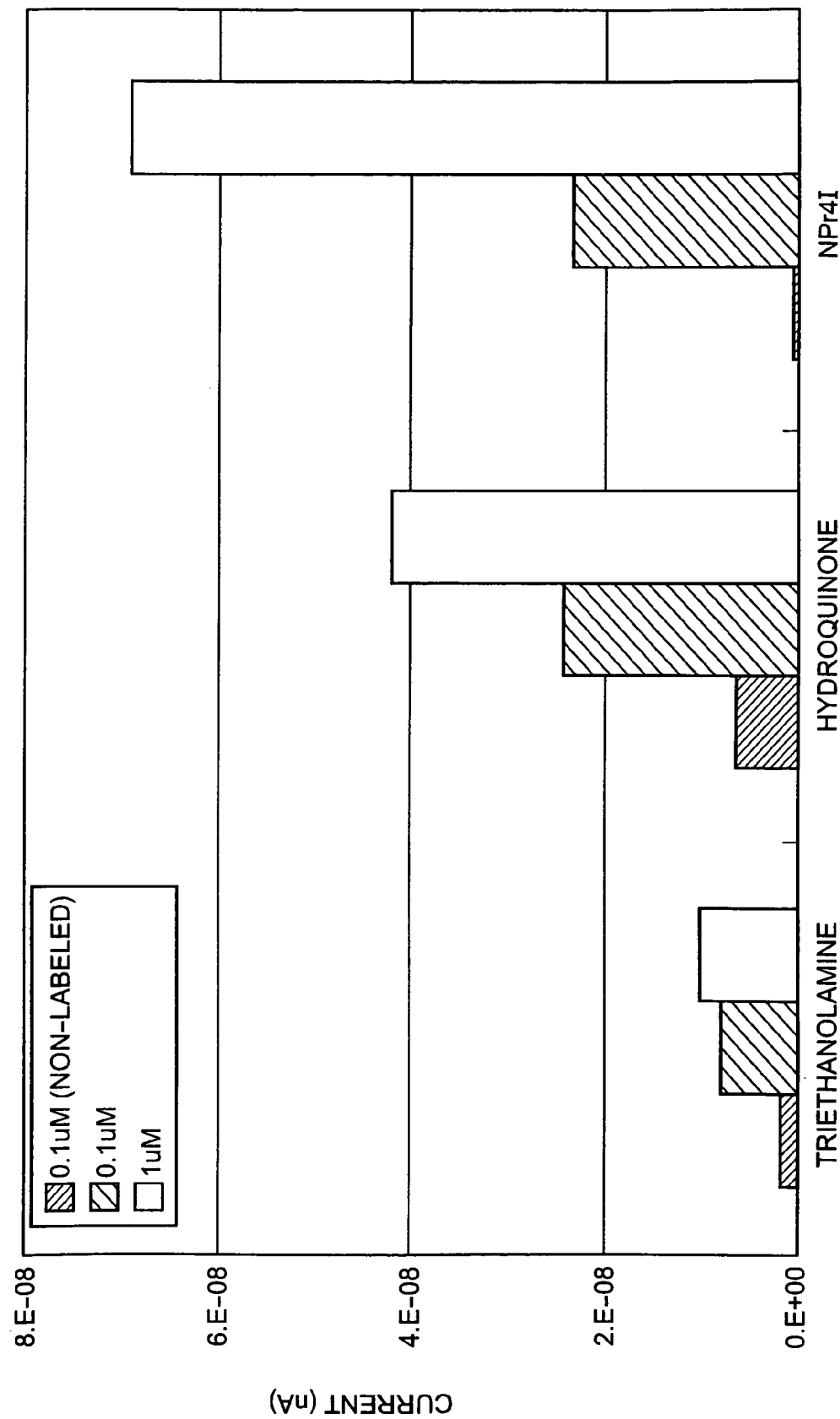
FIG. 36 is a graph showing the results obtained by data processing on the photocurrent obtained in FIG. 35.
Figure 37:
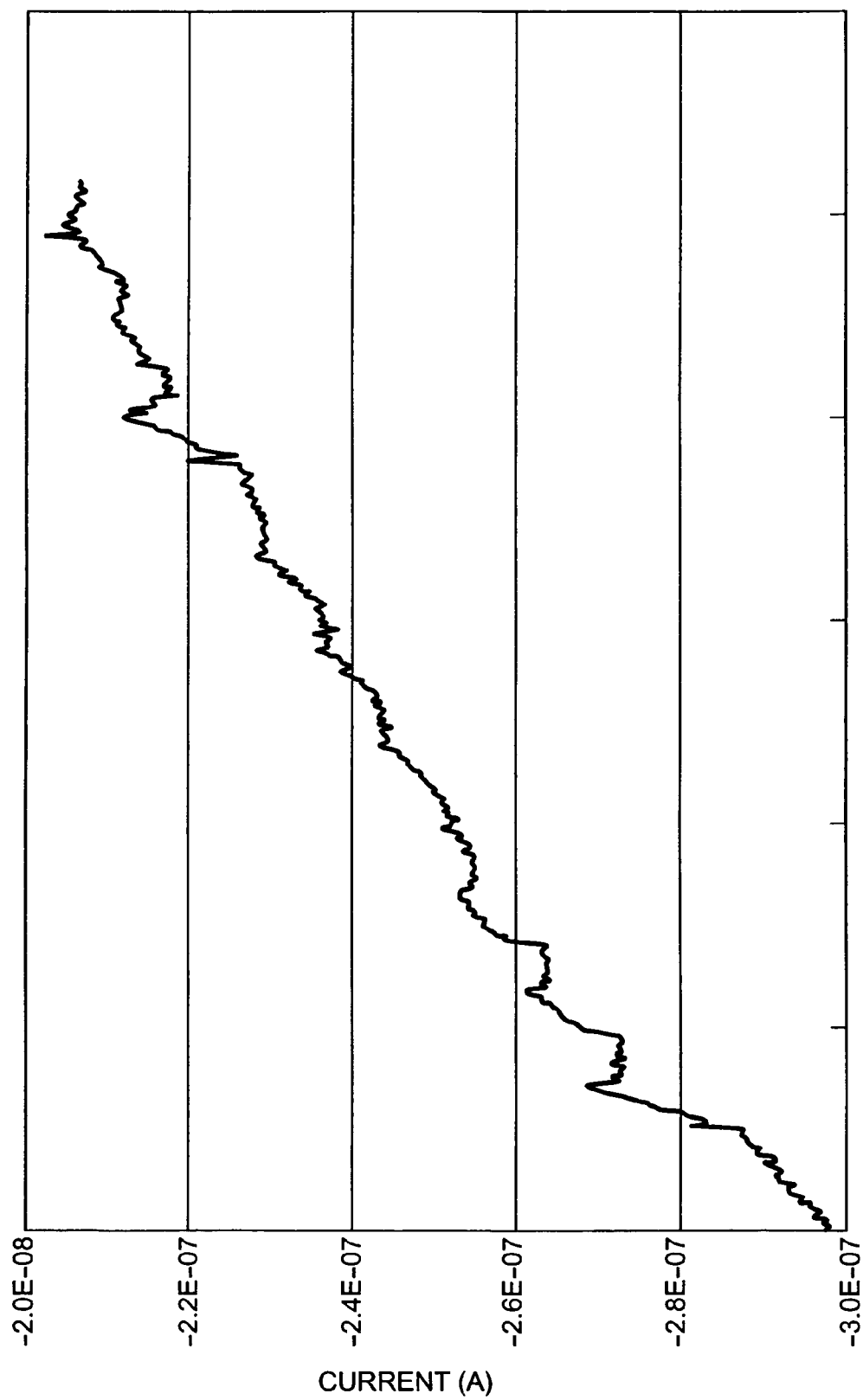
FIG. 37 is a graph showing the photocurrent waveform obtained by measuring a liquid mixture of potassium ferricyanide and water in Example 17 as an electrolytic solution.

FIG. 35 shows the photocurrent waveforms obtained when the fluid mixture including water and any one selected from the group consisting of hydroquinone, triethanolamine and $NPr_4I$ was used as an electrolyte solution. FIG. 36 shows the results obtained by data processing on the photocurrent obtained in FIG. 35. FIG. 37 shows the photocurrent waveforms obtained when the fluid mixture including water and potassium ferricyanide was used as an electrolyte solution. From the results in FIGS. 35 and 36, when hydroquinone or $NPr_4I$ was used, an increase in photocurrent dependent on the amount of ssDNA immobilized was recognized, but when triethanolamine was used, an extremely weak photocurrent was detected merely. However, as is apparent from FIG. 35, in the use of hydroquinone, since the electric current was unstable and also the noise current was high, hydroquinone was not suitable for accurate detection. As shown in FIG. 37, in the use of potassium ferricyanide, the electric current was unstable and the photocurrent was little detected. From these results, it turned out that only $NPr_4I$ (tetrapropylammonium iodide) was suitable for highly accurate detection among the various electrolyte substances including hydroquinone, triethanolamine, potassium ferricyanide, and $NPr_4I$ (tetrapropylammonium iodide), which were used in the measurement.

Although present exemplary embodiments of the invention have been discussed above, it will be understood that variations and modifications may be made to the exemplary embodiments within the scope of the claims appended hereto.

---

The invention claimed is:

1. A method for specifically detecting an analyte, comprising the steps of:
    contacting a working electrode and a counter electrode with an electrolyte medium, the working electrode having an analyte immobilized thereon through a probe substance, the analyte being bonded to a sensitizing dye;
    irradiating the working electrode with light to photoexcite the sensitizing dye; and
    detecting photocurrent flowing between the working electrode and the counter electrode, the photocurrent being generated by transfer of electrons from the photoexcited sensitizing dye to the working electrode;
    wherein the working electrode comprises an electron accepting layer comprising an electron accepting substance capable of accepting electrons released from the sensitizing dye in response to photoexcitation, the probe substance being supported on a surface of the electron accepting layer;
    wherein the electron accepting substance is an oxide semiconductor having an energy level lower than that of a lowest unoccupied molecular orbit (LUMO) of the sensitizing dye;
    wherein the electrolyte medium comprises an electrolyte and at least one solvent selected from an aprotic solvent and a protic solvent, the electrolyte comprising a salt capable of providing an oxidized sensitizing dye with electrons; and
    wherein the electrolyte is at least one selected from the group consisting of tetraalkylammonium iodide, $Br_2$-free bromide, thiosulfate, and sulfite.

2. A method according to claim 1, wherein the electrolyte medium has a reduction potential of higher than an energy level of a highest occupied molecular orbit (HOMO) of the sensitizing dye and lower than an energy level of a conduction band of the electron accepting substance.

3. A method according to claim 1, wherein the electrolyte is tetraalkylammonium iodide.

4. A method according to claim 1, wherein the electrolyte is at least one selected from the group consisting of thiosulfate and sulfite.

5. A method according to claim 4, wherein the electrolyte is thiosulfate; and the thiosulfate is sodium thiosulfate.

6. A method according to claim 4, wherein the electrolyte is sulfite and wherein the sulfite is sodium sulfite.

7. A method according to claim 1, wherein the solvent is an aprotic solvent.

8. A method according to claim 7, wherein the aprotic solvent is acetonitrile ($CH_3CN$).

9. A method according to claim 1, wherein the solvent is a protic solvent.

10. A method according to claim 9, wherein the protic solvent is water.

11. A method according to claim 1, wherein the solvent is a mixture of an aprotic solvent and a protic solvent.

12. A method according to claim 1, wherein the electron accepting layer has a cationized surface.

13. A method according to claim 1, wherein a solution comprising the probe substance is brought into contact with the working electrode to make the probe substance supported on the electron accepting layer.

14. A method according to claim 1, further comprising the step of cleaning the working electrode with a cleaning fluid before contacting the working electrode and the counter electrode with the electrolyte medium.

15. A method according to claim 1, wherein the analyte is labeled with the sensitizing dye in advance.

16. A method according to claim 1, wherein the analyte is a single-stranded nucleic acid; and wherein the probe substance is a single-stranded nucleic acid having complementarity to the nucleic acid of the analyte.

17. A method according to claim 16, wherein the nucleic acid having the complementarity comprises a complementary portion which is 15bp longer than the nucleic acid.

18. A method according to claim 16, wherein the analyte is a nucleic acid labeled with the sensitizing dye in advance and wherein each molecule of the analyte is labeled with one or more of the sensitizing-dye.

19. A method according to claim 1, wherein the analyte is bonded to the probe substance by bringing a sample liquid comprising the analyte into contact with the working electrode under coexistence of the sensitizing dye; wherein the sample liquid further comprises a mediator substance capable of specifically bonding to the analyte, the mediator substance being labeled with the sensitizing dye in advance; and wherein a conjugate of the mediator substance and the analyte specifically bonds to the probe substance.

20. A method according to claim 19, wherein the analyte is a ligand, wherein the mediator substance is a receptor protein molecule and wherein the probe substance is a double-stranded nucleic acid.

21. A method according to claim 19, wherein the analyte is an endocrine disruptor.

22. A method according to claim 1, wherein the step of detecting the photocurrent comprises measuring an electric current value or an electrical quantity; and calculating concentration of the analyte in the sample liquid from the electric current value or electrical quantity thus measured.

23. A method according to claim 22, wherein the step of calculating concentration of the analyte in the sample liquid from the measured electric current value or electrical quantity is carried out by applying the measured electric current value or electric quantity to a pre-created calibration line of analyte concentration versus electric current value or electric quantity.

24. A method according to claim 22, wherein the analyte is bonded to the probe substance by bringing the sample liquid comprising the analyte into contact with the working electrode under coexistence of the sensitizing dye; wherein the sample liquid further comprises a second analyte capable of specifically bonding to the probe substance, the second analyte not being labeled with the sensitizing dye, so that the analyte and the second analyte compete to specifically bond to the probe substance; wherein the step of detecting the photocurrent comprises measuring an electric current value or an electrical quantity; and calculating concentration of the second analyte in the sample liquid from the measured electric current value or electrical quantity.

25. A method according to claim 24, wherein the step of calculating concentration of the second analyte in the sample liquid from the measured electric current value or electrical quantity is carried out by applying the measured electric current value or electric quantity to a pre-created calibration line of second-analyte concentration versus electric current value or electric quantity.

26. A method according to claim 24, wherein the analyte and the second analyte are an antigen and wherein the probe substance is an antibody.

27. A method according to claim 24, wherein the second analyte has greater tendency to bond specifically to the probe substance than the analyte.

28. A method according to claim 1, wherein the electron accepting substance comprises at least one selected from the group consisting of titanium oxide, zinc oxide, tin oxide, niobium oxide, indium oxide, tungsten oxide, tantalum oxide, and strontium titanate.

29. A method according to claim 28, wherein the electron accepting substance is titanium oxide or strontium titanate.

30. A method according to claim 28, wherein the electron accepting substance is either indium-tin composite oxide (ITO) or fluorine-doped tin oxide (FTO).

31. A method according to claim 1, wherein the working electrode further comprises an conductive substrate; and wherein the electron accepting layer is formed on the conductive substrate.

32. A method according to claim 1, wherein the sensitizing dye is a metal complex dye or an organic dye.

33. A method according to claim 32, wherein the sensitizing dye is at least one selected from the group consisting of metal phthalocyanines; chlorophyll and its derivatives; complexes of hemin, ruthenium, osmium, iron and zinc; metal-free phthalocyanine, 9-phenylxanthene dye, cyanine dye, metallocyanine dye, xanthene dye, triphenylmethane dye, acridine dye, oxazine dye, coumarin dye, merocyanine dye, rhodacyanine dye, polymethine dye, and indigo dye.

34. A method according to claim 32, wherein the sensitizing dye is at least one selected from the group consisting of Cy3, Cy5, Cy5.5, Cy7, Cy7.5, Cy9, FAM, FITC, HEX, Rhodamine, Rhodamine-green, ROX, TET, TEXAS RED, Beckman Dyes2, Beckman Dyes3, Beckman Dyes 4, fluorescein and Alexa Fluor dye.

35. A method according to claim 1, wherein there are two or more kinds of the analytes; wherein the analytes are respectively labeled with different sensitizing dyes capable of being excited with lights of different wavelengths from each other; and wherein each sensitizing dye is irradiated with the light of a different wavelength to detect each of the analytes individually.

36. A method according to claim 1, wherein the probe substance is supported on each of a plurality of regions isolated from each other on the working substrate; and wherein each region is individually irradiated with light.

37. A method according to claim 36, wherein the electron accepting layer is formed over the entire surface of the conductive substrate; and wherein photocurrent flowing through the conductive substrate as a whole is detected.

38. A method according to claim 36, wherein a plurality of kinds of the probe substances are supported on each of the plurality of regions isolated from each other on the working electrode, so that a plurality of sample liquids are measured simultaneously.

39. A method according to claim 36, wherein the probe substance is supported on each of the plurality of regions isolated from each other on the working electrode, the probe substance being different from region to region, so that a plurality of kinds of analytes are measured simultaneously.

40. A method according to claim 1, wherein the working electrode further comprises an insulating substrate; wherein spots comprising the conductive substrate and the electron accepting layer are formed on the insulating substrate, each of the spots being disposed in each of a plurality of regions isolated from each other; and wherein photocurrent flowing through the conductive substrate in each of the regions is individually detected.

41. A method according to claim 1, wherein the working electrode further comprises an insulating substrate; wherein spots comprising the electron accepting layer are separately formed on the insulating substrate, each of the spots being disposed in each of a plurality of regions isolated from each other; and wherein photocurrent flowing through the electron accepting layer in each of the regions is individually detected.

42. A method according to claim 1, wherein the light is substantially free from ultraviolet ray.

43. A method according to claim 42, wherein the light is emitted from at least one light source selected from the group consisting of a laser, an inorganic electroluminescence (EL) device, an organic electroluminescence (EL) device and a light-emitting diode (LED).

44. A method according to claim 1, wherein the light irradiation is carried out through means for removing ultraviolet ray.

45. A method according to claim 44, wherein the means for removing the ultraviolet ray is an optical filter or a spectroscope.

* * * * *

SEQUENCE LISTING

```
<160> NUMBER OF SEQ ID NOS: 14

<210> SEQ ID NO 1
<211> LENGTH: 25
<212> TYPE: DNA
<213> ORGANISM: Artificial
<220> FEATURE:
<223> OTHER INFORMATION: probe

<400> SEQUENCE: 1
accttcatca aaaacatcat catcc                                         25

<210> SEQ ID NO 2
<211> LENGTH: 25
<212> TYPE: DNA
<213> ORGANISM: Artificial
<220> FEATURE:
<223> OTHER INFORMATION: target (PM)

<400> SEQUENCE: 2
ggatgatgat gtttttgatg aaggt                                         25

<210> SEQ ID NO 3
<211> LENGTH: 24
<212> TYPE: DNA
<213> ORGANISM: Artificial
<220> FEATURE:
<223> OTHER INFORMATION: target (MM)

<400> SEQUENCE: 3
ttgagcaagt tcagcctggt taag                                          24

<210> SEQ ID NO 4
<211> LENGTH: 25
<212> TYPE: DNA
<213> ORGANISM: Artificial
<220> FEATURE:
<223> OTHER INFORMATION: probe (PM)

<400> SEQUENCE: 4
aggatgggcc tcaggttcat gccgc                                         25
```

```
<210> SEQ ID NO 5
<211> LENGTH: 25
<212> TYPE: DNA
<213> ORGANISM: Artificial
<220> FEATURE:
<223> OTHER INFORMATION: probe (SNP)

<400> SEQUENCE: 5
aggatgggcc tcgggttcat gccgc                                       25

<210> SEQ ID NO 6
<211> LENGTH: 25
<212> TYPE: DNA
<213> ORGANISM: Artificial
<220> FEATURE:
<223> OTHER INFORMATION: target

<400> SEQUENCE: 6
gcggcatgaa cctgaggccc atcct                                       25

<210> SEQ ID NO 7
<211> LENGTH: 25
<212> TYPE: DNA
<213> ORGANISM: Artificial
<220> FEATURE:
<223> OTHER INFORMATION: probe

<400> SEQUENCE: 7
aggatgggcc tcaggttcat gccgc                                       25

<210> SEQ ID NO 8
<211> LENGTH: 25
<212> TYPE: DNA
<213> ORGANISM: Artificial
<220> FEATURE:
<223> OTHER INFORMATION: target (PM)

<400> SEQUENCE: 8
gcggcatgaa cctgaggccc atcct                                       25

<210> SEQ ID NO 9
<211> LENGTH: 25
<212> TYPE: DNA
<213> ORGANISM: Artificial
<220> FEATURE:
<223> OTHER INFORMATION: target (SNP)

<400> SEQUENCE: 9
gcggcatgaa ccggaggccc atcct                                       25

<210> SEQ ID NO 10
<211> LENGTH: 25
<212> TYPE: DNA
<213> ORGANISM: Artificial
<220> FEATURE:
<223> OTHER INFORMATION: Probe (PM)

<400> SEQUENCE: 10
aggatgggcc tcaggttcat gccgc                                       25

<210> SEQ ID NO 11
<211> LENGTH: 25
<212> TYPE: DNA
<213> ORGANISM: Artificial
<220> FEATURE:
<223> OTHER INFORMATION: Probe (SNP)
```

```
<400> SEQUENCE: 11
aggatgggcc tccggttcat gccgc                                    25

<210> SEQ ID NO 12
<211> LENGTH: 25
<212> TYPE: DNA
<213> ORGANISM: Artificial
<220> FEATURE:
<223> OTHER INFORMATION: Probe (MM)

<400> SEQUENCE: 12
gcggcatgaa ccggaggccc atcct                                    25

<210> SEQ ID NO 13
<211> LENGTH: 25
<212> TYPE: DNA
<213> ORGANISM: Artificial
<220> FEATURE:
<223> OTHER INFORMATION: target

<400> SEQUENCE: 13
gcggcatgaa cctgaggccc atcct                                    25

<210> SEQ ID NO 14
<211> LENGTH: 30
<212> TYPE: DNA
<213> ORGANISM: Artificial
<220> FEATURE:
<223> OTHER INFORMATION: Oligo DNA

<400> SEQUENCE: 14
tggctcctga cctggagtct tccagtgtga                               30
```